United States Patent
Broedl et al.

(10) Patent No.: US 11,666,590 B2
(45) Date of Patent: *Jun. 6, 2023

(54) PHARMACEUTICAL COMPOSITION, METHODS FOR TREATING AND USES THEREOF

(71) Applicant: Boehringer Ingelheim International GmbH, Ingelheim am Rhein (DE)

(72) Inventors: Uli Christian Broedl, Oakville (CA); Odd-Erik Johansen, Hoevik (NO); Eric Williams Mayoux, Neauphle-le-Vieux (FR); Nima Soleymanlou, Maple (CA); Maximilian von Eynatten, Wiesbaden (DE); Hans-Juergen Woerle, Grandvaux VD (CH); David Z.I. Cherney, Toronto (CA); Bruce A. Perkins, Toronto (CA)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/094,037

(22) Filed: Nov. 10, 2020

(65) Prior Publication Data

US 2021/0228610 A1     Jul. 29, 2021

Related U.S. Application Data

(63) Continuation of application No. 16/738,112, filed on Jan. 9, 2020, now abandoned, which is a continuation of application No. 16/131,165, filed on Sep. 14, 2018, now abandoned, which is a continuation of application No. 15/899,499, filed on Feb. 20, 2018, now abandoned, which is a continuation of application No. 15/672,517, filed on Aug. 9, 2017, now abandoned, which is a continuation of application No. 14/918,818, filed on Oct. 21, 2015, now abandoned, which is a continuation of application No. 14/253,935, filed on Apr. 16, 2014, now abandoned.

(60) Provisional application No. 61/823,045, filed on May 14, 2013, provisional application No. 61/813,223, filed on Apr. 18, 2013.

(51) Int. Cl.
| | |
|---|---|
| A61K 31/7048 | (2006.01) |
| A61K 45/06 | (2006.01) |
| A61K 38/28 | (2006.01) |
| A61K 9/20 | (2006.01) |
| A61K 9/28 | (2006.01) |
| A61K 31/155 | (2006.01) |
| A61K 31/522 | (2006.01) |

(52) U.S. Cl.
CPC ........ *A61K 31/7048* (2013.01); *A61K 9/2018* (2013.01); *A61K 9/2866* (2013.01); *A61K 31/155* (2013.01); *A61K 31/522* (2013.01); *A61K 38/28* (2013.01); *A61K 45/06* (2013.01)

(58) Field of Classification Search
None
See application file for complete search history.

(56) References Cited

U.S. PATENT DOCUMENTS

| | | |
|---|---|---|
| 3,174,901 A | 3/1965 | Sterne |
| 3,884,906 A | 5/1975 | Van Der Meer et al. |
| 4,379,785 A | 4/1983 | Weyer et al. |
| 4,602,023 A | 7/1986 | Kiely et al. |
| 4,639,436 A | 1/1987 | Junge et al. |
| 4,786,023 A | 11/1988 | Harris et al. |
| 4,786,755 A | 11/1988 | Kiely et al. |
| 5,145,684 A | 9/1992 | Liversidge et al. |
| 5,516,530 A | 5/1996 | Lo et al. |
| 5,807,580 A | 9/1998 | Luber |
| 5,880,289 A | 3/1999 | Kaneko et al. |
| 6,414,126 B1 | 7/2002 | Ellsworth et al. |
| 6,498,193 B2 | 12/2002 | Beisswenger et al. |
| 6,515,117 B2 | 2/2003 | Ellsworth et al. |
| 6,613,806 B1 | 9/2003 | Aven et al. |
| 6,627,611 B2 | 9/2003 | Tomiyama et al. |
| 6,774,112 B2 | 8/2004 | Gougoutas |
| 6,794,480 B2 | 9/2004 | Goto et al. |
| 6,936,590 B2 | 8/2005 | Washburn et al. |
| 6,972,283 B2 | 12/2005 | Fujikura et al. |
| 6,995,183 B2 | 2/2006 | Hamann et al. |
| 7,101,856 B2 | 9/2006 | Glombik et al. |
| 7,169,761 B2 | 1/2007 | Tomiyama et al. |
| 7,202,350 B2 | 4/2007 | Imamura et al. |
| 7,294,618 B2 | 11/2007 | Fushimi et al. |
| 7,371,732 B2 | 5/2008 | Eickelmann et al. |
| 7,375,087 B2 | 5/2008 | Teranishi et al. |

(Continued)

FOREIGN PATENT DOCUMENTS

| | | |
|---|---|---|
| CA | 2382480 A1 | 3/2001 |
| CA | 2388818 A1 | 4/2001 |

(Continued)

OTHER PUBLICATIONS

Adachi et al., Metabolism, vol. 49 (8), Aug. 2000, pp. 990-995. (Year: 2000).*
Malatiali et al., Experimental Diabetes Research, 2008, vol. 2008, 7 pages. (Year: 2008).*
Vervoort et al., European Journal of Clinical Investigation, 2005, vol. 35, pp. 330-336. (Year: 2005).*
International Search Report for PCT/EP2011/054734 dated Aug. 12, 2011.
International Search Report for PCT/EP2011/069532 dated Dec. 15, 2011.

(Continued)

*Primary Examiner* — Traviss C McIntosh, III
(74) *Attorney, Agent, or Firm* — David L. Kershner

(57) ABSTRACT

The present invention relates to certain SGLT-2 inhibitors for treating, preventing, protecting against and/or delaying the progression of chronic kidney disease in patients, for example patients with prediabetes, type 1 or type 2 diabetes mellitus.

32 Claims, No Drawings

(56) References Cited

U.S. PATENT DOCUMENTS

| | | | |
|---|---|---|---|
| 7,375,090 B2 | 5/2008 | Himmelsbach et al. |
| 7,375,213 B2 | 5/2008 | Deshpande et al. |
| 7,393,836 B2 | 7/2008 | Eckhardt et al. |
| 7,407,955 B2 | 8/2008 | Himmelsbach et al. |
| 7,417,032 B2 | 8/2008 | Eckhardt et al. |
| 7,419,959 B2 | 9/2008 | Eckhardt et al. |
| 7,541,341 B2 | 6/2009 | Fushimi et al. |
| 7,579,449 B2 | 8/2009 | Eckhardt et al. |
| 7,589,193 B2 | 9/2009 | Washburn et al. |
| 7,662,790 B2 | 2/2010 | Himmelsbach et al. |
| 7,674,486 B2 | 3/2010 | Bhaskaran et al. |
| 7,683,160 B2 | 3/2010 | Eckhardt et al. |
| 7,687,469 B2 | 3/2010 | Eckhardt et al. |
| 7,713,938 B2 * | 5/2010 | Himmelsbach ........... A61P 3/10 514/23 |
| 7,723,309 B2 | 5/2010 | Himmelsbach et al. |
| 7,723,379 B2 | 5/2010 | Romanczyk, Jr. et al. |
| 7,745,414 B2 | 6/2010 | Eckhardt et al. |
| 7,772,191 B2 | 8/2010 | Eckhardt et al. |
| 7,772,192 B2 | 8/2010 | Esko |
| 7,772,378 B2 | 8/2010 | Himmelsbach et al. |
| 7,772,407 B2 | 8/2010 | Imamura et al. |
| 7,776,830 B2 | 8/2010 | Eckhardt et al. |
| 7,847,074 B2 | 12/2010 | Eckhardt et al. |
| 7,851,502 B2 | 12/2010 | Bindra et al. |
| 7,851,602 B2 | 12/2010 | Himmelsbach et al. |
| 7,858,587 B2 | 12/2010 | Eckhardt et al. |
| 7,879,806 B2 | 2/2011 | Himmelsbach et al. |
| 7,879,807 B2 | 2/2011 | Himmelsbach et al. |
| 8,039,441 B2 | 10/2011 | Himmelsbach et al. |
| 8,119,648 B2 | 2/2012 | Himmelsbach et al. |
| 8,178,541 B2 | 5/2012 | Himmelsbach et al. |
| 8,232,281 B2 | 7/2012 | Dugi et al. |
| 8,283,326 B2 | 10/2012 | Eckhardt et al. |
| 8,507,450 B2 | 8/2013 | Eckhardt et al. |
| 8,551,957 B2 * | 10/2013 | Dugi ................. A61K 9/145 514/23 |
| 8,557,782 B2 | 10/2013 | Eckhardt et al. |
| 8,802,842 B2 | 8/2014 | Weber et al. |
| 9,024,010 B2 | 5/2015 | Weber et al. |
| 9,034,883 B2 | 5/2015 | Klein et al. |
| 9,127,034 B2 | 9/2015 | Eckhardt et al. |
| 9,192,616 B2 | 11/2015 | Johnson |
| 9,192,617 B2 * | 11/2015 | Mayoux ............... A61K 31/365 |
| 9,949,997 B2 | 4/2018 | Broedl et al. |
| 9,949,998 B2 * | 4/2018 | Broedl ................ A61K 9/2866 |
| 10,258,637 B2 * | 4/2019 | Broedl ................ A61K 9/2866 |
| 10,406,172 B2 * | 9/2019 | Eickelmann .............. A61P 3/12 |
| 10,596,120 B2 | 3/2020 | Ito et al. |
| 10,610,489 B2 | 4/2020 | Schneider et al. |
| 11,090,323 B2 * | 8/2021 | Broedl ............... A61K 31/7034 |
| 2001/0018090 A1 | 8/2001 | Noda et al. |
| 2001/0041674 A1 | 11/2001 | Tomiyama et al. |
| 2001/0044435 A1 | 11/2001 | Himmelsbach et al. |
| 2002/0137903 A1 | 9/2002 | Ellsworth et al. |
| 2002/0173509 A1 | 11/2002 | Himmelsbach et al. |
| 2002/0198205 A1 | 12/2002 | Himmelsbach et al. |
| 2003/0064935 A1 | 4/2003 | Gougoutas |
| 2003/0087843 A1 | 5/2003 | Washburn |
| 2003/0114390 A1 | 6/2003 | Washburn et al. |
| 2003/0212070 A1 | 11/2003 | Schwink et al. |
| 2004/0097510 A1 | 5/2004 | Himmelsbach et al. |
| 2004/0138148 A1 | 7/2004 | Fushimi et al. |
| 2004/0138439 A1 | 7/2004 | Deshpande et al. |
| 2004/0247677 A1 | 12/2004 | Oury et al. |
| 2004/0259819 A1 | 12/2004 | Frick et al. |
| 2005/0065098 A1 | 3/2005 | Fujikura et al. |
| 2005/0085680 A1 | 4/2005 | Auerbach et al. |
| 2005/0124555 A1 | 6/2005 | Tomiyama et al. |
| 2005/0187168 A1 | 8/2005 | Eickelmann et al. |
| 2005/0209166 A1 | 9/2005 | Eckhardt et al. |
| 2005/0209309 A1 | 9/2005 | Sato et al. |
| 2005/0233982 A1 | 10/2005 | Himmelsbach et al. |
| 2005/0234108 A1 | 10/2005 | Himmelsbach et al. |
| 2006/0009400 A1 | 1/2006 | Eckhardt et al. |
| 2006/0019948 A1 | 1/2006 | Eckhardt et al. |
| 2006/0025349 A1 | 2/2006 | Eckhardt et al. |
| 2006/0035841 A1 | 2/2006 | Eckhardt et al. |
| 2006/0063722 A1 | 3/2006 | Washburn et al. |
| 2006/0074031 A1 | 4/2006 | Eckhardt et al. |
| 2006/0079541 A1 | 4/2006 | Langkopf et al. |
| 2006/0142210 A1 | 6/2006 | Eckhardt et al. |
| 2006/0189548 A1 | 8/2006 | Himmelsbach et al. |
| 2006/0210627 A1 | 9/2006 | Pfeffer et al. |
| 2006/0234953 A1 | 10/2006 | Himmelsbach et al. |
| 2006/0251728 A1 | 11/2006 | Himmelsbach et al. |
| 2006/0258749 A1 | 11/2006 | Eckhardt et al. |
| 2006/0287242 A1 | 12/2006 | Ewing et al. |
| 2007/0004648 A1 | 1/2007 | Himmelsbach et al. |
| 2007/0027092 A1 | 2/2007 | Himmelsbach et al. |
| 2007/0042042 A1 | 2/2007 | Jo et al. |
| 2007/0049537 A1 | 3/2007 | Eckhardt et al. |
| 2007/0054867 A1 | 3/2007 | Eckhardt et al. |
| 2007/0073046 A1 | 3/2007 | Eckhardt et al. |
| 2007/0249544 A1 | 10/2007 | Himmelsbach et al. |
| 2007/0259821 A1 | 11/2007 | Eckhardt et al. |
| 2007/0281940 A1 | 12/2007 | Dugi et al. |
| 2008/0058379 A1 | 3/2008 | Eckhardt et al. |
| 2008/0107731 A1 | 5/2008 | Kohlrausch et al. |
| 2008/0234367 A1 | 9/2008 | Washburn et al. |
| 2008/0287529 A1 | 11/2008 | Deshpande et al. |
| 2009/0023913 A1 | 1/2009 | Eckhardt et al. |
| 2009/0137499 A1 | 5/2009 | Honda et al. |
| 2009/0281078 A1 | 11/2009 | Routledge et al. |
| 2009/0318547 A1 | 12/2009 | Eckhardt et al. |
| 2009/0326215 A1 | 12/2009 | Eckhardt et al. |
| 2010/0069310 A1 | 3/2010 | Himmelsbach et al. |
| 2010/0074950 A1 | 3/2010 | Sesha |
| 2010/0081625 A1 | 4/2010 | Wienrich et al. |
| 2010/0093654 A1 | 4/2010 | Himmelsbach et al. |
| 2010/0099641 A1 | 4/2010 | Himmelsbach et al. |
| 2010/0179191 A1 | 7/2010 | Himmelsbach et al. |
| 2010/0209506 A1 | 8/2010 | Eisenreich |
| 2010/0240879 A1 | 9/2010 | Eckhardt et al. |
| 2010/0249392 A1 | 9/2010 | Eckhardt et al. |
| 2010/0298243 A1 | 11/2010 | Manuchehri et al. |
| 2010/0317847 A1 | 12/2010 | Eckhardt et al. |
| 2011/0014284 A1 | 1/2011 | Eisenreich et al. |
| 2011/0015225 A1 | 1/2011 | Murata et al. |
| 2011/0046076 A1 | 2/2011 | Eickelmann et al. |
| 2011/0046087 A1 | 2/2011 | Eickelmann et al. |
| 2011/0065731 A1 | 3/2011 | Dugi et al. |
| 2011/0077212 A1 | 3/2011 | Seed et al. |
| 2011/0098240 A1 | 4/2011 | Dugi et al. |
| 2011/0178033 A1 | 7/2011 | Eckhardt et al. |
| 2011/0195917 A1 | 8/2011 | Dugi et al. |
| 2011/0206766 A1 | 8/2011 | Friedl et al. |
| 2011/0236477 A1 | 9/2011 | Schneider et al. |
| 2011/0237526 A1 | 9/2011 | Weber et al. |
| 2011/0237789 A1 | 9/2011 | Weber et al. |
| 2012/0041069 A1 | 2/2012 | Sesha |
| 2012/0071403 A1 | 3/2012 | Strumph et al. |
| 2012/0094894 A1 | 4/2012 | Graefe-Mody et al. |
| 2012/0121530 A1 | 5/2012 | Klein et al. |
| 2012/0196812 A1 | 8/2012 | Eickelmann et al. |
| 2012/0219622 A1 | 8/2012 | Kohlrausch et al. |
| 2012/0283169 A1 | 11/2012 | Grempler et al. |
| 2012/0296080 A1 | 11/2012 | Eckhardt et al. |
| 2013/0035281 A1 | 2/2013 | Klein et al. |
| 2013/0035298 A1 | 2/2013 | Broedl et al. |
| 2013/0064887 A1 | 3/2013 | Ito et al. |
| 2013/0096076 A1 | 4/2013 | Dugi et al. |
| 2013/0137646 A1 | 5/2013 | Wienrich et al. |
| 2013/0236543 A1 | 9/2013 | Ito et al. |
| 2013/0252908 A1 | 9/2013 | Mayoux et al. |
| 2014/0031301 A1 | 1/2014 | Eickelmann et al. |
| 2014/0038911 A1 | 2/2014 | Eickelmann et al. |
| 2014/0046046 A1 | 2/2014 | Eckhardt et al. |
| 2014/0087996 A1 | 3/2014 | Klein et al. |
| 2014/0088027 A1 | 3/2014 | Grempler et al. |
| 2014/0256624 A1 | 9/2014 | Grempler et al. |
| 2014/0303097 A1 | 10/2014 | Broedl et al. |
| 2014/0303098 A1 | 10/2014 | Broedl et al. |
| 2014/0315832 A1 | 10/2014 | Broedl et al. |

(56) References Cited

U.S. PATENT DOCUMENTS

| | | | |
|---|---|---|---|
| 2015/0272977 | A1 | 10/2015 | Reiche et al. |
| 2015/0322053 | A1 | 11/2015 | Eckhardt et al. |
| 2016/0000816 | A1 | 1/2016 | Broedl et al. |
| 2016/0030385 | A1 | 2/2016 | Manuchehri et al. |
| 2016/0038523 | A1 | 2/2016 | Broedl et al. |
| 2016/0038524 | A1 | 2/2016 | Broedl et al. |
| 2016/0038525 | A1 | 2/2016 | Broedl et al. |
| 2016/0074415 | A1 | 3/2016 | Wienrich et al. |
| 2017/0020907 | A1 | 1/2017 | Eickelmann et al. |
| 2017/0095424 | A1 | 4/2017 | Ito et al. |
| 2017/0106009 | A1 | 4/2017 | Mayoux |
| 2017/0189437 | A1 | 7/2017 | Manuchehri et al. |
| 2017/0266152 | A1 | 9/2017 | Broedl et al. |
| 2017/0305952 | A1 | 10/2017 | Klein et al. |
| 2017/0333465 | A1 | 11/2017 | Broedl et al. |
| 2018/0104249 | A1 | 4/2018 | Eisenreich |
| 2018/0104268 | A1 | 4/2018 | Mayoux et al. |
| 2018/0125813 | A1 | 5/2018 | von Eynatten et al. |
| 2018/0169126 | A1 | 6/2018 | Broedl et al. |
| 2018/0177794 | A1 | 6/2018 | Wienrich et al. |
| 2018/0185291 | A1 | 7/2018 | Ito et al. |
| 2018/0193427 | A1 | 7/2018 | Grempler et al. |
| 2018/0200278 | A1 | 7/2018 | Broedl et al. |
| 2018/0214468 | A1 | 8/2018 | Broedl et al. |
| 2018/0289678 | A1 | 10/2018 | Eisenreich et al. |
| 2018/0318251 | A1 | 11/2018 | Broedl et al. |
| 2018/0344647 | A1 | 12/2018 | Boeck et al. |
| 2019/0015437 | A1 | 1/2019 | Broedl et al. |
| 2019/0038654 | A1 | 2/2019 | Broedl et al. |
| 2019/0134072 | A1 | 5/2019 | Broedl et al. |
| 2019/0209596 | A1 | 7/2019 | Mayoux |
| 2019/0298749 | A1 | 10/2019 | Mayoux et al. |
| 2019/0309004 | A1 | 10/2019 | Wirth et al. |
| 2019/0350894 | A1 | 11/2019 | Broedl et al. |
| 2019/0350957 | A1 | 11/2019 | Broedl et al. |
| 2020/0069713 | A1 | 3/2020 | Eickelmann et al. |
| 2020/0085851 | A1 | 3/2020 | Eickelmann et al. |
| 2020/0138770 | A1 | 5/2020 | von Eynatten et al. |
| 2020/0138844 | A1 | 5/2020 | Broedl et al. |
| 2020/0188306 | A1 | 6/2020 | Schneider et al. |
| 2020/0222423 | A1 | 7/2020 | Wienrich et al. |
| 2020/0268777 | A1 | 8/2020 | Broedl et al. |
| 2020/0297639 | A1 | 9/2020 | Ito et al. |
| 2020/0360412 | A1 | 11/2020 | Broedl et al. |
| 2020/0368261 | A1 | 11/2020 | Broedl et al. |
| 2020/0397809 | A1 | 12/2020 | Mayoux |
| 2020/0397867 | A1 | 12/2020 | Grempler et al. |
| 2021/0059974 | A1 | 3/2021 | Broedl et al. |
| 2021/0228533 | A1 | 7/2021 | von Eynatten et al. |
| 2021/0228610 | A1 | 7/2021 | Broedl et al. |
| 2021/0299153 | A1 | 9/2021 | Broedl et al. |

FOREIGN PATENT DOCUMENTS

| | | | |
|---|---|---|---|
| CA | 2402609 | A1 | 9/2001 |
| CA | 2423568 | A1 | 4/2002 |
| CA | 2432428 | A1 | 6/2002 |
| CA | 2437240 | A1 | 8/2002 |
| CA | 2478889 | A1 | 2/2004 |
| CA | 2494177 | A1 | 2/2004 |
| CA | 2496249 | A1 | 3/2004 |
| CA | 2470365 | A1 | 6/2004 |
| CA | 2508024 | A1 | 6/2004 |
| CA | 2508226 | A1 | 6/2004 |
| CA | 2526145 | A1 | 9/2004 |
| CA | 2539032 | A1 | 3/2005 |
| CA | 2548353 | A1 | 7/2005 |
| CA | 2557269 | A1 | 9/2005 |
| CA | 2557320 | A1 | 9/2005 |
| CA | 2557801 | A1 | 10/2005 |
| CA | 2569915 | A1 | 1/2006 |
| CA | 2572149 | A1 | 1/2006 |
| CA | 2572819 | A1 | 1/2006 |
| CA | 2573777 | A1 | 2/2006 |
| CA | 2574451 | A1 | 2/2006 |
| CA | 2574500 | A1 | 4/2006 |
| CA | 2586938 | A1 | 5/2006 |
| CA | 2649922 | A1 | 11/2007 |
| CA | 2651019 | A1 | 11/2007 |
| CA | 2720450 | A1 | 10/2009 |
| CA | 2812519 | A1 | 10/2014 |
| CN | 1342151 | A | 3/2002 |
| CN | 1418219 | A | 5/2003 |
| CN | 1481370 | A | 3/2004 |
| CN | 1930141 | A | 3/2007 |
| CN | 101503399 | A | 8/2009 |
| CN | 101638423 | A | 2/2010 |
| DE | 2758025 | A1 | 7/1979 |
| DE | 2951135 | A1 | 6/1981 |
| EP | 0206567 | A2 | 12/1986 |
| EP | 1224195 | B | 7/2002 |
| EP | 1344780 | A1 | 9/2003 |
| EP | 1364957 | A1 | 11/2003 |
| EP | 1385856 | A | 2/2004 |
| EP | 1553094 | A1 | 7/2005 |
| EP | 1564210 | A1 | 8/2005 |
| EP | 1609785 | A1 | 12/2005 |
| EP | 1791852 | A2 | 6/2007 |
| EP | 1803729 | A1 | 7/2007 |
| EP | 1852108 | A1 | 11/2007 |
| EP | 2187879 | A1 | 5/2010 |
| EP | 2981271 | B1 | 11/2018 |
| JP | 55007256 | A | 1/1980 |
| JP | 56039056 | A | 4/1981 |
| JP | 58164502 | | 9/1983 |
| JP | 62030750 | A | 2/1987 |
| JP | H1085502 | A | 4/1998 |
| JP | 11124392 | A | 5/1999 |
| JP | 2001288178 | A | 10/2001 |
| JP | 2002338471 | A | 11/2002 |
| JP | 2003511458 | A | 3/2003 |
| JP | 2004196788 | A | 7/2004 |
| JP | 2004359630 | | 12/2004 |
| JP | 2005002092 | A | 1/2005 |
| JP | 2005060625 | A | 3/2005 |
| JP | 2006176443 | A | 7/2006 |
| JP | 2008540373 | A | 11/2008 |
| WO | 9520578 | A1 | 8/1995 |
| WO | 9725992 | A1 | 7/1997 |
| WO | 9831697 | A1 | 7/1998 |
| WO | 200031050 | A1 | 6/2000 |
| WO | 200035457 | A1 | 6/2000 |
| WO | 2001016147 | A1 | 3/2001 |
| WO | 2001027128 | A1 | 4/2001 |
| WO | 2001074834 | A1 | 10/2001 |
| WO | 2002064549 | | 8/2002 |
| WO | 2002064606 | A1 | 8/2002 |
| WO | 2002068420 | A1 | 9/2002 |
| WO | 2002083066 | A2 | 10/2002 |
| WO | 2003015769 | | 2/2003 |
| WO | 2003020737 | A1 | 3/2003 |
| WO | 2003031458 | A1 | 4/2003 |
| WO | 200347563 | A1 | 6/2003 |
| WO | 2003064411 | | 8/2003 |
| WO | 2003078404 | A1 | 9/2003 |
| WO | 2003099836 | A1 | 12/2003 |
| WO | 2003104223 | A1 | 12/2003 |
| WO | 2003106420 | A1 | 12/2003 |
| WO | 2004006846 | A2 | 1/2004 |
| WO | 2004007458 | A1 | 1/2004 |
| WO | 2004007517 | A1 | 1/2004 |
| WO | 2004013118 | A1 | 2/2004 |
| WO | 2004014931 | A1 | 2/2004 |
| WO | 2004018468 | A2 | 3/2004 |
| WO | 2004046115 | A1 | 6/2004 |
| WO | 2004052902 | A1 | 6/2004 |
| WO | 2004052903 | A1 | 6/2004 |
| WO | 2004063209 | A2 | 7/2004 |
| WO | 2004076470 | A2 | 9/2004 |
| WO | 2004080990 | A1 | 9/2004 |
| WO | 2005011592 | A2 | 2/2005 |
| WO | 2005011786 | A1 | 2/2005 |
| WO | 2005012318 | A2 | 2/2005 |
| WO | 2005012326 | A1 | 2/2005 |

(56) References Cited

FOREIGN PATENT DOCUMENTS

| | | |
|---|---|---|
| WO | 2005021566 A2 | 3/2005 |
| WO | 2005049022 A2 | 6/2005 |
| WO | 2005063785 A2 | 7/2005 |
| WO | 2005067976 A2 | 7/2005 |
| WO | 2005085237 A1 | 9/2005 |
| WO | 2005085246 A1 | 9/2005 |
| WO | 2005085265 A1 | 9/2005 |
| WO | 2005092877 A1 | 10/2005 |
| WO | 2005117861 A1 | 12/2005 |
| WO | 2006002912 A1 | 1/2006 |
| WO | 2006006496 A1 | 1/2006 |
| WO | 2006008038 A1 | 1/2006 |
| WO | 2006010557 A1 | 2/2006 |
| WO | 2006011469 A1 | 2/2006 |
| WO | 2006018150 A1 | 2/2006 |
| WO | 2006034489 A2 | 3/2006 |
| WO | 2006037537 A2 | 4/2006 |
| WO | 2006048427 A1 | 5/2006 |
| WO | 2006064033 A2 | 6/2006 |
| WO | 2006078593 A2 | 7/2006 |
| WO | 2006089872 A1 | 8/2006 |
| WO | 2006108842 A1 | 10/2006 |
| WO | 2006117359 A1 | 11/2006 |
| WO | 2006117360 A1 | 11/2006 |
| WO | 2006120208 A1 | 11/2006 |
| WO | 2007000445 A1 | 1/2007 |
| WO | 2007014894 A2 | 2/2007 |
| WO | 2007025943 A2 | 3/2007 |
| WO | 2007028814 A1 | 3/2007 |
| WO | 2007031548 A2 | 3/2007 |
| WO | 2007033350 A1 | 3/2007 |
| WO | 2007039417 A1 | 4/2007 |
| WO | 2007041053 A2 | 4/2007 |
| WO | 2007093610 A1 | 8/2007 |
| WO | 2007128724 A1 | 11/2007 |
| WO | 2007128749 A1 | 11/2007 |
| WO | 2007128761 A2 | 11/2007 |
| WO | 2007136116 A2 | 11/2007 |
| WO | 2007144175 A2 | 12/2007 |
| WO | 2008002905 A2 | 1/2008 |
| WO | 2008020011 A1 | 2/2008 |
| WO | 2008022267 A2 | 2/2008 |
| WO | 2008034859 A1 | 3/2008 |
| WO | 2008049923 A1 | 5/2008 |
| WO | 2008055870 A1 | 5/2008 |
| WO | 2008055940 A2 | 5/2008 |
| WO | 2008062273 A2 | 5/2008 |
| WO | 2008089892 A1 | 7/2008 |
| WO | 2008090210 A1 | 7/2008 |
| WO | 2008101938 A1 | 8/2008 |
| WO | 2008101939 A1 | 8/2008 |
| WO | 2008101943 A1 | 8/2008 |
| WO | 2008116179 A1 | 9/2008 |
| WO | 2008116195 A2 | 9/2008 |
| WO | 2008130615 A1 | 10/2008 |
| WO | 2008131149 A2 | 10/2008 |
| WO | 2009022007 A1 | 2/2009 |
| WO | 2009022010 A1 | 2/2009 |
| WO | 2009035969 A1 | 3/2009 |
| WO | 2009091082 A1 | 7/2009 |
| WO | 2009099734 A1 | 8/2009 |
| WO | 2009121945 A2 | 10/2009 |
| WO | 2009123194 A1 | 10/2009 |
| WO | 2010045656 A2 | 4/2010 |
| WO | 2010049678 A2 | 5/2010 |
| WO | 2010072776 A1 | 7/2010 |
| WO | 2010092123 A1 | 8/2010 |
| WO | 2010092124 A1 | 8/2010 |
| WO | 2010092125 A1 | 8/2010 |
| WO | 2010092126 A1 | 8/2010 |
| WO | 2010119990 A1 | 10/2010 |
| WO | 2010138535 A1 | 12/2010 |
| WO | 2011039107 A1 | 4/2011 |
| WO | 2011039108 A2 | 4/2011 |
| WO | 2011039337 A1 | 4/2011 |
| WO | 2011060290 A2 | 5/2011 |
| WO | 2011120923 A1 | 10/2011 |
| WO | 2012031124 A2 | 3/2012 |
| WO | 2012062698 A1 | 5/2012 |
| WO | 2012065993 A1 | 5/2012 |
| WO | 2012106303 A1 | 8/2012 |
| WO | 2012107476 A1 | 8/2012 |
| WO | 2012120040 A1 | 9/2012 |
| WO | 2012163990 A1 | 12/2012 |
| WO | 2013007557 A1 | 1/2013 |
| WO | 2013106547 A1 | 7/2013 |
| WO | 2013131967 A1 | 9/2013 |
| WO | 2013139777 A1 | 9/2013 |
| WO | 2014011926 A1 | 1/2014 |
| WO | 2014161918 A1 | 10/2014 |
| WO | 2014161919 A1 | 10/2014 |
| WO | 2014170383 A1 | 10/2014 |
| WO | 2016046150 A1 | 3/2016 |

OTHER PUBLICATIONS

International Search Report for PCT/EP2012/052108 dated Mar. 8, 2012.
International Search Report for PCT/EP2012/053910 dated May 14, 2012.
International Search Report for PCT/EP2012/060194 dated Jul. 17, 2012.
International Search Report for PCT/EP2013/054524 dated May 6, 2013.
International Search Report for PCT/EP2013/055671 dated Apr. 16, 2013.
International Search Report for PCT/EP2014/056655 filed Apr. 3, 2014.
International Search Report for PCT/EP2014/056657 filed Apr. 3, 2014.
International Search Report for PCT/EP2014/057754 filed Apr. 16, 2014.
International Search Report for PCT/EP2014/057754 dated May 27, 2014.
International Search Report for PCT/EP2016/074601 dated Dec. 16, 2016.
International Search Report for PCT/EP2017/075664 dated Dec. 8, 2017.
International Search Report for PCT/EP2017/078577 dated Feb. 1, 2018.
International Search Report PCT/EP2016/059525 dated Jun. 24, 2016. 4 pgs.
Invokana, Prescribing Information, Manufactured by Janssen Ortho LLC., published by the FDA on Mar. 29, 2013, 41 pgs.
Invokana, Press Release "U.S. FDA Approves INVOKANA™ (Canagliflozin) for the Treatment of Adults with Type 2 Diabetes" Janssen Pharmaceuticals, in partnership with Johnson & Johnson on Mar. 29, 2013, 7 pgs.
Inzucchi, Silvo E. "Oral Antihyperglycemic Therapy for Type 2 Diabetes" (2002) JAMA, vol. 287, No. 3, 360-372.
Isaji, Masayuki "Sodium-glucose cotransporter inhibitors for diabetes" Current Opinion in Investigational Drugs, (2007) vol. 8, No. 4, pp. 285-292.
Jabbour, S.A. et al. "Sodium glucose co-transporter 2 inhibitors: blocking renal tubular reabsorption of glucose to improve glycaemic control in patients with diabetes" (2008) Int J Clin Pract, 62, 8, 1279-1284.
Jabbour, Serge A. "The Importance of Reducing Hyperglycemia While Preserving Insulin Secretion—The Rational for Sodium-coupled Glucose Co-trnasporter 2 Inhibition in Diabetes" Touch Briefings, US Endocrinology (2009) pp. 75-78.
Jagdmann JR, G. Erik ; Synthesis of 5-(4-Substituted Benzyl)-2,4-Diaminoquinazolines as Inhibitors of Candida Albicans Dihydrofolate Reductase; Journal Heterocyclic Chemical (1995) vol. 32 pp. 1461-1465.
Jardiance, Product Information, Boehringer Ingelheim, Jun. 16, 2014, 47 pgs.

(56) References Cited

OTHER PUBLICATIONS

Jeremy, J.Y. et al. "Reactive oxygen species and erectile dysfunction: possible role of NADPH oxidase" (2007) International Journal of Impotence Research, 19, 265-280.
Johnson & Johnson "FDA Advisory Committee Recommends Approval of Canagliflozin for Treatment of Adults with Type 2 Diabetes" (2013) Press Release, 3 pgs.
Jones, Byrony "Empagliflozin—one step closer to glycaemic control in patients with type II diabetes and CKD?" (2014) Nature Reviews Nephrology 10, 181, 2 pgs.
Joshi, Shashank R. "Metformin: Old Wine in New Bottle—Evolving Technology and Therapy in Diabetes" Journal of Association of Physicians in India, (2005) vol. 53, pp. 963-972.
Kadowaki, T et al. "PPAR gamma agonist and antagonist" Nihon Yakurigaku Zasshi (2001) vol. 118, No. 9, pp. 321-326 (English abstract).
Kashihara, Naoki et al. "Renin-Angiotensin System" (2011) Angiotensin Research, vol. 8, No. 2, p. 40(96)-46(102).
Kasichayanula, Sreeneeranj et al. "The Influence of Kidney Function on Dapagliflozin Exposure, Metabolism and Pharmacodynamics in Healthy Subjects and in Patients with Type 2 Diabetes Mellitus" (2012) British Journal of Clinical Pharmacology, vol. 76, Issue 3, pp. 432-444.
Katsuno, Kenji et al. "Sergliflozin, a Novel Selective Inhibitor of Low-Affinity Sodium Glucose Cotransporter (SGLT2) Validates the Critical Role of SGLT2 in Renal Glucose Reabsorption and Modulates Plasma Glucose Level" The Journal of Pharmacology and Experimental Therapeutics (2007) vol. 320, No. 1, pp. 323-330.
Kautz, S. et al. "Early insulin therapy prevents beta cell loss in a mouse model for permanent neonatal diabetes (Munich lns2C95s)" Diabetologia (2012) vol. 55, pp. 382-391.
Kharasch, M.S et al. "Factors Determining the Course and Mechanisms of Grignard Reactions." Journal of American Chemical Society, (1941) vol. 63, 2316-2320.
Knochel, Paul et al. "Highly functionalized Organomagnesium Reagents Prepared through Halogen-Metal Exchange" Angew. Chem. INt. Ed. (2003) vol. 42, 4302-4320.
Kohan, Donald E. et al. "Abstract: [TH-P0524] Efficacy and Safety of Dapagliflozin in Patients with Type 2 Diabetes and Moderate Renal Impairment" Nov. 10, 2011, Abstract Sessions, 1 pg, http://www.abstracts2view.com.
Kohan, Donald E. et al. "Long-term study of patients with type 2 diabetes and moderate renal impairment shows that dapagliflozin reduces weight and blood pressure but does not improve glycemic control" (2013) Kidney International; 85, 962-971.
Kojima, Naoki et al. "Effects of a New SGLT2 Inhibitor, Luseogliflozin on Diabetic Nephropathy in T2DN Rats" The Journal of Pharmacology and Experimental Therapeutics, (2013) V 345, pp. 464-472.
Komala, Muralikrishan G. et al. "Sodium glucose cotransporter 2 and the diabetic kidney" (2013) Curr Opin Nephrol Hypertens, vol. 22, 113-119.
Koo, JA Seo., et al; 2-Pyridyl Cyanate: A Useful Reagent for he Preparation of Nitriles; Synthetic Communications (1996) vol. 26 No. 20 pp. 3709-3713; Marcel Dekker, Inc.
Krasovskiy Arkady et al. "A LiCL-Mediated Br/Mg Exchange Reaction for the Preparation of Functionalized Aryl-and Heterarylmagnesium Compounds from Organic Bromides**" Angew. Chem. Int. Ed. (2004) vol. 43, pp. 3333-3336.
Kuribayashi, Takeshi., et al; Bis C-Glycosylated Diphenylmethanes for Stable Glycoepitope Mimetics Syntletters (1999) vol. 6 pp. 737-740.
Kuribayashi, Takeshi., et al.; c-Glycosylated Aryl tins: Versatile Building Blocks for Aryl C-Glycoside Glycomimetics; J. Carbohydrate Chemistry (1999) vol. 18, No. 4 pp. 371-382.
Kuribayashi, Takeshi., et al; C-Glycosylated Diphenylmethanes and Benzophenones: The Stille Coupling Reaction of C-Glycosylated Aryl tins with Benzyl Bromides and Acid Chlorides; J. Carbohydrate Chemistry (1999) vol. 18, No. 4 pp. 393-401.

Kuritzky, Louis "Addition of Basal Insulin to Oral Antidiabetic Agents: A Goal-Directed Approach to Type 2 Diabetes Therapy" (2006) MedGenMed. 8(4) 34, 19 pgs.
Lab Cat. "Strong and Weak Acids" Feb. 2007; https://cdavies.wordpress.com/2007/02/27/strong-and-weak-acids/.
Lancet "Getting to the heart of the matter in type 2 diabetes" Editorial, (2015) 1 pg.
Langle, Sandrine., et al; Selective Double Suzuki Cross-Coupling Reactions. Synthesis of Unsymmetrical Diaryl (or Heteroaryl) Methanes; Tetrahedron Letters (2003) vol. 44 pp. 9255-9258; Pergamon Press.
Langley, Alissa K, et al. "Dipeptidyl Peptidase IV Inhibitors and the Incretin System in Type 2 Diabetes Mellitus" (2007) Pharmacotherapy, vol. 27, No. 8, 1163-1180.
Larsen, Mogens Lytken et al. "Effect of Long-Term Monitoring of Glycosylated Hemoglobin Levels in Insulin-Dependent Diabetes Mellitus" (1990) The New England Journal of Medicine, vol. 323, No. 15, 1021-1025.
Lebovitz, Harold E. "Insulin secretagogues: old and new" (1999) Diabetes Review, vol. 7, 139-153.
Abdul-Ghani, Muhammad "Where does Combination Therapy with an SGLT2 Inhibitor Plus a DPP-4 Inhibitor Fit in the Management of Type 2 Diabetes?" (2015) Diabetes Care, 38, 373-375.
Abdul-Ghani, Muhammad A. et al. "Efficacy and Safety of SGLT2 Inhibitors in the Treatment of Type 2 Diabetes Mellitus" (2012) Curr Diab Rep 12: 230-238.
Abdul-Ghani, Muhammad A. et al. "Role of Sodium-Glucose Cotransporter 2 (SGLT 2) Inhibitors in the Treatment of Type 2 Diabetes" (2011) Endocrine Reviews, 32(4), 515-531.
Abstract ASN09L1_307a "Contact View (TH-P0751) Kidney Function and Response to Diabetes in Mice Lacking SGLT2", VALLON, Volker et al., Oct. 29, 2009, 1 pg.
Abstract ASN09L1_4153a, "Contact View (SA-P02723) Chronic SGLT2 Blockade Reduces Proximal Reabsorption and Normalizes State of Tubuloglomerular Feedback Activation in Hyperfiltering Diabetic Rats" Thomson, Scott et al., Oct. 31, 2009, 1 pg.
Agarwal, Ashok et al. "Role of Oxidative Stress in the Pathophysiological Mechanism of Erectile Dysfunction" (2006) Journal of Andrology, V 27, No. 3, 335-347.
Ahren, Bo "Dipeptidyl Peptidase-4 Inhibitors" (2007) Diabetes Care, vol. 30, No. 6, 1344-1350.
Ahren, Bo et al. "Twelve- and 52-Week Efficacy of the Dipeptidyl Peptidase IV Inhibitor LAF237 in Metformin-Treated Patients with Type 2 Diabetes" (2004) Diabetes Care, vol. 27, No. 12, 2874-2880.
Aires, Ines et al. "BI-10773, a sodium-glucose cotransporter 2 inhibitor for the potential oral treatment of type 2 diabetes mellitus" (2010) Current Opinion in Investigational Drugs, vol. 11 (10), pp. 1182-1190.
American Diabetes Association "Consensus Development Conference on Antipyschotic Drugs and Obesity and Diabetes" (2004) Diabetes Care, vol. 27, No. 2, pp. 596-601.
American Diabetes Association "Diagnosis and Classification of Diabetes Mellitus" Diabetes Care, vol. 33, Supplement 1, Jan. 2010. pp. S62-S69.
American Diabetes Association "Standards of Medical Care in Diabetes—2009" vol. 32, Supplement 1, S13-61.
Anonymous "Efficacy and Safety of Empagliflozin (BI 10773) in Patients with Type 2 Diabetes and Renal Impairment" Jan. 8, 2013, XP055120166, www.clinicaltrials.gov/ct2/show/study/NCT01164501?term=empagliflozin&rank=26.
Anonymous "Prevalence of Chronic Kidney Disease and Associated Risk Factors—United States, 1999-2004", Mar. 2, 2007, XP055119515, http://www.cdc.gov/mmwr/preview/mmwrhtml/mm5608a2.htm.
Anonymous, "Composition with a High Drug Load of Empagliflozin" Feb. 26, 2016, 3 pgs.
Ashiya, Mona et al. "Non-insulin therapies for type 2 diabetes" (2007) Nature Reviews, Drug Discovery vol. 6, 777-778.
Assaly, Rana et al. "Added Benefit of Empagliflozin: Improvement of Erectile Dysfunction in Diabetic Type 2 Rats" (2015) XP-002758690, AN: PREV201500747898; 2 pgs.
Assaly, Rana et al. "The Favorable Effect of Empagliflozin on Erectile Function in an Experimental Model of Type 2 Diabetes" (2018) The Journal of Sexual Medicine, 1-11.

(56) References Cited

OTHER PUBLICATIONS

Ault Addison, "Techniques and experiments for organic chemistry" University Science Books, 1998, pp. 59-60.
Aulton, Michael E. "Pharmaceutics, The Science of Dosage Form Design" (2002) 2nd Edition, 404-409.
Baati, Rachid et al. "A Convenient Synthesis of 2-Tetrahydrofuranyl Ethers" (2000) Organic Letters, vol. 2, No. 4, 485-487.
Baggio, Laurie L. et al. "Biology of Incretins: GLP-1 and GIP" Gastroenterology (2007) vol. 132, 2131-2157.
Bailey, Clifford J. "Renal Glucose Reabsorption Inhibitors to Treat Diabetes" (2011) Trends in Pharmacological Sciences, vol. 32, No. 2, 63-71.
Bailey, Clifford J et al. "Diabetes therapies in renal impairment" The British Journal of Diabetes and Vascular Disease, (2012) vol. 12, Issue 4, 167-171.
Banker, Gilbert S. et al. "Modern Pharmaceutics, Third Edition, Revised and Expanded" (1996) Marcel Dekker, p. 596.
Baptista, Trino et al. "Pharmacological Management of Atypical Antipsychotic-Induced Weight Gain" (2008) CNS Drugs, 22, 6, pp. 478-495.
Barnett, Anthony H. et al. "Efficacy and safety of empagliflozin added to existing antidiabetes treatments in patients with type 2 diabetes and chronic kidney disease: a randomised, double-blind, placebo-controlled trial" The Lancet, (2014) vol. 2, pp. 369-384.
Baron, Kyle T. et al. "Population Pharmacokinetics and Exposure-Response (Efficacy and Safety/Tolerability) of Empagliflozin in Patients with Type 2 Diabetes" (2016) Diabetes Ther, 7: 455-471.
Basu, Ansu et al. "New Treatment Options for Erectile Dysfunction in Patients with Diabetes Mellitus" (2004) Drugs, 64 (23), 2667-2688.
Bauer, Kurt H. et al. "Pharmazeutische Technologie" (1993) p. 293.
Benhaddou, Rachida., et al; Tetra-n-Propylammonium Tetra-Oxoruthenate(VII): A Reagent of Choice for the Oxidation of Diversely Protected Glycopyranoses and Glycofuranoses to Lactones; Carbohydrate Research (1994) vol. 260 pp. 243-250.
Bloomgarden, Zachary T. "Diabetes Treatment" Diabetes Care, (Mar. 2009) vol. 32, No. 3 pp. e25-30.
Boards of Appeal of the European Patent Office, "Method of administering bisphosphonates" (2017) Application No. 05012711.7, EPA form 3030, 43 pgs "Web Publication".
Boehringer Ingelheim "Boehringer Ingelheim and Eli Lilly and Company announce positive top-line pivotal Phase III data results for empagliflozin*" (2013) 5 pgs.
Boehringer Ingelheim, "Clinical Study Synopsis for Public Disclosure, BI Trial No. 1245.10 Synopsis" May 15, 2014, 21 pgs.
Boehringer Ingelheim, "Clinical Study Synopsis for Public Disclosure, BI Trial No. 1245.12 Synopsis" (2011) 8 pgs.
Boehringer Ingelheim, "Clinical Study Synopsis for Public Disclosure, BI Trial No. 1245.19 Synopsis" May 15, 2014, 9 pgs.
Boehringer Ingelheim, "Clinical Study Synopsis for Public Disclosure, BI Trial No. 1245.23 Synopsis" May 15, 2014, 17 pgs.
Boyda, Heidi N et al. "Preclinical models of antipsychotic drug-induced metabolic side effects" (2010) Trends in Pharmacological Sciences vol. 31, pp. 484-497.
Brazg, R et al. "Effect of Adding MK-0431 to Ongoing Metformin Therapy in Type 2" (2005) Diabetes, vol. 54, Suppl. 1, A3.
Bristol-Myers Squibb Company, Label "Glucophage (metformin hydrochloride) Tablets, Glucophage XR (metformin hydrochloride) Extended-Release Tablets" Apr. 2017, 35 pgs.
British National Formulary, (2008) 358-359.
Buhler, Volker "Kollidon ® Polyvinylpyrrolidone excipients for the pharmaceutical industry" 9th revised edition, Mar. 2008, 1-331.
Busch, Frank R. et al. "Grignard Reagents—Industrial Applications and Strategy", Grignard Reagents, New Developments, John Wiley & Sons Ltd, copyright (2000), pp. 165-183.
Buysschaert, M. "Empagliflozin (Jardiance®) A Novel Hypoglycemic Agent in the Treatment of Type 2 Diabetes, Also Reduces Cardiovascular Risk: Analysis of a Princeps Study" (2015) Louvain Med 134(8), 403-408.

Byrn, Stephen et al. "Pharmaceutical Solids: A Strategic Approach to Regulatory Considerations" Pharmaceutical Research, vol. 12, No. 7, (1995) pp. 945-954.
Caira, Mino R. "Crystalline Polymorphism of Organic Compounds" (1998) Topics in Current Chemistry, vol. 198, 164-208.
Campbell, R. Keith "Rationale for Dipeptidyl Peptidase 4 Inhibitors: A New Class of Oral Agents for the Treatment of Type 2 Diabetes Mellitus" (2007) The Annals of Pharmacotherapy, vol. 41, 51-60.
Cartledge, JJ et al. "Endothelial and neuronal-derived nitric oxide mediated relaxation of corpus cavernosal smooth muscle in a rat, in vitro, model of erectile function" (2000) International Journal of Impotence Research, vol. 12, 213-221.
Castelhano, Arlindo L. et al. "Reactions of an Electrophilic Glycine Cation Equivalent With Grignard Reagents a Simple Synthesis of β,g-Unsaturated Amino Acids" (1986) Tetrahedron Letters, vol. 27, No. 22, pp. 2435-2438.
Cernea Simona, et al. "β-Cell Protection and Therapy for Latent Autoimmune Diabetes in Adults" Diabetes Care (2009) vol. 32, Supplement 2, pp. S246-S252.
Cetrone, Michela et al. "Effects of the antidiabetic drugs on the age-related atrophy and sarcopenia associated with diabetes type II" Current Diabetes Reviews (2014) vol. 10, No. 4, pp. 231-237.
Chen, L. H. et al. "Inhibition of the sodium glucose co-transporter-2: its beneficial action and potential combination therapy for type 2 diabetes mellitus" Diabetes, Obesity and Metabolism, (2013) vol. 15, pp. 392-402.
Chen, Lu-Lu "1000 questions about endocrine metabolic disease" Hubei Changjiang Publishing Group, Aug. 2006, ISBN 7-5352-3595-6, 3 pages.
Cherney, David et al. "The effect of sodium glucose cotransporter 2 inhibition with empagliflozin on microalbuminuria and macroalbuminuria in patients with type 2 diabetes" (2016) Diabetologia, 11 pgs.
Cherney, David Z.I. et al. "Pooled analysis of Phase III trials indicate contrasting influences of renal function on blood pressure, body weight, and HbA1c reductions with empagliflozin" (2017) Kidney International, 1-14.
Cherney, David Z.I. et al. "Renal Hemodynamic Effect of Sodium-Glucose Cotransporter 2 Inhibition in Patients with Type 1 Diabetes Mellitus" Circulation, (2014) V 129, pp. 587-597.
Cherney, David Z.I. et al. "The effect of empagliflozin on arterial stiffness and heart rate variability in subjects with uncomplicated type 1 diabetes mellitus" (2014) Cardiovascular Diabetology, 13:28, 8 pgs.
Chow, Francis CC, et al. "Challenges in achieving optimal glycemic control in type 2 diabetes patients with declining renal function: The Southeast Asia perspective" Journal of Diabetes Investigation, (2012) vol. 3, Issue 6, pp. 481-489.
Chyan, Yau-Jan, et al. "Dipeptidyl Peptidase-IV Inhibitors: An Evolving Treatment for Tyep 2 Diabetes from the Incretin Concept" (2007) Recent Patents on Endocrine, Metabolic & Immune Drug Discovery, vol. 1, No. 1, 15-24.
Clinical Trials: NCT00328172 "Efficacy and Safety of 3 Doses of BI1356 (Linagliptin) in Type 2 Diabetes Patients" Sponsor: Boehringer Ingelheim, Last Update Posted Mar. 14, 2014, 4 pgs.
Clinical Trials: NCT00554450 "Renal Impairment in Type 2 Diabetic Subjects" Sponsor: AstraZeneca, Last Update Posted Oct. 17, 2016, 5 pgs.
Clinical Trials: NCT01011868 "Efficacy and Safety of BI 10773 in Combination with Insulin in Patients with Type 2 Diabetes" Sponsor: Boehringer Ingelheim Pharmaceuticals, Oct. 18, 2010, 3 pgs.
Clinical Trials: NCT01064414 "An Efficacy, Safety and Tolerability Stude of Canagliflozin in Patients with Type 2 Diabetes Mellitus who have Moderate Renal Impairment" Sponsor: Janssen Research & Development LLC, Last Update Posted Aug. 14, 2013, 7 pgs.
Clinical Trials: NCT01131676. "BI 10773 Cardiovascular Outcome Event Trail in Type 2 Diabetes Mellitus Patients" Sponsor: Boehringer Ingelheim Pharmaceuticals, Updated date: Mar. 7, 2012. 5 pgs.
Clinical Trials: NCT01131676. "BI 10773 Cardiovascular Outcome Event Trail in Type 2 Diabetes Mellitus Patients" Sponsor: Boehringer Ingelheim Pharmaceuticals, Updated date: May 26, 2010. 4 pgs.

(56) References Cited

OTHER PUBLICATIONS

Clinical Trials: NCT01131676. "BI 10773 Cardiovascular Outcome Event Trail in Type 2 Diabetes Mellitus Patients" Sponsor: Boehringer Ingelheim Pharmaceuticals, Updated date: Nov. 14, 2012. 4 pgs.
Clinical Trials: NCT01164501 "Efficacy and Safety of BI 10773 in Patients with Type 2 Diabetes and Renal Impairment" Sponsor: Boehringer Ingelheim Pharmaceuticals, Jul. 15, 2010, 4 pgs.
Clinical Trials: NCT01164501 "Efficacy and Safety of BI 10773 in Patients with Type 2 Diabetes and Renal Impairment" Sponsor: Boehringer Ingelheim Pharmaceuticals, Last Update Posted: Jun. 16, 2014, 6 pgs.
Clinical Trials: NCT01164501 "Efficacy and Safety of BI 10773 in Patients with Type 2 Diabetes and Renal Impairment" Sponsor: Boehringer Ingelheim Pharmaceuticals, Mar. 7, 2012, 3 pgs.
Clinical Trials: NCT01164501 "History of Changes for Study: NCT01164501, Efficacy and Safety of Empagliflozin (BI 10773) in Patients with Type 2 Diabetes and Renal Impairment" Sponsor: Boehringer Ingelheim, Lastest version Jan. 8, 2013, 14 pgs "Web-Publication".
Clinical Trials: NCT01164501 "History of Changes for Study: NCT01164501, Efficacy and Safety of Empagliflozin (BI 10773) in Patients with Type 2 Diabetes and Renal Impairment" Sponsor: Boehringer Ingelheim, Lastest version May 16, 2014, 14 pgs.
Clinical Trials: NCT01164501 "History of Changes for Study: NCT01164501, Efficacy and Safety of Empagliflozin (BI 10773) in Patients with Type 2 Diabetes and Renal Impairment" Sponsor: Boehringer Ingelheim, Lastest version May 16, 2014, 7 pgs.
Clinical Trials: NCT01167881. "Efficacy and Safety of Empagliflozin (BI 10773) With Metformin in Patients with Type 2 Diabetes" Sponsor: Boehringer Ingelheim Pharmaceuticals, Updated Date: Apr. 3, 2013, 4 pgs.
Clinical Trials: NCT01210001 "Efficacy and Safety of Empagliflozin (BI 10773) in Type 2 Diabetes Patients on a Background of Pioglitazone Alone or with Metformin" Sponsor: Boehringer Ingelheim, Last Update Posted Jun. 17, 2014, 7 pgs.
Clinical Trials: NCT01422876 "Efficacy and Safety of Empagliflozin (BI 10773) / Linagliptin (BI 1356) Fixed Dose Dombination in Treatment naive and Metformin Treated Type 2 Diabetes Patients" Sponsor: Boehringer Ingelheim Pharmaceuticals, Apr. 1, 2015, 4 pgs.
Clinical Trials: NCT01734785 "History of Changes for Study: NCT01734785, Safety and Efficacy of the Combination of Empagliflozin and Linaglitin Compared to Linagliptin Alone Over 24 Weeks in Patients with Type 2 Diabetes" Sponsor Boehringer Ingelheim, Lastest version Jun. 9, 2016, 15 pgs.
Clinical Trials: NCT01778049 "History of Changes for Study: NCT01778049, Linagliptin as Add on Therapy to Empagliflozin 10mg or 25mg with Background Metformin in Patient with Type 2 Diabetes" Sponsor: Boehringer Ingelheim, Lastest version Mar. 4, 2016, 15 pgs.
Clinical Trials: NCT01778049 "Linagliptin as Add on Therapy to Empagliflozin 10mg or 25mg with Background Metformin in Patient with Type 2 Diabetes" Sponsor: Boehringer Ingelheim, Last update posted Apr. 4, 2016, 7 pgs.
Clinical trials: NCT01778049 "Linagliptin as Add on Therapy to Empagliflozin 10mg or 25mg with Background Metformin in Patient with Type 2 Diabetes" Sponsor: Boehringer Ingelheim, Last update posted Jan. 29, 2013, 7 pgs "Web Publication".
Clinical Trials: NCT01811953 "History of Changes for Study: NCT01811953, Equivalence of Resorption of Empagliflozin/Metformin Administered as Combination Tablet Compared With Empagliflozin/Metfomnin as Single Tablets Administered Together" Sponsor: Boehringer Ingelheim, Lastest version Jun. 26, 2015, 6 pgs.
Clinical Trials: NCT01907113 "History of Changes for Study: NCT01907113, Pharmacokinetics, Pharmacodynamics, Safety and Tolerability of BI 10773 in Type II Diabetes Patients with Different Degrees of Renal Impairment" Sponsor Boehringer Ingelheim, Lastest version Jul. 11, 2014, 6 pgs.
Clinical Trials: NCT01907113 "History of Changes for Study: NCT01907113, Pharmacokinetics, Pharmacodynamics, Safety and Tolerability of BI 10773 in Type II Diabetes Patients with Different Degrees of Renal Impairment" Sponsor Boehringer Ingelheim, Lastest version Jul. 22, 2013, 6 pgs "Web Publication".
Colorcon; Opadry II Aqueous Film Coating; http://www.colorcon.com/products-fomnulation/all-products/film-coatings/immediate-release/opadry-II ; Dec. 31, 2015.
Crepaldi, G. et al. "Dipeptidyl peptidase 4 (DPP-4) inhibitors and their role in Type 2 diabetes management" (2007) J. Endocrinol Invest, 30, 610-614.
Deacon, Carolyn F. "Perspectives in Diabetes Therapeutic Strategies Based on Glucagon-Like Peptide 1" Diabetes, (2004) vol. 53 pp. 2181-2189.
Defronzo, Ralph A. et al. "Combination of Empagliflozin and Linagliptin as Second-Line Therapy in Subjects with Type 2 Diabetes Inadequately Controlled on Metformin" (2015) Diabetes Care, 38, 384-393.
Diabetes Mellitus, Merck Manual Online Edition, (retrieved Sep. 13, 2011) http://www.merckmanuals.com/professional/endocrine_and_metabolic_disorders/diabetes_mellitus_and_disorders_of_carbohydrate_metabolism/diabetes_mellitus_dm.html#v987998. Revision Jun. 2008.
Dohle, Wolfgang., et al; Copper-Mediated Cross-Coupling of Functionalized Arylmagnesium Reagents with Functionalized Alkyl and Benzylic Halides; Organic Letters (2001) vol. 3 No. 18 pp. 2871-2873.
Dokken, Betsy "The Kidney as a Treatment Target for Type 2 Diabetes" (2012) Diabetes Spectrum, vol. 25, No. 1, 29-36.
Drucker, Daniel J. et al. "Glucagon-like peptide I stimulates insulin gene expression and increases cyclic AMP levels in a rat islet cell line" (1987) Proc. Natl. Acad. Sci. USA, vol. 84, 3434-3438.
Drug Watch "Type 2 Diabetes Mellitus" Formulary vol. 43 Aug. 2008 p. 304.
DrugBank entries for Linagliptin (Accession No. DB08882), Sitagliptin (Accession No. DB01261) and Vitagliptin (Accession No. DB04876), downloaded Jan. 30, 2018, 12 pgs.
Drugbank. Metformin. Accession No. DB00331 (APRD01099) https://www.drugbank.ca/drugs/DB00331. Drug created on Jun. 13, 2005/Updated on May 9, 2017.
Du, Dong Hui "Challenges faced in primary care of diabetic patients with renal insufficiency" Diabetes World, Clinical Periodical, Nov. 2012, vol. 6, No. 11, 498-502.
Eade, Ronald E. "Extractives of Australian Timbers. XV* THe Synthesis of 7,4'-Di-O-methylbayin" (1975) Austr. J. Chemistry, vol. 28, pp. 2011-2018.
Eli Lilly "US FDA grants Fast Track designation to Jardiance® (empagliflozin) to improve outcomes following a heart attack" (2020) Lilly.com, News Release, 6 pgs.
Ekstrom, Nils et al. "Effectiveness and safety of metformin in 51675 patients with type 2 diabetes and different levels of renal function: a cohort study from the Swedish National Diabetes Register" (2012) BJM Open, 2, 10 pgs.
Eli Lilly "Boehringer Ingelheim and Eli Lilly and Company announce positive top-line pivotal Phase III data results for empagliflozin" Jan. 7, 2013, 3 pgs.
Eli Lilly, "Boehringer Ingelheim Pharmaceuticals, Inc. and Eli Lilly and Company to Feature 30 Presentations on Type 1 and Type 2 Diabetes at the 72nd American Diabetes Assoiation Sceintific Sessions" (2012) 4 pgs.
Weber, Ann E. "Dipeptidyl Peptidase IV Inhibitors for the Treatment of Diabetes" (2004) J. Med. Chem., 47, 4135-4141.
Websters Third New International Dictionary, Editor: GOVE, definition of prevent; 1963, 2 pgs.
Weinberg, Aviva E. et al. "Diabetes Severity, Metabolic Syndrome and the Risk of Erectile Dysfunction" (2013) International Society for Sexual Medicine 10:3, 3102-3109.
Wettergren, Andre et al. "Truncated GLP-1 (Proglucagon 78-107-Amide) Inhibits Gastric and Pancreatic Functions in Man" (1993) Digestive Diseases and Sciences, vol. 38, No. 4, 665-673.
Wielert-Badt, Susanne et al. "Probing the Conformation of the Sugar Transport Inhibitor Phlorizin by 2D-NMR, Molecular Dynamics Studies, and Pharmacophore Analysis" (2000) J. Med. Chem., vol. 43, 1692-1698.

(56) References Cited

OTHER PUBLICATIONS

Wielert-Badt, Susanne et al. "Single Molecule Recognition of Protein Binding Epitopes in Brush Border Membranes by Force Microscopy" (2002) Biophysical Journal, vol. 82, 2767-2774.

Woerle Hans-Juergen et al. "Safety and Efficacy of Empagliflozin as Monotherapy or Add-on to Metformin in a 78-Week Open-Lable Extension Study in Patients with Type 2 Diabetes" Presentation Abstract, 49-LB, (2012) 4 pg.

Wolff, Manfred E., et al., "Burger's Medicinal Chemistry and Drug Discovery, Fifth Edition, vol. 1, Principles and Practices", (1995) Wiley-lnterscience Publication pp. 975-977.

Woo, Vincent C. "Dapagliflozin: where does it fit in the treatment of type 2 diabetes" (2009) Expert Opinion on Pharmacotherapy, 10(15): 2527-2535.

Woo, Young Sup et al. "Blood pressure changes during clozapine or olanzapine treatment in Korean schizophrenic patients" (2009) The World Journal of Biological Psychiatry, vol. 10(4); pp. 420-425.

Wouters, Annelies, et al. "Synopsis: An Open-Label Study to Investigate the Absorption, Metabolism and Excretion of JNJ-28431754 in Healthy Male Subjects Following a Single Oral Dose Administration of C-JNJ-28431754" (2009) Clinical Study Report Synopisis, Protocol No. 28431754-NAP-1006, 5 pgs "Web Publication".

Wu, Ren-Rong et al. "Lifestyle Intervention and Metformin for Treatment of Antipsychotic-Induced Weight Gain, A Randomized Controlled Trial" Journal of American Medical Association (2008) V 299, pp. 185-193.

Xue, Song., et al; Zinc-mediated Synthesis of Alpha-C-Glycosided from 1,2-Anhydroglycosides; Synletters (2003) vol. 6 pp. 870-872.

Yale, J.F et al. "Efficacy and safety of canagliflozin in subjects with type 2 diabetes and chronic kidney disease" Diabetes, Obesity and Metabolism (2013) vol. 15, Abstract "Web Publication".

Yale, J.F. et al. "Efficacy and safety of canagliflozin in subjects with type 2 diabetes and chronic kidney disease" Diabetes, Obesity and Metabolism (2013) vol. 15, pp. 463-473.

Yale, J.F. et al. "Efficacy and safety of canagliflozin in subjects with type 2 diabetes and chronic kidney disease" Diabetes, Obesity and Metabolism (2013) vol. 15, pp. 463-473 (18 pgs) "Web Publication".

Yale, J.F. et al. "Efficacy and safety of canagliflozin in subjects with type 2 diabetes and chronic kidney disease" Diabetes, Obesity and Metabolism (2013) vol. 15, pp. 463-473 (22 pgs) "Web Publication".

Yale, J.F. et al. "Efficacy and safety of canagliflozin in subjects with type 2 diabetes and chronic kidney disease" Diabetes, Obesity and Metabolism (Mar. 2013) vol. 15, 24 pgs, [online], [retrieved on Sep. 6, 2018]. Retrieved from the Internet <URL: <https://onlinelibrary.wiley.com/doi/full/10.1111/dom.12090>>.

Yale, Jean-Francois et al. "Canagliflozin (CANA), a Sodium Glucose Co-Transporter 2 (SGLT2) Inhibitor, Improves Glycemia and is Well Tolerated in Type 2 Diabetes Mellitus (T2DM) Subjects with Moderate Renal Impairment" Presentation Abstract, 41-LB, (2012) 1 pg.

Yale, Jean-Francois et al. "Canagliflozin (CANA), a Sodium Glucose Co-Transporter 2 (SGLT2) Inhibitor, Improves Glycemia and is Well Tolerated in Type 2 Diabetes Mellitus (T2DM) Subjects with Moderate Renal Impairment" (2012) Canadian Journal of Diabetes, Abstract 139, S40-41.

Yale, Jean-Francois et al. "Canagliflozin, a Sodium Glucose Co-Transporter 2 Inhibitor, Improves Glycemia and Is Well Tolerated in Type 2 Diabetes Mellitus Subjects with Moderate Renal Impairment" Jun. 8, 2012, Poster presented at the 72nd Scientific Session of the American Diabetes Association, 2 pgs.

Yamada, Yuichiro et al. "Clinic: Careful Progress in the Field and new Therapeutic Methods" Medical Online, (2007) vol. 220, No. 13, pp. 1219-1221.

Yamout, Hala et al. "Efficacy and Safety of Canagliflozin in Patients with Type 2 Diabetes and Stage 3 Nephropathy" (2014) Am J Nephrol, 40: 64-74.

Yao, Chun-Hsu et al. "Discovery of Novel N-b-D-Xylosylindole Derivatives as Sodium-Dependent Glucose Cotransporter 2 (SGLT2) Inhibitors for the Management of Hyperglycemia in Diabetes" (2011) J. Med. Chem. vol. 54, pp. 166-178.

Young, Kerry Dooley "FDA panel rejects new empagliflozin indication for type 1 diabetes" (2019) Clinical Endocrinology News, 4 pgs.

Yuan, Yingjin. "Modern Pharmaceutical Technology", Chemical Industry Press, (2005) vol. 2, p. 75.

Zanoli, L. et al. "Sodium-Glucose Linked Transporter-2 Inhibitors in Chronic Kidney Disease" (2015) The Scientific World Journal, Article ID 317507, 6 pgs.

Zhang, L. et al. "Dapagliflozin treatment in patients with different stages of type 2 diabetes mellitus: effects on glycaemic control and body weight" Diabetes, Obesity and Metabolism (2010) vol. 12, No. 6, p. 510-515.

Zhang, Wen Bin et al. "Renal SGLT2 inhibitors: A novel type of oral antidiabetic drug" (2010) Progress in Physiological Sciences, vol. 41, No. 6, 453-460.

Zhang, Wenbin et al. "EGT1442, a potent and selective SGLT2 inhibitor, attenuates blood glucose and HbA1c levels in db/db mice an prolongs the survival of stroke-prone rats" (2011) Pharmacological Research, vol. 63, pp. 284-293.

Zheng, Tiesheng et al. "Clinical Biochemistry Experimental Diagnosis and Case Analysis" (2010) China Medical Science and Technology Press, 201001, p. 152.

Zimmermann, Grant R et al. "Multi-target therapeutics: when the whole is greater than the sum of the parts" (2007) Drug Discovery Today, vol. 12, 34-42.

Zinman, Bernard et al. "Empagliflozin, Cardiovascular Outcomes and Mortality in Type 2 Diabetes" (2015) The New England Journal of Medicine, 373:22 pp. 2117-2128.

Thomson, Scott C. et al. "Acute and chronic effects of SGLT2 blockade on glomerular and tubular function in the early diabetic rat" (2011) Am J Physiol Regul Integr Comp Physiol, V 302, pp. R75-R83.

Thornber, C.W. et al. "Isosterism and Molecular Modification in Drug Design" (1979) Imperial Chemical Industries Limited, Pharmaceuticals Division, Mereside, Alderley Park, Macclesfield, Cheshire, pp. 563-580.

Threlfall, Terry "Structural and Thermodynamic Explanations of Ostwald's Rule" Organic Process Research & Development (2003) vol. 7, pp. 1017-1027.

Torrance, Christopher J. et al. "Combinatorial chemoprevention of intestinal neoplasia" (2000) Nature Medicine, vol. 6, No. 8, 1024-1028.

Tsuchihashi-Makaya, Miyuki et al. "Characteristics and Outcomes of Hospitalized Patients with Heart Failure and Reduced vs Preserved Ejection Fraction" (2009) Circulation Journal, vol. 73, 1893-1900.

Tsujihara, Kenji et al. "Na+ -Glucose Cotransporter (SGLT) Inhibitors as Antidiabetic Agents. 4. Synthesis and Pharmacological Properties of 4'-Dehydroxyphlorizin Derivatives Substituted on the B Ring" J. Med. Chem. (1999) vol. 42, pp. 5311-5324.

Tsujihara, Kenji et al. "Na+ -Glucose Cotransporter Inhibitors as Antidiabetics. I. Synthesis and Pharmacological Properties of 4'Dehydroxyphlorizin Derivatives Based on a New Concept" (1996) Chem. Pharm. Bull. 44(6), 1174 1180.

Twigger, Simon N. "Meeting Report of Rats and Men: The Rat Genome and Comparative Genomics" Genome Biology (2004) vol. 5, Issue 3, Article 314, 2 pgs.

Tykwinski, Rik R; Evolution in the Palladium-Catalyzed Cross-Coupling of sp- and sp2-Hybridized Carbon Atoms; Angew Chemical International Edition (2003) vol. 42 pp. 1566-1568.

U.S. Appl. No. 12/892,310, filed Sep. 28, 2010. Inventor: Dirk Weber.

U.S. Appl. No. 12/892,326, filed Sep. 28, 2010. Inventor: Dirk Weber.

U.S. Appl. No. 12/894,385, filed Sep. 30,2010. Inventor: Peter Schneider.

U.S. Appl. No. 13/079,424, filed Apr. 4, 2011. Inventor: Matthias Eckhardt.

(56) References Cited

OTHER PUBLICATIONS

U.S. Appl. No. 13/287,216, filed Nov. 2, 2011. Inventor: Rolf Grempler.
U.S. Appl. No. 13/367,739, filed Feb. 7, 2012. Inventor: Thomas Klein.
U.S. Appl. No. 13/413,702, filed Mar. 7, 2012. Inventor: Masanori Ito.
U.S. Appl. No. 13/637,413, filed Sep. 26, 2012. Inventor: Rolf Grempler.
U.S. Appl. No. 13/693,239, filed Dec. 4, 2012. Inventor: Klaus Dugi.
U.S. Appl. No. 13/785,365, filed Mar. 5, 2013. Inventor: Masanori Ito.
U.S. Appl. No. 13/833,097, filed Mar. 15, 2013. Inventor: Eric Williams Mayoux.
U.S. Appl. No. 14/244,196, filed Apr. 3, 2014. Inventor: Uli Christian Broedl.
U.S. Appl. No. 14/244,208, filed Apr. 3, 2014. Inventor: Uli Christian Broedl.
U.S. Appl. No. 14/253,935, filed Apr. 16, 2014. Inventor: Uli Christian Broedl.
U.S. Appl. No. 15/918,477, filed Mar. 12, 2018. Inventor: Uli Christian Broedl.
U.S. Appl. No. 15/945,236, filed Apr. 4, 2018. Inventor: Uli Christian Broedl.
U.S. Appl. No. 12/545,175, filed Aug. 21, 2009, Inventor: Matthias Eckhardt.
Ueta, Kiichiro., et al.; Long-Term Treatment with the Na+ -Glucose Cotransporter Inhibitor T-1095 Causes Sustained Improvement in Hyperglycemia and Prevents Diabetic Neuropathy in Goto-Kakizaki Rats; Life Sciences (2005) vol. 76 pp. 2655-2668.
United States Pharmacopoeia, The National Formulary, (2005) USP 28, NF 23, p. 2711.
Unknown "Intensification of Development of SGLT inhibitor—New Alternative of Antidiabetic" Aug. 21, 2007; 2 pgs; http://www.yakuji.cojp/entry4100.html.
US Department of Health and Human Services, CDER, FDA, "Guideline for Submitting Supporting Documentation in Drug Applications for the Manufacture of Drug Substances" Feb. 1987, 48 pages.
US Department of Health and Human Services, FDA, Endocrinologic and Metabolic Drugs Advisory Committee; Notice of Meeting, Federal Register, vol. 76, No. 80, Apr. 26, 2011, 23324-23325.
US Department of Health and Human Services, FDA, "Guidance for Industry, Diabetes Mellitus—Evaluating Cardiovascular Risk in New Antidiabetic Therapies to Treat Type 2 Diabetes" Dec. 2008, 8 pages.
US Department of Health and Human Services, FDA, "Guidance for Industry, Pharmacokinetics in Patients with mpaired Renal Function—Study Design, Data Analysis, and Impact on Dosing and Labeling" May 1998, 19 pages.
US Department of Health and Human Services, FDA, Center for Drug Evaluation and Research "Application No. 204629Orig1s000 Summary Review (Jardiance)" 2014, 20 pages.
Uspto, U.S. Appl. No. 14/805,838, Third-party submission under 37 CFR 1.290 dated Dec. 12, 2016. 19 pgs.
Valentine, Virginia "The Role of the Kidney and Sodium-Glucose Cotransporter-2 Inhibition in Diabetes Management" (2012) Clinical Diabetes, vol. 30, No. 4, 151-155.
Valk, Harold W. de "DPP-4 Inhibitors and Combined Treatment in Type 2 Diabetes: Re-evaluation of Clinical Success and Safety" (2007) The Review of Diabetic Studies, vol. 4, No. 3, 126-133.
Vallon, Volker et al. "Glomerular Hyperfiltration in Experimental Diabetes Melliutes: Potential Role of Tubular Reabsorption" (1999) J. Am. Soc. Nephrol., V 10: pp. 2569-2576.
Vallon, Volker et al. "Knockout of Na-glucose transporter SGLT2 attenuates hyperglycemia and glomerular hyperfiltration but not kidney growth or injury in diabetes mellitus" (2012) Am J Physiol Renal Physiol, vol. 304, F156-F167.

Vallon, Volker et al. "SGLT2 inhibitor empagliflozin reduces renal growth and albuminuria in proportion to hyperglycemia and prevents glomerular hyperfiltration in diabetic Akita mice" (2013) Am J Physiol Renal Physiol, 306, F194-F204.
Veltkamp, Stephan A. et al. "[1127-P] The Effect of Renal Impairment on the Pharmacokinetics and Urinary Glucose Excretion of the SGLT2 Inhibitor ASP1941 in Type 2 Diabetes Mellitus Patients" Clinical Therapeutics/New Technology, A309-A310.
Wagman, Allan S et al. "Current Therapies and Emerging Targets for the Treatment of Diabetes" (2001) Current Pharmaceutical Design, vol. 7, No. 6, 417-450.
Wallace, Debra J., et al.; Cyclopropylboronic Acid: Synthesis and Suzuki Cross-Coupling Reactions Tetrahedron Letters (2002) vol. 43 pp. 6987-6990; Pergamon Press.
Wang et al., "Modern diagnosis and treatment of common cardiovascular diseases", Jul. 31, 2013, Shanxi Science and Technology Press, 1st Edition, p. 32 (English Abstract).
Wang Y et al.: "BI-1356. Dipeptidyl-peptidase IV inhibitor, antidiabetic agent" Drugs of the Future, Prous Science, ES,vol. 33, No. 6, Jun. 1, 2008, pp. 473-477.
Wang, Xiao-jun et al. "Efficient Synthesis of Empagliflozin, an Inhibitor of SGLT-2, Utilizing an AICI3-Promoted Silane Reduction of β-Glycopyranoside" (2014) American Chemical Society, vol. 16, 4090-4093.
Wanner, Christoph et al. "Empagliflozin and Clinical Outcomes in Patients with Type 2 Diabetes, Established Cardiovascular and Chronic Kidney Disease" (2017) Circulation, American Heart Association, 66 pgs.
Washburn, William N. "Dapagliflozin, A Selective SGLT2 Inhibitor for Treatment of Diabetes" (2015) Successful Drug Discovery, p. 87-112.
Washburn, William N. et al. "Differentiating sodium-glucose cotransporter-2 inhibitors in development for the treatment of type 2 diabetes mellitus" (2013) Expert Opinion on Investigational Drugs, 22:4, 463-486.
Lehmann, Ule et al. "Palladium-Catalyzed Cross-Coupling Reactions between Dihydropyranylindium Reagents and Aryl Halides, Synthesis of C-Aryl Glycals" Organic Letters, 2003, vol. 5, No. 14, pp. 2405-2408.
Levetan, Claresa "Oral antidiabetic agents in type 2 diabetes" (2007) Current Medical Research and Opinion, vol. 23, No. 4, 945-952.
Levey, Andrew S. et al. "Definition and classification of chronic kidney disease: A position statement from Kidney Disease: Improving Global Outcomes (KDIGO)" (2005) Kidney International, vol. 67, 2089-2100.
Lewin, Andrew et al "Initial Combination of Empagliflozin and Linagliptin in Subjects with Type 2 Diabetes" (2015) Diabetes Care, vol. 38, 394-402.
Li, T, et al. "Lack of Pharmacokinetic Interaction between Dapagliflozin and Pioglitazone in Healthy Subjects" Journal of Clinical Pharmacology, (2009) vol. 49, No. 9, p. 1093.
Li, Yazhou, et al. "Glucagon-like Peptide-1 Receptor Signaling Modulates b Cell Apoptosis" (2003) The Journal of Biological Chemistry, vol. 278, No. 1, 471-478.
Lieberman, Herbert A. et al. "Pharmaceutical Dosage Forms: Tablets, vol. 1" (1989) pp. 5-6.
Lieberman, Joseph A. "Metabolic Changes Associated with Antipsychotic Use" Prim Care Companion J Cline Psychiatry (2004) 6, pp. 8-13.
Lipska, Kasia J. et al. "Use of Metformin in the Setting of Mild-to-Moderate Renal Insufficiency" (2011) Diabetes Care, vol. 34, 1431-1437.
Lipworth, Brian J. "Clinical pharmacology of b3-adrenoceptors" Br J Clin Pharmacol (1996) pp. 291-300.
List, James F. et al. "Glucose dynamics and mechanistic implications of SGLT2 inhibitors in animals and humans" (2011) Kidney International, 79, Suppl 120, S20-S27.
Liu, Sheng et al. "Chemically induced (*Streptozotocin alloxan*) diabetes mellitus in dogs" (2000) Bull Hunan Med University, vol. 25, No. 2, pp. 125-128 (English Translation).
Lu, Jiangqian et al. "Chapter 8, Treatment of heart failure iwth clinical conditions, Section II Treatment of heart failure compli-

(56) References Cited

OTHER PUBLICATIONS cated by arrhythmia" Feb. 28, 2015, Practical Handbook of Diagnosis and Treatment of Heart Failure, People's Military Medical Publishing House 1st Edition, p. 177 (English Abstract).
Luna, Beatriz et al. "Oral Agents in the Management of Type 2 Diabetes Mellitus" (2001) American Family Physician, vol. 63, No. 9, 1747-1756.
Maayan, Lawrence et al. "Effectiveness of Medications Used to Attenuate Antipsychotic-Related Weight Gain and Metabolic Antipsychotic-Related Weight Gain and Metabolic Abnormalities: A Systematic Review and Meta-Analysis" (2010) Neuropsychopharmacology, vol. 35, pp. 1520-1530.
Macha, S. et al. "Pharmacokinetics, pharmacodynamics and safety of empagliflozin, a sodium glucose cotransporter 2 (SGLT2) inhibitor, in subjects with renal impairment" (2014) Diabetes, Obesity and Metabolism, 16: 215-222.
Macha, Sreeraj et al. "Pharmacokinetics of empagliflozin, a sodium glucose cotransporter 2 (SGLT2) inhibitor, and metformin following co-administration in healthy volunteers" (2013) International Journal of Clinical Pharmacology and Therapeutics, vol. 51, No. 2, pp. 132-140.
Maeda, Yasutaka et al. "Oxidative Stress" (2010) Nippon Rinsho, vol. 68, No. 5, 814-818.
Magee, G.M. et al. "Is hyperfiltration associated with the future risk of developing diabetic nephropathy? A meta-analysis" Diabetologia (2009) 52: pp. 691-697.
Marchetti, Piero et al. "Pancreatic Islets from Type 2 Diabetic Patients Have Functional Defects and Increased Apoptosis that are Ameliorated by Metformin" The Journal of Clinical Endocrinology & Metabolism, (2004) vol. 89,(11) pp. 5535-5541.
Matsuyama, Tatsuo et al. "Glucagon-like peptide-1 (7-36 amide): a potent glucagonostatic and insulinotropic hormone" Diabetes Research and Clincial Practice (1988) 5, 281-284.
Matzke, Gary R. et al. "Drug dosing consideration in patients with acute and chronic kidney disease—a clinical update from Kidney Disease: Improving Global Outcomes (KDIGO)" (2011) Kidney International, vol. 80, 1122-1137.
McGill, Janet B. et al. "Long-Term Efficacy and Safety of Linagliptin in Patients with Type 2 Diabetes and Severe Renal Impairment, A 1-year randomized, double-blind, placebo-controlled study" (2013) Diabetes Care, vol. 36, 237-244.
McHale, Mary "Grignard Reaction" Connexions module: m15245, (2007) pp. 1-18.
McKinney, James D. et al. "The Practice of Structure Activity Relationships (SAR) in Toxicology" (2000) Toxicological Sciences, vol. 56, 8-17.
McLaughlin, Mark., et al; Suzuki-Miyaura Cross-Coupling of Benzylic Phospahates with Arylboronic Acids; Organic Letters (2005) vol. 7 No. 22 pp. 4875-4878.
McMaster University, Chem2006 Lab Manual, 1997/98, Expt 1, Part B, pp. 1-9.
Mende, Christian" Management of Chronic Kidney Disease: The Relationship between Serum Uric Acid and the Development of Nephropathy" (2015) Adv. Ther. 32, 1177-1191.
Meng, Wei et al. "Discovery of Dapagliflozin: A Potent, Selective Renal Sodium-Dependent Glucose Cotransporter 2 (SGLT2) Inhibitor for the Treatment of Type 2 Diabetes" J. Med Chem. (2008) vol. 51, pp. 1145-1149.
Merck Manual Online Edition, "Diabetes Mellitus" http://www.merckmanuals.com/professional/endocrine_and_metabolic_disorders/diabetes_mellitus_and_disorders of carbohyrate_metabolism/diabetes_mellitus_dm.html#/v987998. last revision Jun. 2008 by Preeti Kishore M.D.
Merriam-Webster's Collegiate Dictionary,definition of prevent, published 1998 by Merriam-Webster INC. p. 924.
Meyer, Timothy W. "Tubular injury in glomerular disease" (2003) Kidney International, vol. 63, p. 774-787.
Miller, Del D. "Review and Management of Clozapine Side Effects" (2000) J Clinc Psychiatry, 61 (Suppl 8) pp. 14-17.
Miyagawa, Junichiro et al. "Combined use between incretin-related meidcations and other medications" (2010) Diagnosis and Treatment, vol. 98, No. 3, 423-436.
Mogensen, Carl Erik "Perspectives in Diabetes Prediction of Clinical Diabetic Nephropathy in IDDM Patients Alternatives to Microalbuminuria?" Diabetes (1990) vol. 39, pp. 761-767.
Mojsov, Svetlana "Insulinotropin: Glucagon-like Peptide I (7-37) Co-encoded in the Glucagon Gene Is a Potent Stimulator of Insulin Release in the Perfused Rat Pancreas" J. Clin. Invest. (1987) vol. 79, 616-619.
Mooradian, Arsharg D. et al. "Narrative Review: A Rational Approach to Starting Insulin Therapy" (2006) Annals of Internal Medicine, vol. 145, pp. 125-134.
Munir, Kashif et al. "Differential pharmacology and clinical utility of empagliflozin in type 2 diabetes" (2016) Clinical Pharmacology: Advances and Applications, vol. 8, 19-34.
Murray, Michael "Encyclopedia of Nurtritional Supplements" (1996) pp. 283-287.
Musicki, B. et al. "Endothelial dysfunction in diabetic erectile dysfunction" (2007) International Journal of Impotence Research, vol. 19, 129-138.
Nair, S. et al. "From history to reality: sodium glucose co-transporter 2 inhibitors—a novel therapy for type 2 diabetes mellitus" (2010) Pract Diab Int, vol. 27, No. 7, pp. 311-316.
Nathan, D.M. et al. "Medical management of hyperglycaemia in type 2 diabetes mellitus: a consensus algorithm for the initiation and adjustment of therapy" Diabetologia (2009) 52, 17-30.
Nathan, David M. et al. "Management of Hyperglycemia in Type 2 Diabetes: A Consensus Algorithm for the Initiation and Adjustment of Therapy" (2006) Diabetes Care, vol. 29, No. 8, 1963-1972.
National Institute for Health Research, Horizon Scanning Centre, "Empagliflozin for type 2 diabetes mellitus" Apr. 2012, 10 pgs.
National Kidney Foundation "Mild-to-moderate Chronic Kidney Disease" (2010) 5 pgs www.patient.co.uk.
National Kidney Foundation, "Clinical Practice Guidelines, For Chronic Kidney Disease: Evaluation, Classification and Stratification" (2002) 356 pgs.
Nauck, Michael A. et al. "Cardiovascular Actions and Clincial Outcomes with Glucagon-Like Peptide-1 Receptor Agonistsand Dipeptidyl Peptidase-4 Inhibitors" Circulation (2017) vol. 136, 849-870.
Neamati, Ouri., et al;, "Depsides and Depsidones as Inhibiton of HIV-1 Integrase: Dimvery of Novel Inhibitors Through 3D Database Searclung", J. Med Chem., 1997, vol. 40, pp. 942-951.
Negishi, Ei-ichi, et al. "Selective Carbon-Carbon Bond Formation via Transition Metal Catalysis. 3. A Highly Selective Synthesis of Unsymmetrical Biaryls and Diarylmethanes by the Nickel- or Palladium- Catalyzed Reaction of Aryl- and Benzylzinc Derivatives with Aryl Halides" (1977) Journal of Organic Chemistry, V 42, No. 10, 1821-1823.
Nobre, Sabrina M., et al; Synthesis of Diarylmethane Derivatives from Pd-Catalyzed Cross-Coupling Reactions of Benzylic Halides with Arylboronic Acids; Tetrahedron Letters (2004) vol. 45 8225-8228.
Non Final Office Action dated Apr. 2, 2008 from U.S. Appl. No. 11/674,839, filed Feb. 14, 2007.
Non Final Office Action dated Apr. 2, 2008 from U.S. Appl. No. 11/742,612, filed May 1, 2007.
Non-Final Office Action dated Jun. 24, 2008 from U.S. Appl. No. 11/406,971, filed Apr. 19, 2006.
Non-Final Office Action dated Jun. 5, 2008 from U.S. Appl. No. 11/408,899, filed Apr. 21, 2006.
Non-Final Office Action dated Mar. 10, 2017 from U.S. Appl. No. 14/855,576, filed Sep. 16, 2015.
Non-Final Office Action dated May 8, 2008 from U.S. Appl. No. 11/359,846, filed Feb. 22, 2006.
Notice of Allowance and Fee(s) Due dated Jan. 13, 2009 from U.S. Appl. No. 11/304,284, filed Dec. 15, 2005.
Notice of Allowance and Fee(s) Due dated Dec. 30, 2008 from U.S. Appl. No. 11/674,839, filed Feb. 14, 2007.
Notice of Allowance and Fee(s) Due dated Feb. 3, 2009 from U.S. Appl. No. 11/359,846, filed Feb. 22, 2006.

(56) References Cited

OTHER PUBLICATIONS

Notice of Allowance and Fee(s) Due dated Jan. 2, 2009 from U.S. Appl. No. 11/742,612, filed May 1, 2007.
Office Action dated Mar. 10, 2017, U.S. Appl. No. 14/918,713, filed Oct. 21, 2015, first named inventor Uli Christian Broedl.
Oku, Akira., et al; T-1095, An Inhibitor or renal Na+ -Glucose Cotransporters, May Provide a Novel Approach to Treating Diabetes; Diabetes (1999) vol. 48 pp. 1794-1800.
Opposition to corresponding European Patent EP2981271 B1 (Application 14715578.2); "Summons To Attend Oral Proceedings and preliminary opinion of the Opposition Division—List of References" (2020) 27 pgs.
Opposition to corresponding European Patent EP2981271 B1 (Application 14715578.2); Declaration of Bernd Fussman and Policy on Transparency and Publication of Clinical Study Data submitted by the Patent Proprietor (2020) 6 pgs.
Opposition to corresponding European Patent EP2981271 B1 (Application 14715578.2); Notice of Opposition, Opponent: Alfred E. Tiefenbacher (Aug. 16, 2019) 20 pgs.
Opposition to corresponding European Patent EP2981271 B1 (Application 14715578.2); Notice of Opposition, Opponent: Egis Gyogyszergyar Zartkoruen Mukodo Reszvenytarsasag (Aug. 22, 2019) 25 pgs.
Opposition to corresponding European Patent EP2981271 B1 (Application 14715578.2); Notice of Opposition, Opponent: Generics (U.K) Limited, (Aug. 22, 2019) 25 pgs.
Opposition to corresponding European Patent EP2981271 B1 (Application 14715578.2); Notice of Opposition, Opponent: Krka, d.d., Novo Mesto (Aug. 12, 2019) 28 pgs.
Opposition to corresponding European Patent EP2981271 B1 (Application 14715578.2); Notice of Opposition, Opponent: Richard Gillard (Aug. 22, 2019) 31 pgs.
Opposition to corresponding European Patent EP2981271 B1 (Application 14715578.2); Notice of Opposition, Opponent: STADA Arzneimittel AG (Aug. 22, 2019) 24 pgs.
Opposition to corresponding European Patent EP2981271 B1 (Application 14715578.2); Notice of Opposition, Opponent: Teva Pharmaceutical Industries Ltd. (Aug. 22, 2019) 11 pgs.
Opposition to corresponding European Patent EP2981271 B1 (Application 14715578.2); Notice of Opposition, Opponent: Zaklady Farmaceutyczne Polpharma S.A. (Aug. 22, 2019) 31 pgs.
Opposition to corresponding European Patent EP2981271 B1 (Application 14715578.2); Observation to the summons and the Opposition Division's preliminary opinion submitted by the Patent Proprietor (2020) 39 pgs.
Osorio, Horacio et al. "Sodium-Glucose Cotransporter Inhibition Prevents Oxidative Stress in the Kidney of Diabetic Rats" (2012) Oxidative Medicine and Cellular Longevity, vol. 2012, Article ID 542042, 7 pgs.
Pan, Feng et al. "Intracavernosal Pressure Recording to Evaluate Erectile Function in Rodents" (2018) Journal of Visualized Experiments, vol. 136, e56798, 1-7.
Pan, Qi et al. "Changes of streptomycin induced type I diabetes mellitus in serum oxygen free radicals and antioxidant function thereof in rats" (2006) Journal of China, Prescription Drug, vol. 56, pp. 65-66.
Panchapakesan, Usha et al. Effects of SGLT2 Inhibition in Human Kidney Proximal Tubular Cells—Renoprotection in Diabetic Nephropathy?' PLOS one, (2013) vol. 8, Issue 2, e54442, 8 pgs.
Patane, Giovanni et al. "Metformin Restores Insulin Secretion Altered by Chronic Exposure to Free Fatty Acids or High Glucose, A Direct Metformin Effect on Pancreatic b-Cells" (2000) Diabetes, vol. 49, pp. 735-740.
Patil, Basanagouda M. et al. "Elevation of systolic blood pressure in an animal model of olanzapine induced weight gain" (2006) European Journal of Pharmacology, vol. 551, pp. 112-115.
Perez Lopez, G. et al. "Sodium-glucose cotransporter 2 (SGLT2) inhibitors: from renal glycosuria to the treatment of type 2 diabetes mellitus" (2010) Nefrologia, 30(6) 618-625.

Perkins, Bruce A. et al. "Sodium-Glucose Cotransporter 2 Inhibition and Glycemic Control in Type 1 Diabetes: Results of an 8-Week Open-Label Proof-of-Concept Trial" (2014) Diabetes Care, vol. 37, pp. 1480-1483.
Perner, Richard J., et al; 5,6,7-Trisubstituted 4-Aminopyrido[2,3-d]pyrimidines as Novel inhibitors of Adenosime Kinase; Journal of Medicinal Chemistry (2003) vol. 46 pp. 5249-5257.
Pham, David et al. "Impact of empagliflozin in patients with diabetes and heart failure" (2017) Trends in Cardiovascular Medicine, vol. 27, pp. 144-151.
Phe, V. et al. "Erectile dysfunction and diabetes: A review of the current evidence based medicine and a synthesis of the main available therapies" (2012) Diabetes & Metabolism, 38, 1-13.
Ping, Li "Research Progress On the Effect of Hyperglycemia on Islet B-Cell Function" (2002) Department of Endocrinology, First Hospital of Xi'an Jiaotong University, Xi'an Shaanxi, 242 244.
Piya, Milan K. et al. "Emerging treatment options for type 2 diabetes" British Journal of Clinical Pharmacology, (2010) vol. 70, No. 5, pp. 631-644.
Plosker, Greg L. "Dapagliflozin: A Review of Its Use in Patients with Type 2 Diabetes" (2014) Drugs, 74, 2191-2209.
Poole, Chris D. et al. "The prescription cost of managing people with type 1 and type 2 diabetes following initiation of treatment with either insulin glargine or insulin detemir in routine general practice in the UK: a retrospective database analysis" (2007) Current Medical Research and Opinion, vol. 23, S. 1, pp. S41-S48.
Powers, Richard E. et al. "Understanding the Side Effects of Neuroleptics" (2008) Bureau of Geriatric Psychiatry/DETA, pp. 17-24.
Pratley, Richard E. et al. "Inhibition of DPP-4: a new therapeutic approach for the treatment of type 2 diabetes" (2007) Current Medical Research and Opinion, vol. 23, No. 4, 919-931.
Printz, Richard L. et al. "Tweaking the Glucose Sensor: Adjusting Glucokinase Activity with Activator Compounds" Endocrinology, (2005) vol. 146, No. 9, pp. 3693-3695.
Profit, Louise et al. "Vildagliptin: the evidence for its place in the treatment of type 2 diabetes mellitus" (2008) Core Evidence, 3(1), 13-30.
Pschyrembel et al. Clinical Dictionary, 257th Edition, Diabetes Mellitus, (1993) 320-321.
Rainier, Jon D. et al. "Aluminum- and Boron-Mediated C-Glycoside Synthesis from 1,2-Anhydroglycosides" Organic Letters, (2000) vol. 2, No. 17, pp. 2707-2709.
Randzio, Stanislaw L. et al. "Metastability and Instability of Organic Crystalline Substances" J. Phys. Chem. (2008) 112, pp. 1435-1444.
Redenti, Enrico et al. "Drug/Cyclodextrin/Hydroxy Acid Multicomponent Systems. Properties and Pharmaceutical Applications" Journal of Pharmaceutical Sciences, (2000) vol. 89, No. 1, pp. 1-8.
Remington, The Science and Practice of Pharmacy, 20th Edition, (2000) "Dissolution, Chapter 35" pp. 654-658, 713-714, 884-885 and 1114-1115.
Response dated Jun. 15, 2017 to Non-Final Office Action dated Mar. 10, 2017 from U.S. Appl. No. 14/855,576, filed Sep. 16, 2015.
Response dated Nov. 5, 2008 to Non-Final Office Action dated May 8, 2008 from U.S. Appl. No. 11/359,846, filed Feb. 22, 2006.
Response dated Sep. 25, 2008 to Non-Final Office Action dated Apr. 2, 2008 from U.S. Appl. No. 11/674,839, filed Feb. 14, 2007.
Guay, Andre T. "ED2: Erectile Dysfunction = Endothlial Dysfunction" (2007) Endocrinology and Metabolism Clinics of North America, V 36, 453-463.
Guillory, J. Keith "Generation of Polymorphs, Hydrates, Solvates and Amorphous Solids" Polymorphism in Pharmaceutical Solids (1999) 46 pgs.
Gupta, Rajesh et al. "Emerging Drug Candidates of Dipeptidyl Peptidase IV (DPP IV) Inhibitor Class for the Treatment of Type 2 Diabetes" (2009) Current Drug Targets, vol. 10, No. 1, 71-87.
Hach, T. et al. "The sodium glucose cotransporter-2 (SGLT-2) inhibitor empagliflozin lowers blood pressure independent of weight of HbA changes" (2012) Diabetologia, vol. 55, S 1, p. 317.
Handlon, Anthony L. "Sodium glucose co-transporter 2 (SGLT2) inhibitors as potential antidiabetic agents" (2005) Expert Opinion on Therapeutic Patents, 15:11, 1531-1540.

(56) References Cited

OTHER PUBLICATIONS

Haneda, Masakazu et al. "The Effect of Luseogliflozin (TS-071), a Selective SGLT2 Inhibitor, on Pharmacodynamics and Pharmacokinetics in Japanese Type 2 Diabetic Subjects with Renal Impairment" (2012) Clincial Diabetes/Therapeutics Posters 1062-P, A273.
Hansch, C. "Search for New Drugs, Use of Quantitative Structure—Activity Relationships (QSAR) In Drug Design" (1980) Pomona College, Clermont, CA, Translated from Khimiko-Farmatsevticheskii Zhurnal, vol. 14, No. 10, 15-30.
Harris, Maureen I. "Classification, Diagnostic Criteria, and Screening for Diabetes" (1995) Diabetes in America, 2nd Edition, pp. 15-36.
Hasnain, Mehrul et al. "Metformin for Atypical Antipsychotic-Induced Weight Gain and Glucose Metabolism Dysregulation—Review of Literature and Clinical Suggestions" (2010) CNS Drugs, 24(3), pp. 194-206.
Hatsuda, Asanori., et al.; A Practical Synthesis of Highly Functionalized Aryl Nitriles Through Cyanation of Aryl Bromides Employing Heterogeneous Pd/C; Tetrahedron Letters (2005) vol. 46 pp. 1849-1853; Elsevier Ltd.
Heise, T. et al. "Safety, tolerability, pharmacokinetics and pharmacodynamics following 4 weeks' treatment with empagliflozin once daily in patients with type 2 diabetes" (2013) Diabetes, Obesity and Metabolism, 15: 613-621.
Heise, Tim et al. "BI 10773, a Sodium-Glucose Co-Transporter Inhibitor (SGLT-2), Is Safe and Efficacious Follwing 4-Week Treatment in Patients with Type 2 Diabetes" (2010) American Diabetes Association, vol. 59, 629-P.
Heise, Tim et al. "Treatment with BI 1356, a Novel and Potent DPP-IV Inhibitor Significantly Reduces Glucose Excursions after an oGTT in Patients with Type 2 Diabetes" (2007) Diabetes, Supp 1, vol. 56, 4 pgs.
Henderson, David C. et al. "Clozapine and Hypertension: A Chart Review of 82 Patients" (2004) J Clin Psychiatry, 65, pp. 686-689.
Henry Ford Health System, "Chronic Kidney Disease, Clinical Practice Recommendations for Primary Care Physicians and Healthcare Providers, A Collaborative Approach", (Edition 6.0), 76 pgs.
Ho, Chen-Hsun et al. "The Prevalence and the Risk Factors of Testosterone Deficiency in Newly Diagnosed and Previously Known Type 2 Diabetic Men" (2015) International Society for Sexual Medicine, 12, 389-397.
Holst, Jens Juul et al. "Role of Incretin Hormones in the Regulaion of Insulin Secretion in Diabetic and Nondiabetic Humans" (2004) Am. J Physiol Endocrinol Metab, 287: E199-E206.
Hongu, Mitsuya et al. "Na+ -Glucose Cotransporter Inhibitors as Antidiabetic Agents. II. Synthesis and Structure—Activity Relationships of 4'Dehydroxyphlorizin Derivatives" (1998) Chem. Pharm. Bull. 46(1), 22-33.
Hu, Gongzheng. "Zoopharmacy" China Agriculture Press, Section 4, (2008) pp. 32-33.
Hubert, Mario et al. "Oral solid dosage form—From choice of particle size technique to method development and validation" (2008) American Pharmaceutical Review, 14-23.
Hummel, Charles S. et al. "Glucose transport by human renal Na+ID-glucose co-transporters" (2010) Am J Physiol Cell Physiol, 34 pgs.
Hussar, Daniel A. et al. "2015 New Drug Update" The Consultant Pharmacist, (2015) vol. 30, No. 4, 192-208.
Hussey, Elizabeth K. et al. "Safety, Pharmacokinetics and Pharmacodynamics of Remogliflozin Etabonate (SGLT2 Inhibitor) and Metformin When Co-Administered in Type 2 Diabetes Mellitus (T2DM) Patients" Diabetes, American Diabetes Association, (2009) XP00913667, vol. 58, p. A157.
Hutton, Craig A., et al.; A Convenient Preparation of dityrosine Via Miyaura Borylation-Suzuki Coupling of Iodotyrosine Derivatives; Tetrahedron Letters (2003) vol. 44 pp. 4895-4898; Pergamon Press.
Iacocca, Ronald G. et al. "Particle Engineering: A Strategy for Establishing Drug Substance Physical Property Specifications During Small Molecule Development" (2009) Journal of Pharmaceutical Sciences, vol. 99, No. 1, 51-75.
Idris, Iskandar et al "Sodium-glucose co-transporter-2 inhibitors: an emerging new class of oral antidiabetic drug" (2009) Diabetes, Obesity and Metabolism, 11, 79-88.
Iida, Takehiko., et al; Tributylmagnesium Ate Complex-Mediated Novel Bromine-Magnesium Exchange Reaction for Selective Monosubstitution of Dibromoarenes; Tetrahedron Letters (2001) vol. 42 pp. 4841-4844; Pergamon Press.
Insalaco, Monica et al. "Sodium Glucose Co-transporter Type 2 (SGLT2) Inhibitors in CKD" (2015) Nefrologia, vol. 32, No. 4, pp. 1-9.
Institute of International Medical Education, Glossary of medical education terms, http://www.iime.org/glossary.htm Accessed Mar. 2013 (Year: 2013).
International Search Report and Written Opinion for PCT/EP2012/062922 dated Aug. 14, 2012.
International Search Report for PCT/EP2005/002618 dated Jun. 30, 2005.
International Search Report for PCT/EP2005/056806 dated Dec. 27, 2006.
International Search Report for PCT/EP2006/061520 dated Jul. 26, 2006.
International Search Report for PCT/EP2006/061956 dated Jul. 5, 2006.
International Search report for PCT/EP2006/061957 dated Jul. 5, 2006.
International Search Report for PCT/EP2006/062191 dated Aug. 8, 2006.
International Search Report for PCT/EP2006/064702 dated Jul. 26, 2007.
International Search Report for PCT/EP2006/065710 dated Mar. 8, 2007.
International Search Report for PCT/EP2006/066107 dated Jan. 11, 2007.
International Search Report for PCT/EP2006/066347 dated Mar. 7, 2007.
International Search Report for PCT/EP2007/051411 dated May 2, 2007.
International Search Report for PCT/EP2007/054248 dated Jun. 18, 2007.
International Search Report for PCT/EP2007/062023 dated Sep. 17, 2008.
International Search Report for PCT/EP2010//064117 dated Nov. 30, 2010.
International Search Report for PCT/EP2010/051734 dated Jun. 8, 2010.
International Search Report for PCT/EP2010/051735 dated May 20, 2010.
International Search Report for PCT/EP2010/051736 dated May 7, 2010.
International Search Report for PCT/EP2010/051737 dated May 7, 2010.
International Search Report for PCT/EP2010/064120 dated Mar. 31, 2011.
International Search Report for PCT/EP2010/064619 dated Jan. 20, 2011.
Response dated Sep. 25, 2008 to Non-Final Office Action dated Apr. 2, 2008 from U.S. Appl. No. 117742,612, filed May 1, 2007.
Revesz, Lasslo., et al; SAR of Benzoylpylpyridines and Benzophenones as p38 Alpha MAP Kinase Inhibitors with Oral Activity; Bioorganic & Medicinal Chemistry Letters (2004) vol. 14 pp. 3601-3605.
Revocation of corresponding European patent EP 2981271. May 19, 2021, 1 pg.
Richardson, H. et al. "Effects of rosiglitazone and metformin on pancreatic beta cell and gene expression" (2006) Diabetologia V 49, pp. 685-696.
Riddle, Matthew C. "Oral Pharmacologic Management of Type 2 Diabetes" (1999) American Family Physician, 60(9), 2613-2620.
Rieusset, Jennifer et al. "Insulin Acutely Regulates the Expression of the Peroxisome Proliferator-Activated Receptor -y in Human Adipocytes" (1999) Diabetes, vol. 48, pp. 699-705.
Ritchie, C.W. et al. "The impact upon extra-pyramidal side effects, clinical symptoms and quality of life of a switch from conventional to atypical antipsychotics (risperidone or olanzapine) in elderly

(56) References Cited

OTHER PUBLICATIONS patients with schizophrenia" (2003) International Journal of Geriatric Psychiatry, vol. 18, pp. 432-440.
Robinson, J.A. "Chemical and Biochemical Aspects of Polyether-Ionophore Antibiotic Biosynthesis" (1991) Progress in the Chemistry of Organic Natural Products, 1-81.
Romeo, June H. et al. "Sexual Function in Men with Diabetes Type 2: Association with Glycemic Control" (2000) The Journal of Urology, vol. 163, 788-791.
Rosenstock, J. et al. "Efficacy and safety of empagliflozin, a sodium glucose cotransporter (SGLT2) inhibitor, as add-on to metformin in type 2 diabetes with mild hyperglycaemia" (2013) Diabetes, Obesity and Metabolism, 15: 1154-1160.
Rosenstock, J. et al. "Impact of empagliflozin added on to basal insulin in type 2 diabetes inadequately controlled an basal insulin: a 78-week randomized, double-blind, placebo-controlled trial" (2015) Diabetes, Obesity and Metabolism, 17: 936-948.
Rosenstock, Julio et al. "Dual Add-on Therapy in Type 2 Diabetes Poorly Controlled with Metformin Monotherapy: A Randomized Double-Blind Trial of Saxagliptin Plus Dapagliflozin Addition Versus Single Additon of Saxagliptin or Dapagliflozin to Metformin" (2015) Diabetes Care, vol. 38: 376-383.
Rosenstock, Julio et al. "Improved Glucose Control with Weight Loss, Lower Insulin Doses, and No Increased Hypoglycemia with Empagliflozin Added to Titrated Multiple Daily Injections of Insulin in Obese Inadequately Controlled Type 2 Diabetes" (2014) Diabetes Care, vol. 37, pp. 1815-1823.
Rudnic, Edward et al. "Oral Solid Dosage Forms" Remington—The Science and Practice of Pharmacy, 21th Ed, (2005) Chapter 45, Multiple Compressed Tablets, p. 890.
Rudnic, Edward et al. "Oral Solid Dosage Forms" Remington's Pharmaceutical Sciences, 18th Ed, Gennaro, A.R. Ed, Macie Pub. Co. (1990) pp. 1633-1665.
Scheen, Andre J. "Pharmacokinetic considerations for the treatment of diabetes in patients with chronic kidney disease" (2013) Expert Opinion on Drug Metabolism and Toxicology, 9:5, 529-550.
Schernthaner, G et al. "How attractive is the combination of a sodium glucose co-transporter 2 inhibitor with a dipeptidyl peptidase 4 inhibitor in the treatment of type 2 diabetes" (2015) Diabetes, Obesity and Metabolism, 17, 613-615.
Scottish Medicines Consortium, Product Assessment "dapagliflozin 5mg and 10mg (Forxiga)" Sep. 2012, 14 pgs.
Seman, Leo et al. "Empagliflozin (BI 10773), a Potent and Selective SGLT2 Inhibitor, Induces Dose-Dependent Glucosuria in Healthy Subjects" (2013) Clinical Pharmacology in Drug Development, vol. 2, Issue 2, 20 pgs.
Setter, Stephen M. et al. "Metformin Hydrochloride in the Treatment of Type 2 Diabetes Mellitus: A Clinical Review with a Focus on Dual Therapy" (2003) Clinical Therapeutics, vol. 25, No. 12, 2991-3026.
Shannon, James A. et al. "The Excretion of Inulin, Xylose and Urea by Normal and Phlorizinized Man" New York University College of Medicine, Department of Physiology, Feb. 13, 1935, 393-401.
Sherwin, Robert S. et al. "The Prevention or Delay of Type 2 Diabetes" Diabetes Care, (2002) vol. 25, No. 4, pp. 742-749.
Shioi, Atsushi "Vascular Calcification and Remodeling in Diabetes" (2010) The Journal of Japanese College of Angiology, vol. 50, No. 5, 561-567.
Silverman, et al. "Handbook of Grignard Reagents" Marcel Dekker (1996) p. 82.
Singhal, Dharmendra et al. "Drug polymorphism and dosage form design: a practical perspective" Advanced Drug Delivery Reviews, 56, (2004) pp. 335-347.
Skrtic, Marko et al. "Characterisation of glomerular haemodynamic responses to SGLT2 inhibition in patients with type 1 diabetes and renal hyperfiltration" (2014) Diabetolgia, 4 pgs.
Snorek, Sharon M. et al. "PQRI Recommendations on Particle-Size Analysis of Drug Substances Used in Oral Dosage Forms" (2007) Journal of Pharmaceutical Sciences, vol. 96, No. 6, 1451-1467.

Softeland, Eirik et al. "Empagliflozin as Add-on Therapy in Patients with Type 2 Diabetes Inadequately Controlled With Linagliptin and Metformin: A 24-Week Randomized, Double-Blind, Parallel-Group Trial" (2016) Diabetes Care, DOI:10.2337/dc16-1347, pp. 1-9.
Sommer, Michael Bech., et al.; displacement of Halogen of 2-Halogeno-Substituted Benzonitriles with Carbonions. Preparation of (2-Cyanoaryl)arylacetonitriles; Journal of Organic Chemistry (1990) vol. 55 pp. 4817-4821.
Song, Fujian et al. "What is indirect comparsion?" (2009) Hayward Medical Communications, www.whatisseries.co.uk, 6 pgs.
Stazi, Federica., et al.; Statistical Experimental Design-Driven Discovery of room-Temperature Conditions for Palladium-Catalyzed Cyanation of Aryl Bromides; Tetrahedron Letters (2005) vol. 46 1815-1818; Elsevier Ltd.
Stella, Valentino J. "Prodrugs as therapeutics" (2004) Ashley Publications, vol. 14, No. 3, pp. 277-280.
Stenlof, K. et al. "Efficacy and safety of canagliflozin monotherapy in subjects with type 2 diabetes mellitus inadequately controlled with diet and exercise" (2013) Diabetes, Obesity and Metabolism 15, 372-382.
Strack, Thomas "Metformin: A Review" (2008) Drugs of Today, 44(4), 303-314.
Sturtevant Inc. "Micronizer Jet Mill" (2000), 6 pgs.
Sun, Zhigang et al. "Particle Size Specifications for Solid Oral Dosage Forms: A Regulatory Perspective" (2010) American Pharmaceutical review, vol. 13, Issue 4, 1-14.
Supplementary Data "Supplementary Table 1. Exposure to ipragliflozin in plasma in two cohorts and Geometric Mean Ratio (GMR) of AUCinf and Cmax of ipragliflozin in T2DM patients with different degrees of renal impairment" (2013) American Diabetes Association. 1 pg, Published online at http://care.diabetesjournals.org/lookup/suppl/doi:10.2337/dc12-1503/-/DCI "Web Publication".
Suzuki, Masayuki et al. "Tofogliflozin, a Potent and Hightly Specific Sodium/Glucose Cotransporter 2 Inhibitor, Improves Glycemic Control in Diabetic Rats and Mice" The Journal of Pharmacology and Experimental Therapeutics, vol. 341, No. 3 pp. 692-701.
Svegliati-Baroni, Gianluca et al. "Glucagon-like peptide-1 receptor activation stimulates hepatic lipid oxidation and restores hepatic signalling alteration induced by a high-fat diet in nonalcholic steatohepatitis" (2011) Liver International, vol. 31, 9, pp. 1285-1297.
Swarbrick et al., Encyclopedia of Pharmaceutical Technology, 2nd Edition, (2002) 4 pgs.
Tahrani, Abd A. et al. "SGLT inhibitors in management of diabetes" Lancet Diabetes Endocrinol (2013), 1, 140-151.
Takakura, Shoji et al. "Effect of ipragliflozin, an SGLT2 inhibitor, on progression of diabetic microvascular complications in spontaneously diabetic Torii fatty rats" (2016) Life Sciences, 147, 125-131.
Takebayashi, Kohzo et al. "Effect of Sodium Glucose Cotransporter 2 Inhibitors With Low SGLT2/SGLT1 Selectivity on Circulating Glucagon-Like Peptide 1 Levels in Type 2 Diabetes Mellitus" (2017) J Clin Med Res., vol. 9, (9) 745-753.
Tanaka, Chikako "Therapeutic Drugs for Metabolic Diseases, Chapter 2" (2002) New Yakurigaku (New Pharmacology) pp. 524-527.
Testa, Bernard "Prodrug research: futile or fertile?" (2004) Biochemical Pharmacology vol. 68, pp. 2097-2106.
The American Association of Clinical Endocrinologists Medical Guidelines for the Management of Diabetes Mellitus: The AACE System of Intensive Diabetes Self-Management—2002 Update, (2002) Endocrine Practice, vol. 1, Supp 1, 43 pgs.
Third party observations filed in corresponding EP application No. EP20100703652. Nov. 14, 2019, 6 pgs.
Thomas, L., "Chronic treatment with the Dipeptidyl Peptidase-4 Inhibitor BI 1356[9R)-8-(3-Amino-piperidin-1-yl)-7-but-2-ynyl-3-methyl-1 (4-methyl-quinazolin-2-ylmethyl)-3,7-dihydro-purine-2,6-dione] Increases Basal Glucagon-Like Peptide-1 and Improves Glycemic Control in Diabetic Rodent Models" The Journal of Pharmacology and Experimental Therapeutics, Feb. 2009, vol. 328, No. 2, 556-563.
Thomas, Leo "Long-term treatment with empagliflozin, a novel, potent and selective SGLT-2 inhibitor, improves glycaemic control

(56) References Cited

OTHER PUBLICATIONS and features of metabolic syndrome in diabetic rats" (2012) Diabetes, Obesity and Metabolism, vol. 14, No. 1, 94-96.
Thomas, Leo et al. "(R)-8-(3-Amino-piperidin-1-yl)-7-but-2-ynyl-3-methyl-1-(4-methyl-quinazolin-2-ylmethyl)-3,7-dihydro-purine-2,6-dione (BI 1356), a Novel Xanthine-Based Dipeptidyl Peptidase 4 Inhibitor, Has a Superior Potency and Longer Duration of Action Compared with Other Dipeptidyl Peptidase-4 Inhibitors" Journal of Pharmacology and Experimental Therapeutics (2008) 325, pp. 175-182.
Eli Lilly, "FDA approves Jardiance® (empagliflozin) tablets for adults with type 2 diabetes" (2014) Press Release, 4 pgs.
Ellinger, Lara K. et al. "Efficacy of Metformin and Topiramate in Prevention and Treatment of Second-Generation Antipsychotic-Induced Weight Gain" Annals of Pharmacotherapy (2010) vol. 44, No. 4, pp. 668-679.
EMBASE Database. Accession No. 0050872772. Jelsing, J et al. "Empagliflozin a novel sodium glucose cotransporter-2 inhibitor improves glucose homeostasis and preserves pancreatic beta cell mass in db/db mice" (2012) 2 pgs.
EMBASE database: Accession No. 0050781595. Jelsing, Jacob et al. "The sodium glucose cotransporter-2 (SGLT-2) inhibitor empagliflozin has a durable effect on the restoration of glucose homeostasis by preserving beta-cell mass in zucker diabetic fatty rats" (2012) 2 pgs.
EP08787264.4, Applicant: Boehringer Ingelheim, Patent Claims, (2012) 3 pgs "Web Publication".
Ettmayer, Peter et al. "Lessons Learned from Marketed and Investigational Prodrugs" (2004) Journal of Medicinal Chemistry, vol. 47, No. 10, pp. 2393-2404.
European Medicines Agency "Assessment Report Jardiance, International non-proprietary name: Empagliflozin, Procedure No. EMEA/H/C/002677/0000" (2014) 99 pgs.
European Medicines Agency, ICH Topic Q6 A, "Specifications: Test Procedures and Acceptance Criteria for New Drug Substances and New Drug Products: Chemical Substances", 2000, 32 pgs.
European Medicines Agency, Science Medicines Health, "Assessment Report Forxiga dapagliflozin" (2012) 170 pgs.
European Patent Application 14715578.2, EP2981271; "Third party observations pursuant to article 115 EPC" (2017) 28 pgs.
European Patent EP2981271 B1 (Application 14715578.2); "Third party observations" Anonymous, (2019) 4 pgs.
European Patent Office: Decision revoking corresponding European patent EP 2981271. Jun. 25, 2021, 89 pgs.
Exhibit submitted on Dec. 14, 2017 in parent application U.S. Appl. No. 14/918,727.
Farxiga, Prescribing Information, Reference ID 3433133, Manufactured by Bristol-Myers Squibb Company, published by the FDA on Jan. 8, 2014, 43 pgs.
Ferrannini et al., Supplementary Data, Diabetologia (2010) 53: [SuppH], p. S351.
Ferrannini, E. et al. "Impact of chronic kidney disease and sodium-glucose cotransporter 2 inhibition in patients with type 2 diabetes" (2013) Diabetes Care, vol. 36, 1260-1265.
Ferrannini, E. et al. "A Phase IIb, randomized, placebo-controlled study of the SGLT2 inhibitor empagliflozin in patients with type 2 diabetes" (2013) Diabetes, Obesity and Metabolism, 15: 721-728.
Ferrannini, E. et al. "A Phase IIb, randomized, placebo-controlled study of the SGLT2 inhibitor empagliflozin in patients with type 2 diabetes" (2013) Diabetes, Obesity and Metabolism, vol. 15, Issue 8: Abstract "Web Publication".
Ferrannini, E. et al. "Long-Term Safety and Efficacy of Empagliflozin, Sitagliptin, and Metformin" (2013) Diabetes Care, vol. 36, 4015-4021.
Ferrannini, Ele et al. "CV Protection in the EMPA-REG OUTCOME Trial: A "Thrifty Substrate" Hypothesis" Diabetes Care, Jun. 11, 2016, pp. 1-7.
Ferrannini, Ele et al. "Metabolic response to sodium-glucose cotransporter 2 inhibition in type 2 diabetic patients" (2014) The Journal of Clinical Investigation vol. 124, No. 2, 499-508 and article amendment, p. 1868.
Ferrannini, Ele et al. "Renal Glucose Handling, Impact of chronic kidney disease and sodium-glucose cotransporter 2 inhibition in patients with type 2 diabetes" (2013) Diabetes Care, vol. 36, 1260-1265.
Ferrannini, Ele et al. "Renal Glucose Handling, Impact of chronic kidney disease and sodium-glucose cotransporter 2 inhibition in patients with type 2 diabetes" (2013) Diabetes Care, vol. 36, 1260-1265, "Web Publication".
Ferrannini, Ele et al. "Renal Glucose Handling: Impact of Chronic Kidney Disease (CKD) and SGLT2 Inhibition in Patients with Type 2 Diabetes" (2012) Clinical Diabetes/Therapeutics Posters, 1028-P, A264.
Ferrannini, Ele et al. "SGLT2 inhibition in diabetes mellitus: rationale and clinical prospects" (2012) Nat. Rev. Endocrinol. vol 8, 495-502.
Fiese, Eugene F et al. "Preformulation" (1987) The Theory and Practice of Industrial Pharmacy, 28 pgs.
Final Office Action dated Sep. 28, 2017. U.S. Appl. No. 14/855,576, filed Sep. 16, 2015. First Named Inventor: Uli Christian Broedl; 23 pgs.
Fioretto, Paola et al Efficacy and safety of dapagliflozin in patients with type 2 diabetes and moderate renal impairment (chronic kidney disease stage 3A): The DERIVE Study, (2018) Diabetes, Obesity and Metabolism, 20: 2532-2540.
Fitchett, David et al. "Heart failure outcomes with empagliflozin in patients with type 2 diabetes at high cardiovascular risk: results of the EMPA-REG OUTCOME® trial" (2016) European Heart Journal vol. 37, pp. 1526-1534.
Foote, Celine et al. "Effects of SGLT2 inhibitors on cardiovascular outcomes" (2012) Diabetes & Vascular Disease Research, vol. 9, (2) pp. 117-123.
Friedrich, Christian et al . "A Randomized, Open-Label, Crossover Study to Evaluate the Pharmacokinetics fo Empagliflozin and Linagliptin After Coadministration in Healthy Male Volunteers" (2013) Clincial Therapeutics, vol. 35, No. 1, A33-A42.
Fuerstner, A. et al. "Iron-Catalyzed Cross-Coupling Reactions" (2002) Journal of the American Chemical Society, American Chemical Society, vol. 124, pp. 13856-13863.
Fuerstner, Alois., et al.; Practical Method for the Rhodium-Catalyzed Addition of Aryl- and Alkenylboronic Acids to Aldehydes; Advanced Synthesis and Catalysis (2001) vol. 343 No. 4 pp. 343-350.
Fujii, Masakazu et al. "Oxidative Stress and Diabetic Vascular Diseases" (2009) Angiology Frontier, vol. 8, No. 1, pp. 47-54.
Fujimori, Yoshikazu et al. "Remogliflozin Etabonate in a Novel Category of Selective Low-Affinity Sodium Glucose Cotransporter (SGLT2) Inhibitors, Exhibits Antidiabetic Efficacy in Rodent Models" (2008) Journal of Pharmacology and Experimental Therapeutics vol. 327 No. 1, pp. 268-276.
Garber, A.J. et al. "Vildagliptin in combination with pioglitazone improves glycaemic control in patients with type 2 diabetes failing thiazolidinedione monotherapy: a randomized, placebo-controlled study" (2007) Diabetes, Obesity and Metabolism, 9, 166-174.
Geddes, Colin C. et al. "Glomerular filtration rate—what is the rationale and justification of normalizing GFR for body surface area?" (2008) Nephrology Dialysis Transplantation, 23: 4-6.
Gennaro, Alfonso R. "Remington: The Science and Practice of Pharmacy" Twentieth Edition (2000) 4 pgs.
Ghassemi et al. "Synthesis and properties of new sulfonated poly(p-phenylene) derivatives for proton exchange membranes" Polymer (2004) pp. 5847-5854.
Ghosh, Raktim Kumar et al. "SGLT2 Inhibitors: A New Emerging Therapeutic Class in the Treatment of Type 2 Diabetes Mellitus" (2012) Journal of Clinical Pharmacology, 52, 457-463.
Giuliano, F. "New horizons in erectile and endothelial dysfunction research and therapies" (2008) International Journal of Impotence Research, 20, S2-S8.

(56) References Cited

OTHER PUBLICATIONS

Global Data "Pharmacokinetics, Pharmacodynamics, Safety and Tolerability of BI 10773 in Type II Diabetes Patients with Different Degrees of Renal Impairment" (2017) ClinicalTrials.gov, NCT01907113; 1245.12, 11 pgs.
Golay A. et al. "Link Between Obesity and Type 2 Diabetes" (2005) Best Practice & Research Clinical Endocrinology & Metabolism, vol. 19, No. 4, 649-663.
Goldstein, Barry J. et al. "Effect of Initial Combination Therapy with Sitagliptin, a Dipeptidyl Peptidase -4 Inhibitor and Metformin on Glycemic Control in Patients with Type 2 Diabetes" (2007) Diabetes Care, vol. 30, No. 8, 1979-1987.
Gong, Hegui et al. "A Room Temperature Negishi Cross-Coupling Approach to C-Alkyl Glycosides" (2007) Journal of the American Chemical Society, vol. 129, 1908-1909.
Goodchild, Emily et al. "Managing diabetes in the presence of renal impairment" (2017) Prescriber p. 24-30.
Goodwin, Nicole C. et al. "Novel L-Xylose Derivatives as Selective Sodium-Dependent Glucose Cotransporter (SGLT2) Inhibitors for the Treatment of Type 2 Diabetes" (2009) Journal Medicinal Chemistry vol. 52 pp. 6201-6204.
Graefe-Mody, E.U., et al., "Evaluation of the potential for steady-state pharmacokinectic and pharmacodynamic interactions between the DPP-4 inhibitor linagliptin and metformin in healthy subjects". Current Medical Research and Opinion, Informa Healthcare, GB, vol. 25. No. 8, Aug. 1, 2009, pp. 1963-1972.
Greco, Gary T. et al. "Segregation of Active Constituents from Tablet Formulations During Grinding: Theoretical Considerations" Drug Development and Industrial Pharmacy, (1982) 8(4), pp. 565-578.
Grempler, R et al. "Empagliflozin, a novel selective sodium glucose cotransporter-2 (SGLT-2) inhibitor: characterisation and comparsion with other SGLT-2 inhibitors" Diabetes, Obesity and Metabolism, (2012) vol. 14, pp. 83-90.
Clinical Trial: NCT01131676, BI 10773 (Empagliflozin) Cardiovascular Outcome Trial in Type 2 Diabetes Mellitus Patients (EMPA-RRG Outcome) May 16, 2016.
Davidson, Jaime A. "SGLT2 inhibitors in patients with type 2 diabetes and renal disease: overview of current evidence" (2019) Postgraduate Medicine, 38 pgs.

Emea "CPMP—Note for Guidance on Clinical Investigation of Medicinal Products in the Treatment of Diabetes Mellitus" (2002) 12 pgs.
Heerspink, H.J. Lambers et al. "Is Doubling of Serum Creatinine a Valid Clinical 'Hard' Endpoint in Clinical Nephrology Trials?", (2011) Nephron Clin Pract, vol. 119, c195-c199.
Heerspink, Hiddo J. Lambers et al. "Estimated GFR Decline as a Surrogate End Point for Kidney Failure: A Post Hoc Analysis From the Reduction of End Points in Non-Insulin-Dependent Diabetes With the Angiotensin II Antagonist Losartan (RENAAL) Study and Irbesartan Diabetic Nephropathy Trial (IDNT)" (2014) Original Investigation Pathogenesis and Treatment of Kidney Disease, vol. 63, Issue 2, p. 244-250.
KDIGO 2012 Clinical Practice Guideline for the Evaluation and Management of Chronic Kidney Disease (2013) vol. 3, Issue 1, 163 pgs.
Ma, Terry KW. et al "Renin-angiotensin-aldosterone system blockade for cardiovascular diseases: current status" (2010) British Journal of Pharmacology, 160, 1273-1292.
Roett, Michelle A. et al. "Diabetic Nephropathy—The Family Physician's Role" (2012) vol. 85, No. 9, 884-889.
Schneider, Cornelia et al. "Doubling of serum creatinine and the risk of cardiovascular outcomes in patients with chronic kidney disease and type 2 diabetes mellitus: a cohort study" (2016) Clinical Epidemiology, 8, 177-184.
Shurraw, Sabin et al. "Association between Glycemic Control and Adverse Outcomes in People with Diabetes Mellitus and Chronic Kidney Disease" (2011) Arch Intern Med. 171(21), 1920-1927.
Turner, Robert C. et al. "UKPDS Group: Intensive blood-glucose control with sulphonylureas or insulin compared with conventional treatment and risk of complications in patients with type 2 diabetes (UKPDS 33)" (1998) The Lancet, 352, 837-853.
Wanner, Christoph et al. "Empagliflozin and Progression of Kidney Disease in Type 2 Diabetes" (2016) The New England Journal of Medicine, (Study Protocol, 296 pgs).
Wanner, Christoph et al. "Empagliflozin and Progression of Kidney Disease in Type 2 Diabetes" (2016) The New England Journal of Medicine, (Supplementary Appendix, pp. 1-25).
Wanner, Christoph et al. "Empagliflozin and Progression of Kidney Disease in Type 2 Diabetes" (2016) The New England Journal of Medicine, 1-12.

* cited by examiner

PHARMACEUTICAL COMPOSITION, METHODS FOR TREATING AND USES THEREOF

TECHNICAL FIELD OF THE INVENTION

The present invention relates to certain SGLT-2 inhibitors for treating, preventing, protecting against and/or delaying the progression of chronic kidney disease in patients, for example patients with prediabetes, type 1 or type 2 diabetes mellitus.

BACKGROUND OF THE INVENTION

Chronic kidney disease (CKD), also known as chronic renal disease, is a progressive loss in renal function over a period of months or years. The symptoms of worsening kidney function are non-specific, and chronic kidney disease is often diagnosed as a result of screening of people known to be at risk of kidney problems.

Chronic kidney disease may be identified by a blood test, for example for creatinine. Higher levels of creatinine indicate a lower glomerular filtration rate and as a result a decreased capability of the kidneys to excrete waste products.

CKD has been classified into 5 stages, where stage 1 is kidney damage with normal GFR (mL/min/1.73 m$^2$) of≥90; stage 2 is kidney damage with a mild decrease in GFR (GFR 60-89); stage 3 is a moderate decrease in GFR (GFR 30-59); stage 4 is a severe decrease in GFR (GFR 15-29); and stage 5 is kidney failure (GFR<15 or dialysis). Stage 5 CKD is often called End Stage Renal Disease (ESRD) and is synonymous with the now outdated terms chronic kidney failure (CKF) or chronic renal failure (CRF).

Albuminuria can also be a sign of kidney disease. Albuminuria has been classified into 3 categories, where category A1 reflects no albuminuria with albumin normal to mildly increased; category A2 which reflects microalbuminuria with albumin moderately increased; category A3 which reflects macroalbuminuria with albumin severely increased.

There is no specific treatment unequivocally shown to slow the worsening of chronic kidney disease and severe CKD requires renal replacement therapy, which may involve a form of dialysis, but ideally constitutes a kidney transplant.

Therefore, there is an unmet medical need for methods, medicaments and pharmaceutical compositions able to slow the worsening or progression of chronic kidney disease in patients, in particular patients at risk of renal diseases, for example patients with prediabetes, type 1 or type 2 diabetes mellitus.

SUMMARY OF THE INVENTION

Accordingly, in one aspect, the present invention relates to certain SGLT-2 inhibitors, for example empagliflozin, for treating, preventing, protecting against, reducing the risk of, delaying the occurrence of and/or delaying the progression of chronic kidney disease in patients, for example patients with prediabetes, type 1 or type 2 diabetes mellitus.

In one embodiment, the present invention provides a method of treating, preventing, protecting against, reducing the risk of, delaying the occurrence of and/or delaying the progression of chronic kidney disease in a patient, said method comprising administering empagliflozin, optionally in combination with one or more other therapeutic substances, to the patient. In one aspect, the progression of said chronic kidney disease is the progression to end stage renal disease/kidney failure, or renal death in the patient.

In one embodiment, the present invention provides a method of treating, preventing, protecting against or delaying new onset of albuminuria in a patient, said method comprising administering empagliflozin, optionally in combination with one or more other therapeutic substances, to the patient. In one aspect, the patient is at risk for renal disease.

In one aspect, in one of the above methods, the patient is a patient with prediabetes, type 1 or type 2 diabetes mellitus. In one aspect, the patient has or is at risk of a cardiovascular disease. In one aspect, the patient is a patient with prediabetes, type 1 or type 2 diabetes mellitus and with or at risk of a cardiovascular disease.

In one embodiment, the present invention provides a method of treating, preventing, protecting against or delaying the progression from no albuminuria to micro- or macroalbuminuria in a patient at risk for renal disease, said method comprising administering empagliflozin, optionally in combination with one or more other therapeutic substances, to the patient.

In one embodiment, the present invention provides a method of treating, preventing, protecting against or delaying the progression from microalbuminuria to macroalbuminuria in a patient with chronic kidney disease, said method comprising administering empagliflozin, optionally in combination with one or more other therapeutic substances, to the patient.

In one aspect, in a method above the patient is a patient with prediabetes, type 1 or type 2 diabetes mellitus.

In one embodiment, the present invention provides a method for treating, preventing, protecting against or delaying the progression of chronic kidney disease in a patient, in particular a patient with chronic kidney disease, said method administering empagliflozin, optionally in combination with one or more other therapeutic substances, to the patient. In one aspect, the method is for preventing, protecting against or delaying loss of eGFR, for example sustained eGFR loss of≥50%, in said patient. In one aspect, the patient is a patient with prediabetes, type 1 or type 2 diabetes mellitus.

In one embodiment, the present invention provides a method of treating, preventing, protecting against or delaying the occurrence of:
  new onset of albuminuria,
  doubling of serum creatinine level accompanied by an eGFR (based on modification of diet in renal disease (MDRD) formula)≤45 mL/min/1.73m$^2$,
  need for continuous renal replacement therapy, or
    death due to renal disease,
  in a patient, said method comprising administering empagliflozin, optionally in combination with one or more other therapeutic substances, to the patient.

In one aspect, the patient has chronic kidney disease. In one aspect, the patient is a patient with prediabetes, type 1 or type 2 diabetes mellitus. In one aspect, the patient has or is at risk of a cardiovascular disease. In one aspect, the patient is a patient with prediabetes, type 1 or type 2 diabetes and with or at risk of a cardiovascular disease. In one aspect, the patient has chronic kidney disease and is a patient with prediabetes, type 1 or type 2 diabetes mellitus.

In one aspect, in any one of the methods above the patient is a patient with one or more cardiovascular risk factors selected from A), B), C) and D), for example a patient with type 1 or type 2 diabetes mellitus or with pre-diabetes with one or more cardiovascular risk factors selected from A), B), C) and D):

A) previous or existing vascular disease selected from myocardial infarction, coronary artery disease, percutaneous coronary intervention, coronary artery by-pass grafting, ischemic or hemorrhagic stroke, congestive heart failure, and peripheral occlusive arterial disease, B) advanced age>/=60-70 years, and C) one or more cardiovascular risk factors selected from advanced type 1 or type 2 diabetes mellitus>10 years duration, hypertension, current daily cigarette smoking, dyslipidemia, obesity, age>/=40, metabolic syndrome, hyperinsulinemia or insulin resistance, and hyperuricemia, erectile dysfunction, polycystic ovary syndrome, sleep apnea, or family history of vascular disease or cardiomyopathy in first-degree relative;

D) one or more of the following:

confirmed history of myocardial infarction, unstable angina with documented multivessel coronary disease or positive stress test, multivessel Percutaneous Coronary Intervention, multivessel Coronary Artery By-pass Grafting (CABG), history of ischemic or hemorrhagic stroke, peripheral occlusive arterial disease.

In one aspect of the present invention, a patient having cardiovascular disease is defined as having at least one of the following:

Confirmed history of myocardial infarction; or

Evidence of multivessel coronary artery disease, in 2 or more major coronary arteries, irrespective of the revascularization status, i.e.
  a) Either the presence of a significant stenosis (imaging evidence of at least 50% narrowing of the luminal diameter measured during a coronary angiography or a multi-sliced computed tomography angiography), in 2 or more major coronary arteries,
  b) Or a previous revascularisation (percutaneous transluminal coronary angioplasty with or without stent, or coronary artery bypass grafting), in 2 or more major coronary arteries,
  c) Or the combination of previous revascularisation in one major coronary artery (percutaneous transluminal coronary angioplasty with or without stent, or coronary artery bypass grafting), and the presence of a significant stenosis in another major coronary artery (imaging evidence of at least 50% narrowing of the luminal diameter measured during a coronary angiography or a multi-sliced computed tomography angiography), Note: A disease affecting the left main coronary artery is considered as a 2-vessel disease.

Evidence of a single vessel coronary artery disease with:
  a) The presence of a significant stenosis i.e. the imaging evidence of at least 50% narrowing of the luminal diameter of one major coronary artery in patients not subsequently successfully revascularised (measured during a coronary angiography or a multi-sliced computed tomography angiography)
  b) And at least one of the following (either (i) or (ii)):
    i. A positive non invasive stress test, confirmed by either:
      1. A positive exercise tolerance test in patients without a complete left bundle branch block, Wolff-Parkinson-White syndrome, or paced ventricular rhythm, or
      2. A positive stress echocardiography showing regional systolic wall motion abnormalities, or
      3. A positive scintigraphic test showing stress-induced ischemia, i.e. the development of transient perfusion defects during myocardial perfusion imaging;
    ii. Or patient discharged from hospital with a documented diagnosis of unstable angina within 12 months prior to selection.

Episode of unstable angina with confirmed evidence of coronary multivessel or single vessel disease as defined above.

History of ischemic or haemorrhagic stroke

Presence of peripheral artery disease (symptomatic or not) documented by either: previous limb angioplasty, stenting or bypass surgery; or previous limb or foot amputation due to circulatory insufficiency; or angiographic evidence of significant (>50%) peripheral artery stenosis in at least one limb; or evidence from a non-invasive measurement of significant (>50% or as reported as hemodynamically significant) peripheral artery stenosis in at least one limb; or ankle brachial index of<0.9 in at least one limb.

In one aspect of the present invention, a patient having cardiovascular disease is defined as having at least one of the following:
  a) Confirmed history of myocardial infarction,
  b) Unstable angina with documented multivessel coronary disease (at least two major coronary arteries in angiogram) or positive stress test (ST segment depression>=2 mm or a positive nuclear perfusion scintigram),
  c) Multivessel Percutaneous Coronary Intervention (PCI),
  d) Multivessel Coronary Artery By-pass Grafting (CABG), including with recurrent angina following surgery,
  e) History of ischemic or hemorrhagic stroke,
  f) Peripheral occlusive arterial disease (previous limb bypass surgery or percutaneous transluminal angioplasty; previous limb or foot amputation due to circulatory insufficiency, angiographic or imaging detected (for example: ultrasound, Magnetic Resonance Imaging) significant vessel stenosis of major limb arteries).

In one aspect, in any one of the methods above the one or more other therapeutic substances are selected from other antidiabetic substances.

In one aspect, any one of the methods above comprises administering empagliflozin in combination with metformin, with linagliptin or with metformin and linagliptin.

In one aspect, in any one of the methods above the one or more other therapeutic substances is a RAAS inhibitor. In one aspect, the one or more other therapeutic substances is a direct renin inhibitor, an Angiotensin-Converting Enzyme (ACE) inhibitor and/or an angiotensin II receptor blocker (ARB).

In one aspect, any one of the methods above comprises administering empagliflozin in combination with a RAAS inhibitor. In one aspect, any one of the methods above comprises administering empagliflozin in combination with a direct renin inhibitor, an Angiotensin-Converting Enzyme (ACE) inhibitor and/or an angiotensin II receptor blocker (ARB).

In one aspect, in any one of the methods above empagliflozin is administered orally in a total daily amount of 10 mg or 25 mg. In one aspect empagliflozin is administered as a pharmaceutical composition comprising 10 mg or 25 mg of empagliflozin.

In one aspect of the present invention, in a method or use disclosed herein a patient is a patient with type 2 diabetes mellitus (or type 2 diabetes patient), a patient treated for type 2 diabetes mellitus, a patient diagnosed with type 2 diabetes mellitus or a patient in need of treatment for type 2 diabetes mellitus. In one aspect, a patient is a patient with pre-diabetes.

In one aspect of the present invention, in a method or use disclosed herein a patient is a patient with obesity-related Glomerulopathy, a patient with perihilar fokal-segmental glomerulosclerosis or a patient with IgA nephropathy.

Accordingly, in one embodiment, the present invention provides a method of treating, preventing, protecting against, reducing the risk of, delaying the occurrence of and/or delaying the progression of chronic kidney disease in a patient with obesity-related Glomerulopathy, in a patient with perihilar fokal-segmental glomerulosclerosis or in a patient with IgA nephropathy.

The present invention further provides for empagliflozin or a pharmaceutical composition comprising empagliflozin for use as a medicament in any one of the methods described herein.

The present invention further provides for empagliflozin in combination with one or more other therapeutic substances, for example selected from other antidiabetic substances, in particular metformin, linagliptin or metformin and linagliptin, or a pharmaceutical composition comprising empagliflozin and one or more other therapeutic substances, for example selected from other antidiabetic substances, in particular metformin, linagliptin or metformin and linagliptin, for use as a medicament in any one of the methods described herein.

The present invention further provides for empagliflozin in combination with a RAAS inhibitor, in particular a direct renin inhibitor, an Angiotensin-Converting Enzyme (ACE) inhibitor and/or an angiotensin II receptor blocker (ARB), or a pharmaceutical composition comprising empagliflozin and a RAAS inhibitor, in particular a direct renin inhibitor, an Angiotensin-Converting Enzyme (ACE) inhibitor and/or an angiotensin II receptor blocker (ARB), for use as a medicament in any one of the methods described herein.

The present invention further provides for empagliflozin or a pharmaceutical composition comprising empagliflozin for use in the treatment of any one of the diseases or conditions described herein.

The present invention further provides for empagliflozin in combination with one or more other therapeutic substances, for example selected from other antidiabetic substances, in particular metformin, linagliptin or metformin and linagliptin, or a pharmaceutical composition comprising empagliflozin and one or more other therapeutic substances, for example selected from other antidiabetic substances, in particular metformin, linagliptin or metformin and linagliptin, for use in the treatment of any one of the diseases or conditions described herein.

The present invention further provides for empagliflozin in combination with a RAAS inhibitor, in particular a direct renin inhibitor, an Angiotensin-Converting Enzyme (ACE) inhibitor and/or an angiotensin II receptor blocker (ARB), or a pharmaceutical composition comprising empagliflozin and a RAAS inhibitor, in particular a direct renin inhibitor, an Angiotensin-Converting Enzyme (ACE) inhibitor and/or an angiotensin II receptor blocker (ARB), for use in the treatment of any one of the diseases or conditions described herein.

The present invention further provides for empagliflozin or a pharmaceutical composition comprising empagliflozin for use in the manufacture of a medicament for use in any one of the methods described herein.

The present invention further provides for empagliflozin in combination with one or more other therapeutic substances, for example selected from other antidiabetic substances, in particular metformin, linagliptin or metformin and linagliptin, or a pharmaceutical composition comprising empagliflozin and one or more other therapeutic substances, for example selected from other antidiabetic substances, in particular metformin, linagliptin or metformin and linagliptin, for use in the manufacture of a medicament for use in any one of the methods described herein.

The present invention further provides for empagliflozin in combination with a RAAS inhibitor, in particular a direct renin inhibitor, an Angiotensin-Converting Enzyme (ACE) inhibitor and/or an angiotensin II receptor blocker (ARB), or a pharmaceutical composition comprising empagliflozin and a RAAS inhibitor, in particular a direct renin inhibitor, an Angiotensin-Converting Enzyme (ACE) inhibitor and/or an angiotensin II receptor blocker (ARB), for use in the manufacture of a medicament for use in any one of the methods described herein.

Definitions

The term "active ingredient" of a pharmaceutical composition according to the present invention means the SGLT2 inhibitor according to the present invention. An "active ingredient" is also sometimes referred to herein as an "active substance".

The term "body mass index" or "BMI" of a human patient is defined as the weight in kilograms divided by the square of the height in meters, such that BMI has units of $kg/m^2$.

The term "overweight" is defined as the condition wherein the individual has a BMI greater than or 25 $kg/m^2$ and less than 30 $kg/m^2$. The terms "overweight" and "pre-obese" are used interchangeably.

The terms "obesity" or "being obese" and the like are defined as the condition wherein the individual has a BMI equal to or greater than 30 $kg/m^2$. According to a WHO definition the term obesity may be categorized as follows: the term "class I obesity" is the condition wherein the BMI is equal to or greater than 30 $kg/m^2$ but lower than 35 $kg/m^2$; the term "class II obesity" is the condition wherein the BMI is equal to or greater than 35 $kg/m^2$ but lower than 40 $kg/m^2$; the term "class III obesity" is the condition wherein the BMI is equal to or greater than 40 $kg/m^2$.

The indication obesity includes in particular exogenic obesity, hyperinsulinaemic obesity, hyperplasmic obesity, hyperphyseal adiposity, hypoplasmic obesity, hypothyroid obesity, hypothalamic obesity, symptomatic obesity, infantile obesity, upper body obesity, alimentary obesity, hypogonadal obesity, central obesity, visceral obesity, abdominal obesity.

The term "visceral obesity" is defined as the condition wherein a waist-to-hip ratio of greater than or equal to 1.0 in men and 0.8 in women is measured. It defines the risk for insulin resistance and the development of pre-diabetes.

The term "abdominal obesity" is usually defined as the condition wherein the waist circumference is>40 inches or 102 cm in men, and is>35 inches or 94 cm in women. With regard to a Japanese ethnicity or Japanese patients abdominal obesity may be defined as waist circumference 85 cm in men and 90 cm in women (see e.g. investigating committee for the diagnosis of metabolic syndrome in Japan).

The term "euglycemia" is defined as the condition in which a subject has a fasting blood glucose concentration within the normal range, greater than 70 mg/dL (3.89 mmol/L) and less than 100 mg/dL (5.6 mmol/L). The word "fasting" has the usual meaning as a medical term.

The term "hyperglycemia" is defined as the condition in which a subject has a fasting blood glucose concentration above the normal range, greater than 100 mg/dL (5.6 mmol/L). The word "fasting" has the usual meaning as a medical term.

The term "hypoglycemia" is defined as the condition in which a subject has a blood glucose concentration below the normal range, in particular below 70 mg/dL (3.89 mmol/L).

The term "postprandial hyperglycemia" is defined as the condition in which a subject has a 2 hour postprandial blood glucose or serum glucose concentration greater than 200 mg/dL (11.11 mmol/L).

The term "impaired fasting blood glucose" or "IFG" is defined as the condition in which a subject has a fasting blood glucose concentration or fasting serum glucose concentration in a range from 100 to 125 mg/dl (i.e. from 5.6 to 6.9 mmol/l), in particular greater than 110 mg/dL and less than 126 mg/dl (7.00 mmol/L). A subject with "normal fasting glucose" has a fasting glucose concentration smaller than 100 mg/dl, i.e. smaller than 5.6 mmol/l.

The term "impaired glucose tolerance" or "IGT" is defined as the condition in which a subject has a 2 hour postprandial blood glucose or serum glucose concentration greater than 140 mg/dl (7.78 mmol/L) and less than 200 mg/dL (11.11 mmol/L). The abnormal glucose tolerance, i.e. the 2 hour postprandial blood glucose or serum glucose concentration can be measured as the blood sugar level in mg of glucose per dL of plasma 2 hours after taking 75 g of glucose after a fast. A subject with "normal glucose tolerance" has a 2 hour postprandial blood glucose or serum glucose concentration smaller than 140 mg/dl (7.78 mmol/L).

The term "hyperinsulinemia" is defined as the condition in which a subject with insulin resistance, with or without euglycemia, has fasting or postprandial serum or plasma insulin concentration elevated above that of normal, lean individuals without insulin resistance, having a waist-to-hip ratio<1.0 (for men) or<0.8 (for women).

The terms "insulin-sensitizing", "insulin resistance-improving" or "insulin resistance-lowering" are synonymous and used interchangeably.

The term "insulin resistance" is defined as a state in which circulating insulin levels in excess of the normal response to a glucose load are required to maintain the euglycemic state (Ford ES, et al. JAMA. (2002) 287:356-9). A method of determining insulin resistance is the euglycaemic-hyperinsulinaemic clamp test. The ratio of insulin to glucose is determined within the scope of a combined insulin-glucose infusion technique. There is found to be insulin resistance if the glucose absorption is below the 25th percentile of the background population investigated (WHO definition). Rather less laborious than the clamp test are so called minimal models in which, during an intravenous glucose tolerance test, the insulin and glucose concentrations in the blood are measured at fixed time intervals and from these the insulin resistance is calculated. With this method, it is not possible to distinguish between hepatic and peripheral insulin resistance.

Furthermore, insulin resistance, the response of a patient with insulin resistance to therapy, insulin sensitivity and hyperinsulinemia may be quantified by assessing the "homeostasis model assessment to insulin resistance (HOMA-IR)" score, a reliable indicator of insulin resistance (Katsuki A, et al. Diabetes Care 2001; 24: 362-5). Further reference is made to methods for the determination of the HOMA-index for insulin sensitivity (Matthews et al., Diabetologia 1985, 28: 412-19), of the ratio of intact proinsulin to insulin (Forst et al., Diabetes 2003, 52(Suppl1): A459) and to an euglycemic clamp study. In addition, plasma adiponectin levels can be monitored as a potential surrogate of insulin sensitivity. The estimate of insulin resistance by the homeostasis assessment model (HOMA)-IR score is calculated with the formula (Galvin P, et al. Diabet Med 1992;9:921-8):

HOMA-IR=[fasting serum insulin (µU/mL)]×[fasting plasma glucose(mmol/L)/22.5]

Insulin resistance can be confirmed in these individuals by calculating the HOMA-IR score. For the purpose of this invention, insulin resistance is defined as the clinical condition in which an individual has a HOMA-IR score>4.0 or a HOMA-IR score above the upper limit of normal as defined for the laboratory performing the glucose and insulin assays.

As a rule, other parameters are used in everyday clinical practice to assess insulin resistance. Preferably, the patient's triglyceride concentration is used, for example, as increased triglyceride levels correlate significantly with the presence of insulin resistance.

Individuals likely to have insulin resistance are those who have two or more of the following attributes: 1) overweight or obese, 2) high blood pressure, 3) hyperlipidemia, 4) one or more 1st degree relative with a diagnosis of IGT or IFG or type 2 diabetes.

Patients with a predisposition for the development of IGT or IFG or type 2 diabetes are those having euglycemia with hyperinsulinemia and are by definition, insulin resistant. A typical patient with insulin resistance is usually overweight or obese. If insulin resistance can be detected, this is a particularly strong indication of the presence of pre-diabetes. Thus, it may be that in order to maintain glucose homoeostasis a person needs 2-3 times as much insulin as a healthy person, without this resulting in any clinical symptoms.

"Pre-diabetes" is a general term that refers to an intermediate stage between normal glucose tolerance (NGT) and overt type 2 diabetes mellitus (T2DM), also referred to as intermediate hyperglycaemia. As such, it represents 3 groups of individuals, those with impaired glucose tolerance (IGT) alone, those with impaired fasting glucose (IFG) alone or those with both IGT and IFG. IGT and IFG usually have distinct pathophysiologic etiologies, however also a mixed condition with features of both can exist in patients. Therefore in the context of the present invention a patient being diagnosed of having "pre-diabetes" is an individual with diagnosed IGT or diagnosed IFG or diagnosed with both IGT and IFG. Following the definition according to the American Diabetes Association (ADA) and in the context of the present invention a patient being diagnosed of having "pre-diabetes" is an individual with:

a) a fasting plasma glucose (FPG) concentration<100 mg/dL [1 mg/dL=0.05555 mmol/L] and a 2-hour plasma glucose (PG) concentration, measured by a 75-g oral glucose tolerance test (OGTT), ranging between≥140 mg/dL and<200 mg/dL (i.e., IGT); or b) a fasting plasma glucose (FPG) concentration between≥100 mg/dL and<126 mg/dL and a 2-hour plasma glucose (PG) concentration, measured by a 75-g oral glucose tolerance test (OGTT) of<140 mg/dL (i.e., IFG); or c) a fasting plasma glucose (FPG) concentration between≥100 mg/dL and<126 mg/dL and a 2-hour plasma glucose (PG) concentration, measured by a 75-g oral glucose tolerance test (OGTT), ranging between≥140 mg/dL and<200 mg/dL (i.e., both IGT and IFG).

Patients with "pre-diabetes" are individuals being predisposed to the development of type 2 diabetes. Pre-diabetes extends the definition of IGT to include individuals with a fasting blood glucose within the high normal range≥100 mg/dL (J. B. Meigs, et al. Diabetes 2003; 52:1475-1484). The scientific and medical basis for identifying pre-diabetes as a serious health threat is laid out in a Position Statement entitled "The Prevention or Delay of Type 2 Diabetes" issued jointly by the American Diabetes Association and the National Institute of Diabetes and Digestive and Kidney Diseases (Diabetes Care 2002; 25:742-749).

The methods to investigate the function of pancreatic beta-cells are similar to the above methods with regard to insulin sensitivity, hyperinsulinemia or insulin resistance: An improvement of beta-cell function can be measured for example by determining a HOMA-index for beta-cell function (Matthews et al., Diabetologia 1985, 28: 412-19), the ratio of intact proinsulin to insulin (Forst et al., Diabetes 2003, 52(Suppl.1): A459), the insulin/C-peptide secretion after an oral glucose tolerance test or a meal tolerance test, or by employing a hyperglycemic clamp study and/or minimal modeling after a frequently sampled intravenous glucose tolerance test (Stumvoll et al., Eur J Clin Invest 2001, 31: 380-81).

The term "type 1 diabetes" is defined as the condition in which a subject has, in the presence of autoimmunity towards the pancreatic beta-cell or insulin, a fasting blood glucose or serum glucose concentration greater than 125 mg/dL (6.94 mmol/L). If a glucose tolerance test is carried out, the blood sugar level of a diabetic will be in excess of 200 mg of glucose per dL (11.1 mmol/l) of plasma 2 hours after 75 g of glucose have been taken on an empty stomach, in the presence of autoimmunity towards the pancreatic beta cell or insulin. In a glucose tolerance test 75 g of glucose are administered orally to the patient being tested after 10-12 hours of fasting and the blood sugar level is recorded immediately before taking the glucose and 1 and 2 hours after taking it. The presence of autoimmunity towards the pancreatic beta-cell may be observed by detection of circulating islet cell autoantibodies ["type 1A diabetes mellitus"], i.e., at least one of: GAD65 [glutamic acid decarboxylase-65], ICA [islet-cell cytoplasm], IA-2 [intracytoplasmatic domain of the tyrosine phosphatase-like protein IA-2], ZnT8 [zinc-transporter-8] or anti-insulin; or other signs of autoimmunity without the presence of typical circulating autoantibodies [type 1B diabetes], i.e. as detected through pancreatic biopsy or imaging). Typically a genetic predisposition is present (e.g. HLA, INS VNTR and PTPN22), but this is not always the case.

The term "type 2 diabetes mellitus" or "T2DM" is defined as the condition in which a subject has a fasting blood glucose or serum glucose concentration greater than 125 mg/dL (6.94 mmol/L). The measurement of blood glucose values is a standard procedure in routine medical analysis. If a glucose tolerance test is carried out, the blood sugar level of a diabetic will be in excess of 200 mg of glucose per dL (11.1 mmol/l) of plasma 2 hours after 75 g of glucose have been taken on an empty stomach. In a glucose tolerance test 75 g of glucose are administered orally to the patient being tested after 10-12 hours of fasting and the blood sugar level is recorded immediately before taking the glucose and 1 and 2 hours after taking it. In a healthy subject, the blood sugar level before taking the glucose will be between 60 and 110 mg per dL of plasma, less than 200 mg per dL 1 hour after taking the glucose and less than 140 mg per dL after 2 hours. If after 2 hours the value is between 140 and 200 mg, this is regarded as abnormal glucose tolerance.

The term "late stage type 2 diabetes mellitus" includes patients with a secondary drug failure, indication for insulin therapy and progression to micro- and macrovascular complications e.g. diabetic nephropathy, or coronary heart disease (CHD).

The term "HbA1c" refers to the product of a non-enzymatic glycation of the haemoglobin B chain. Its determination is well known to one skilled in the art. In monitoring the treatment of diabetes mellitus the HbA1c value is of exceptional importance. As its production depends essentially on the blood sugar level and the life of the erythrocytes, the HbA1c in the sense of a "blood sugar memory" reflects the average blood sugar levels of the preceding 4-6 weeks. Diabetic patients whose HbA1c value is consistently well adjusted by intensive diabetes treatment (i.e.<6.5% of the total haemoglobin in the sample), are significantly better protected against diabetic microangiopathy. For example, metformin on its own achieves an average improvement in the HbA1c value in the diabetic of the order of 1.0-1.5%. This reduction of the HbA1C value is not sufficient in all diabetics to achieve the desired target range of<7% or<6.5% and preferably<6% HbA1c.

The term "insufficient glycemic control" or "inadequate glycemic control" in the scope of the present invention means a condition wherein patients show HbA1c values above 6.5%, in particular above 7.0%, even more preferably above 7.5%, especially above 8%.

The "metabolic syndrome", also called "syndrome X" (when used in the context of a metabolic disorder), also called the "dysmetabolic syndrome" is a syndrome complex with the cardinal feature being insulin resistance (Laaksonen DE, et al. Am J Epidemiol 2002;156:1070-7). According to the ATP III/NCEP guidelines (Executive Summary of the Third Report of the National Cholesterol Education Program (NCEP) Expert Panel on Detection, Evaluation, and Treatment of High Blood Cholesterol in Adults (Adult Treatment Panel III) JAMA: Journal of the American Medical Association (2001) 285:2486-2497), diagnosis of the metabolic syndrome is made when three or more of the following risk factors are present:

1. Abdominal obesity, defined as waist circumference>40 inches or 102 cm in men, and>35 inches or 94 cm in women; or with regard to a Japanese ethnicity or Japanese patients defined as waist circumference≥85 cm in men and≥90 cm in women;
2. Triglycerides:≥150 mg/dL
3. HDL-cholesterol<40 mg/dL in men
4. Blood pressure≥130/85 mm Hg (SBP≥130 or DBP≥85)
5. Fasting blood glucose≥100 mg/dL The NCEP definitions have been validated (Laaksonen DE, et al. Am J Epidemiol. (2002) 156:1070-7). Triglycerides and HDL cholesterol in the blood can also be determined by standard methods in medical analysis and are described for example in Thomas L (Editor): "Labor and Diagnose", TH-Books Verlagsgesellschaft mbH, Frankfurt/Main, 2000.

According to a commonly used definition, hypertension is diagnosed if the systolic blood pressure (SBP) exceeds a value of 140 mm Hg and diastolic blood pressure (DBP) exceeds a value of 90 mm Hg. If a patient is diagnosed with diabetes it is currently recommended that the systolic blood pressure be reduced to a level below 130 mm Hg and the diastolic blood pressure be lowered to below 80 mm Hg.

The term "chronic kidney disease (CDK)" is defined as abnormalities of kidney structure or function, present for more than three months, with implications for health. CKD is classified based on cause, GFR category, and albuminuria category (CGA).

CKD has been classified into 5 stages, where stage 1 is kidney damage with normal GFR (mL/min/1.73 m2) of 90 or above; stage 2 is kidney damage with a mild decrease in GFR (GFR 60-89); stage 3 is a moderate decrease in GFR (GFR 30-59); stage 4 is a severe decrease in GFR (GFR 15-29); and stage 5 is kidney failure (GFR<15 or dialysis). Stage 3 has been subdivided into stage 3A, which is a mild to moderate decrease in GFR (GFR 45-59), and stage 3B, which is a moderate to severe decrease in GFR (GFR 30-44).

The term "glomerular filtration rate (GFR)" is defined as the volume of fluid filtered from the renal (kidney) glomerular capillaries into the Bowman's capsule per unit time. It is indicative of overall kidney function. The glomerular filtration rate (GFR) can be calculated by measuring any chemical that has a steady level in the blood, and is freely filtered but neither reabsorbed nor secreted by the kidneys. The rate therefore measured is the quantity of the substance in the urine that originated from a calculable volume of blood. The GFR is typically recorded in units of volume per time, e.g., milliliters per minute and the formula below can be used:

GFR=(Urine Concentration×Urine Volume)/Plasma Concentration

The GFR can be determined by injecting inulin into the plasma. Since inulin is neither reabsorbed nor secreted by the kidney after glomerular filtration, its rate of excretion is directly proportional to the rate of filtration of water and solutes across the glomerular filter. A normal value is: GFR=90-125 mL/min/1.73 m$^2$, in particular GFR=100-125 mL/min/1.73 m$^2$.

Other principles to determine GFR involve measuring 51Cr-EDTA, [125I] iothalamate or iohexol.

The "estimated glomerular filtration rate (eGFR)" is defined as derived at screening from serum creatinine values based on e.g., the Chronic Kidney Disease Epidemiology Collaboration (CKD-EPI) equation, the Cockcroft-Gault formula or the Modification of Diet in Renal Disease (MDRD) formula, which are all known in the art.

The term "albuminuria" is defined as a condition wherein more than the normal amount of albumin is present in the urine. Albuminuria can be determined by the albumin excretion rate (AER) and/or the albumin-to-creatine ratio (ACR) in the urine (also refered to as UACR). Albuminuria categories in CKD are defined as follows:

Category A1 reflects no albuminuria, category A2 reflects microalbuminuria, category A3 reflects macroalbuminuria. The progression of category A1 usually leads to microalbuminuria (A2) but may also directly result in macroalbuminuria (A3). Progression of microalbuminuria (A2) results in macroalbuminuria (A3).

The term "empagliflozin" refers to the SGLT2 inhibitor 1-chloro-4-(β-D-glucopyranos-1-yl)-244-((S)-tetrahydrofuran-3-yloxy)-benzylFbenzene of the formula

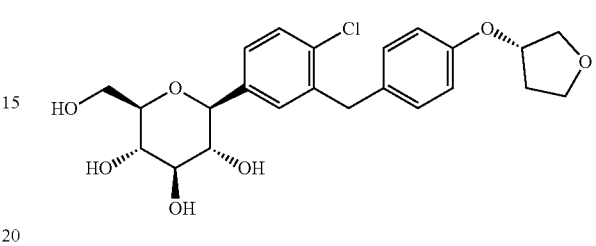

as described for example in WO 2005/092877. Methods of synthesis are described in the literature, for example WO 06/120208 and WO 2011/039108. According to this invention, it is to be understood that the definition of empagliflozin also comprises its hydrates, solvates and polymorphic forms thereof, and prodrugs thereof. An advantageous crystalline form of empagliflozin is described in WO 2006/117359 and WO 2011/039107 which hereby are incorporated herein in their entirety. This crystalline form possesses good solubility properties which enables a good bioavailability of the SGLT2 inhibitor. Furthermore, the crystalline form is physico-chemically stable and thus provides a good shelf-life stability of the pharmaceutical composition. Preferred pharmaceutical compositions, such as solid formulations for oral administration, for example tablets, are described in WO 2010/092126, which hereby is incorporated herein in its entirety.

The terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy.

The terms "prophylactically treating", "preventivally treating" and "preventing" are used interchangeably and comprise a treatment of patients at risk to develop a condition mentioned hereinbefore, thus reducing said risk.

The term "tablet" comprises tablets without a coating and tablets with one or more coatings. Furthermore the "term" tablet comprises tablets having one, two, three or even more layers and press-coated tablets, wherein each of the beforementioned types of tablets may be without or with one or

| | | ACR (approximate equivalent) | | |
|---|---|---|---|---|
| Category | AER (mg/24 hours) | (mg/mmol) | (mg/g) | Terms |
| A1 | <3 | <3 | <30 | Normal to mildly increased |
| A2 | 30-300 | 3-30 | 30-300 | Moderately increased |
| A3 | >300 | >30 | >300 | Severely increased | more coatings. The term "tablet" also comprises mini, melt, chewable, effervescent and orally disintegrating tablets.

The terms "pharmacopoe" and "pharmacopoeias" refer to standard pharmacopoeias such as the "USP 31-NF 26 through Second Supplement" (United States Pharmacopeial Convention) or the "European Pharmacopoeia 6.3" (European Directorate for the Quality of Medicines and Health Care, 2000-2009).

DETAILED DESCRIPTION OF THE INVENTION

In one aspect, the present invention relates to certain SGLT-2 inhibitors, for example empagliflozin, for use in treating, preventing, protecting against, reducing the risk of, delaying the occurrence of and/or delaying the progression of chronic kidney disease in patients, for example patients with prediabetes, type 1 or type 2 diabetes mellitus.

In a further aspect, the present invention relates to certain SGLT-2 inhibitors, for example empagliflozin, for use in treating, preventing, protecting against or delaying new onset of albuminuria in patients.

In a further aspect, the present invention relates to certain SGLT-2 inhibitors, for example empagliflozin, for use in treating, preventing, protecting against or delaying the progression from no albuminuria to micro- or macroalbuminuria in a patient at risk for renal disease.

In a further aspect, the present invention relates to certain SGLT-2 inhibitors, for example empagliflozin, for use in treating, preventing, protecting against or delaying the progression from microalbuminuria to macroalbuminuria in a patient with chronic kidney disease.

In a further aspect, the present invention relates to certain SGLT-2 inhibitors, for example empagliflozin, for use in treating, preventing, protecting against or delaying the progression of chronic kidney disease in a patient with chronic kidney disease.

In a further aspect, the present invention relates to certain SGLT-2 inhibitors, for example empagliflozin, for use in treating, preventing, protecting against or delaying the occurrence of:
- new onset of albuminuria,
- doubling of serum creatinine level accompanied by an eGFR (based on modification of diet in renal disease (MDRD) formula)≤45 mL/min/1.73m$^2$,
- need for continuous renal replacement therapy, or
- death due to renal disease.

In one aspect, a patient according of the present invention is a patient with prediabetes, type 1 or type 2 diabetes mellitus. In one aspect, a patient according to the present invention is a patient is a patient at risk for renal disease. In one aspect, a patient according to the present invention is a patient with or at risk of a cardiovascular disease. In one aspect, a patient according to the present invention is a patient with prediabetes, type 1 or type 2 diabetes mellitus and with or at risk of a cardiovascular disease.

In one aspect of the present invention, in a method or use disclosed herein a patient is a patient with obesity-related Glomerulopathy, a patient with perihilar fokal-segmental glomerulosclerosis or a patient with IgA nephropathy.

Accordingly, in one embodiment, the present invention provides a method of treating, preventing, protecting against, reducing the risk of, delaying the occurrence of and/or delaying the progression of chronic kidney disease in a patient with obesity-related Glomerulopathy, in a patient with perihilar fokal-segmental glomerulosclerosis or in a patient with IgA nephropathy.

SGLT2 inhibitors (sodium-glucose co-transporter 2) represent a novel class of agents that are being developed for the treatment or improvement in glycemic control in patients with type 2 diabetes. Glucopyranosyl-substituted benzene derivative are described as SGLT2 inhibitors, for example in WO 01/27128, WO 03/099836, WO 2005/092877, WO 2006/034489, WO 2006/064033, WO 2006/117359, WO 2006/117360, WO 2007/025943, WO 2007/028814, WO 2007/031548, WO 2007/093610, WO 2007/128749, WO 2008/049923, WO 2008/055870, WO 2008/055940. The glucopyranosyl-substituted benzene derivatives are proposed as inducers of urinary sugar excretion and as medicaments in the treatment of diabetes.

Renal filtration and reuptake of glucose contributes, among other mechanisms, to the steady state plasma glucose concentration and can therefore serve as an antidiabetic target. Reuptake of filtered glucose across epithelial cells of the kidney proceeds via sodium-dependent glucose cotransporters (SGLTs) located in the brush-border membranes in the tubuli along the sodium gradient. There are at least 3 SGLT isoforms that differ in their expression pattern as well as in their physico-chemical properties. SGLT2 is exclusively expressed in the kidney, whereas SGLT1 is expressed additionally in other tissues like intestine, colon, skeletal and cardiac muscle. SGLT3 has been found to be a glucose sensor in interstitial cells of the intestine without any transport function. Potentially, other related, but not yet characterized genes, may contribute further to renal glucose reuptake. Under normoglycemia, glucose is completely reabsorbed by SGLTs in the kidney, whereas the reuptake capacity of the kidney is saturated at glucose concentrations higher than 10 mM, resulting in glucosuria ("diabetes mellitus"). This threshold concentration can be decreased by SGLT2-inhibition. It has been shown in experiments with the SGLT inhibitor phlorizin that SGLT-inhibition will partially inhibit the reuptake of glucose from the glomerular filtrate into the blood leading to a decrease in blood glucose concentration and to glucosuria.

Empagliflozin is a novel SGLT2 inhibitor that is described for the treatment or improvement in glycemic control in patients with type 2 diabetes mellitus, for example in WO 05/092877, WO 06/117359, WO 06/120208, WO 2010/092126, WO 2010/092123, WO 2011/039107, WO 2011/039108.

Accordingly, in a particular embodiment, a SGLT-2 inhibitor within the meaning of this invention is empagliflozin.

Further, the present invention relates to therapeutic (treatment or prevention) methods as described herein, in particular methods for the prevention or treatment of renal diseases, said method comprising administering an effective amount of a SGLT-2 inhibitor as described herein and, optionally, one or more other active or therapeutic agents as described herein to the patient in need thereof.

Chronic kidney disease (CKD), also known as chronic renal disease, is a progressive loss in renal function over a period of months or years. Patients with renal disease, renal dysfunction or renal impairment may include patients with chronic renal insufficiency or impairment, which can be stratified (if not otherwise noted) according to glomerular filtration rate (GFR, ml/min/1.73m$^2$) into 5 disease stages: stage 1 characterized by normal GFR≥90 plus either persistent albuminuria (e.g. UACR≥30 mg/g) or known structural or hereditary renal disease; stage 2 characterized by mild reduction of GFR (GFR 60-89) describing mild renal impairment; stage 3 characterized by moderate reduction of GFR (GFR 30-59) describing moderate renal impairment;

stage 4 characterized by severe reduction of GFR (GFR 15-29) describing severe renal impairment; and terminal stage 5 characterized by requiring dialysis or GFR<15 describing established kidney failure (end-stage renal disease, ESRD).

Chronic kidney disease and its stages (CKD 1-5) can be usually characterized or classified accordingly, such as based on the presence of either kidney damage (albuminuria) or impaired estimated glomerular filtration rate (GFR<60 [ml/min/1.73m$^2$], with or without kidney damage).

For the purpose of the present invention, the estimated glomerular filtration rate (eGFR) is derived from the serum creatinine (SCr) value based on the MDRD formula below:

$$eGFR\ (mL/min/1.73m2)=175\times[SCr\ (\mu mol/L)/88.4]-1.154\times[age]-0.203\times[0.742\ if\ patient\ is\ female]\times[1.212\ if\ patient\ is\ of\ African\ origin]$$

For additional analyses, renal function can also be classified by the estimated creatinine clearance rate (eCCr) value, based on the Cockcroft-Gault formula below:

$$eCCr\ (mL/min)=(140-age)\times(weight\ in\ kg)\times[0.85\ if\ patient\ is\ female]/(72\times SCr\ (mg/dL))$$

Renal function classification based on eCCr is similar to the eGFR classification: normal renal function (≥90 mL/min), mild impairment (60 to<90 mL/min), moderate impairment (30 to<60 mL/min), and severe impairment (≥15 to<30 mL/min).

Generally, mild renal impairment according to the present invention corresponds to stage 2 chronic kidney disease, moderate renal impairment according to the present invention generally corresponds to stage 3 chronic kidney disease, and severe renal impairment according to the present invention generally corresponds to stage 4 chronic kidney disease. Likewise, moderate A renal impairment according to the present invention generally corresponds to stage 3A chronic kidney disease and moderate B renal impairment according to the present invention generally corresponds to stage 3B chronic kidney disease.

Accordingly, in one aspect, the present invention relates to certain SGLT-2 inhibitors, for example empagliflozin, for use in treating, preventing, protecting against or delaying the progression of chronic kidney disease in a patient, in particular a patient according to the present invention, for example the progression from stage 1 chronic kidney disease to stage 2 chronic kidney disease, for example the progression from stage 2 chronic kidney disease to stage 3 chronic kidney disease, for example the progression from stage 3 chronic kidney disease to stage 4 chronic kidney disease, for example the progression from stage 4 chronic kidney disease to stage 5 chronic kidney disease.

In a further aspect of the present invention, the progression of chronic kidney disease in a patient is for example the progression from stage 2 chronic kidney disease to stage 3A chronic kidney disease, for example the progression from stage 3A chronic kidney disease to stage 3B chronic kidney disease, for example the progression from stage 3B chronic kidney disease to stage 4 chronic kidney disease.

In a further aspect of the present invention, the progression of chronic kidney disease in a patient is for example the progression from stage 2 chronic kidney disease to stage 4 or 5 chronic kidney disease, for example the progression from stage 3 chronic kidney disease to stage 5 chronic kidney disease, for example the progression from stage 3A or 3B chronic kidney disease to stage 5 chronic kidney disease.

In a further aspect, a patient with chronic kidney disease according to the present invention is a patient with stage 1 chronic kidney disease, stage 2 chronic kidney disease, stage 3 chronic kidney disease, stage 4 chronic kidney disease, or stage 5 chronic kidney disease. In a further aspect, a patient with chronic kidney disease according to the present invention is a patient with stage 3A chronic kidney disease or stage 3B chronic kidney disease, In some aspects, renal disease, renal dysfunction, or insufficiency or impairment of renal function (including mild, moderate and/or severe renal impairment) may also be suggested (if not otherwise noted) by elevated serum creatinine levels (e.g. serum creatinine levels above the upper limit of normal for their age, e.g.≥130-150 μmol/l, or≥1.5 mg/dl (≥136 μmol/l) in men and≥1.4 mg/dl (≥124 μmol/l) in women) or abnormal creatinine clearance (e.g. glomerular filtration rate (GFR)≤30-60 ml/min).

In some further aspects, mild renal impairment may be also suggested (if not otherwise noted) by a creatinine clearance of 50-80 ml/min (approximately corresponding to serum creatine levels of≤1.7 mg/dL in men and≤1.5 mg/dL in women); moderate renal impairment may be e.g. suggested (if not otherwise noted) by a creatinine clearance of 30-50 ml/min (approximately corresponding to serum creatinine levels of>1.7 to≤3.0 mg/dL in men and>1.5 to≤2.5 mg/dL in women); and severe renal impairment may be e.g. suggested (if not otherwise noted) by a creatinine clearance of<30 ml/min (approximately corresponding to serum creatinine levels of>3.0 mg/dL in men and>2.5 mg/dL in women). Patients with end-stage renal disease require dialysis (e.g. hemodialysis or peritoneal dialysis).

In some further aspects, albuminuria can also be a sign of kidney disease. Albuminuria stages may be classified as disclosed herein, and patients may be stratified in category A1, which reflects no albuminuria, category A2, which reflects microalbuminuria, and category A3, which reflects macroalbuminuria.

Accordingly, in a further aspect, a patient with chronic kidney disease according to the present invention is a patient with microalbuminuria or with macroalbuminuria.

In one aspect of the present invention, it has been found that empagliflozin has nephroprotective properties, in particular as described herein. In particular, it has been shown that administration of empagliflozin has the property to maintain or improve renal function over time in certain patient group, for example as described herein, as demonstrated after discontinuation of administration of empagliflozin.

In one aspect, a patient in the context of the present invention is a patient at risk of renal disease. A patient at risk of renal disease is for example a patient with at least one of the following:

prediabetes, type 1 or 2 diabetes mellitus,
hypertension,
metabolic syndrome,
cardiovascular disease.

In one aspect, a patient in the context of the present invention is a patient with prediabetes, type 1 or 2 diabetes mellitus.

Type 2 diabetes mellitus is a common chronic and progressive disease arising from a complex pathophysiology involving the dual endocrine effects of insulin resistance and impaired insulin secretion with the consequence not meeting the required demands to maintain plasma glucose levels in the normal range. This leads to hyperglycaemia and its associated micro- and macrovascular complications or chronic damages, such as e.g. diabetic nephropathy, retinopathy or neuropathy, or macrovascular (e.g. cardiovascular) complications. The vascular disease component plays a significant role, but is not the only factor in the spectrum of diabetes associated disorders. The high frequency of complications leads to a significant reduction of life expectancy. Diabetes is currently the most frequent cause of adult-onset loss of vision, renal failure, and amputation in the Industrialised World because of diabetes induced complications and is associated with a two to five fold increase in cardiovascular disease risk. Type 1 diabetes mellitus (Type 1 diabetes), also called insulin dependent diabetes mellitus or juvenile diabetes, is a form of diabetes mellitus that results from autoimmune destruction of insulin-producing beta cells of the pancreas. The subsequent lack of insulin leads to increased blood glucose concentrations and increased urinary glucose excretion. The classical symptoms are polyuria, polydipsia, polyphagia, and weight loss. Type 1 diabetes may be fatal unless treated with insulin. Complications from type 1 diabetes are the same or similar to complications from type 2 diabetes.

Large randomized studies have established that intensive and tight glycemic control during early (newly diagnoses to 5 years) stage diabetes has enduring beneficial effects and reduces the risk of diabetic complications, both micro- and macrovascular. However, many patients with diabetes still develop diabetic complications despite receiving intensified glycemic control.

Standard therapy of type 1 diabetes is insulin treatment. Therapies for type 1 diabetes are for example described in WO 2012/062698.

The treatment of type 2 diabetes typically begins with diet and exercise, followed by oral antidiabetic monotherapy, and although conventional monotherapy may initially control blood glucose in some patients, it is however associated with a high secondary failure rate. The limitations of single-agent therapy for maintaining glycemic control may be overcome, at least in some patients, and for a limited period of time by combining multiple drugs to achieve reductions in blood glucose that cannot be sustained during long-term therapy with single agents. Available data support the conclusion that in most patients with type 2 diabetes current monotherapy will fail and treatment with multiple drugs will be required. But, because type 2 diabetes is a progressive disease, even patients with good initial responses to conventional combination therapy will eventually require an increase of the dosage or further treatment with insulin because the blood glucose level is very difficult to maintain stable for a long period of time. Although existing combination therapy has the potential to enhance glycemic control, it is not without limitations (especially with regard to long term efficacy). Further, traditional therapies may show an increased risk for side effects, such as hypoglycemia or weight gain, which may compromise their efficacy and acceptability.

Oral antidiabetic drugs conventionally used in therapy (such as e.g. first- or second-line, and/or mono- or (initial or add-on) combination therapy) include, without being restricted thereto, metformin, sulphonylureas, thiazolidinediones, DPP-4 inhibitors, glinides and α-glucosidase inhibitors.

Non-oral (typically injected) antidiabetic drugs conventionally used in therapy (such as e.g. first- or second-line, and/or mono- or (initial or add-on) combination therapy) include, without being restricted thereto, GLP-1 or GLP-1 analogues, and insulin or insulin analogues.

The SGLT2 inhibitor therein also exhibits a very good efficacy with regard to glycemic control, in particular in view of a reduction of fasting plasma glucose, postprandial plasma glucose and/or glycosylated hemoglobin (HbA1c). By administering a pharmaceutical composition according to this invention, a reduction of HbA1c equal to or greater than preferably 0.5%, even more preferably equal to or greater than 1.0% can be achieved and the reduction is particularly in the range from 1.0% to 2.0%.

In a further embodiment, a patient according to the present invention is a patient who shows one, two or more of the following conditions:
(a) a fasting blood glucose or serum glucose concentration greater than 100 mg/dL, in particular greater than 125 mg/dL;
(b) a postprandial plasma glucose equal to or greater than 140 mg/dL;
(c) an HbA1c value equal to or greater than 6.5%, in particular equal to or greater than 7.0%, especially equal to or greater than 7.5%, even more particularly equal to or greater than 8.0%.

In a further embodiment, a patient according to the present invention is a patient who shows one, two or more of the following conditions:
(a) insufficient glycemic control with diet and exercise alone;
(b) insufficient glycemic control despite oral monotherapy with metformin, in particular despite oral monotherapy at a maximal tolerated dose of metformin;
(c) insufficient glycemic control despite oral monotherapy with one or more other antidiabetic agent, in particular despite oral monotherapy at a maximal tolerated dose of the other antidiabetic agent.

In a further embodiment, a patient according to the present invention is a patient who shows one, two or more of the following conditions:
(a) obesity (including class I, II and/or III obesity), visceral obesity and/or abdominal obesity,
(b) triglyceride blood level≥150 mg/dL,
(c) HDL-cholesterol blood level<40 mg/dL in female patients and<50 mg/dL in male patients,
(d) a systolic blood pressure≥130 mm Hg and a diastolic blood pressure≥85 mm Hg,
(e) a systolic blood pressure≥130 mm Hg and a diastolic blood pressure≥80 mm Hg,
(f) a fasting blood glucose level≥100 mg/dL.

In one embodiment, a patient according to the present invention is a patient with prediabetes, type 1 or 2 diabetes mellitus and hypertension. In one embodiment, a patient according to the present invention is a patient with prediabetes, type 1 or 2 diabetes mellitus and a systolic blood pressure≥130 mm Hg and a diastolic blood pressure≥80 mm Hg.

In one embodiment, diabetes patients within the meaning of this invention may include patients who have not previously been treated with an antidiabetic drug (drug-naïve patients). Thus, in an embodiment, the therapies described herein may be used in naïve patients. In another embodiment, diabetes patients within the meaning of this invention may include patients with advanced or late stage type 2 diabetes mellitus (including patients with failure to conventional antidiabetic therapy), such as e.g. patients with inadequate glycemic control on one, two or more conventional oral and/or non-oral antidiabetic drugs as defined herein, such as e.g. patients with insufficient glycemic control despite (mono-)therapy with metformin, a thiazolidinedione (particularly pioglitazone), a sulphonylurea, a glinide, a DPP-4 inhibitor, GLP-1 or GLP-1 analogue, insulin or insulin analogue, or an α-glucosidase inhibitor, or despite dual combination therapy with metformin/sulphonylurea, metformin/thiazolidinedione (particularly pioglitazone), metformin/DPP-4 inhibitor, sulphonylurea/ α-glucosidase inhibitor, pioglitazone/sulphonylurea, metformin/insulin, pioglitazone/insulin or sulphonylurea/insulin.

In one embodiment, a patient according to the present invention is a patient receiving treatment with a non-oral antidiabetic drug, for example GLP1- analog (for example short acting GLP-1 analog such as exenatide, liraglutide or lixisenatide, or long-acting GLP-1 analog such as exenatide extended-release, albiglutide or dulaglutide), for example insulin or insulin analogue, for example basal insulin, such as glargine, detemir and/or NPH insulin.

In one embodiment, a patient according to the present invention is a patient receiving treatment with insulin or insulin analogue. An insulin or insulin analogue may include normal insulin, human insulin, insulin derivatives, zinc insulins and insulin analogues, including formulations thereof with modified release profiles, in particular as used in the therapy of humans. The insulin may be selected from the group consisting of:
rapid-acting insulins,
short-acting insulins,
intermediate-acting insulins,
long-acting insulins,
and mixtures thereof.

Mixtures of insulins may comprise mixtures of short- or rapid-acting insulins with long-acting insulins. For example such mixtures are marketed as Actraphane/Mixtard or Novomix.

The term "insulin" in the scope of the present invention covers insulins as described hereinbefore and hereinafter which are administered to the patient via injection, preferably subcutaneous injection, via infusion, including pumps, via inhalation or other routes of administration. Insulins to be administered via inhalation are for example Exubera (Pfizer), AIR (Lilly) and AER (Novo Nordisk).

Rapid-acting insulins usually start lowering the blood glucose within about 5 to 15 minutes and are effective for about 3 to 4 hours. Examples of rapid-acting insulins are insulin aspart, insulin lispro and insulin glulisine. Insulin Lispro is marketed under the trade name Humalog and Liprolog. Insulin Aspart is marketed under the trade names NovoLog and NovoRapid. Insulin glulisine is marketed under the trade name Apidra.

Short-acting insulins usually start lowering the blood glucose within about 30 minutes and are effective about 5 to 8 hours. An example is regular insulin or human insulin.

Intermediate-acting insulins usually start lowering the blood glucose within about 1 to 3 hours and are effective for about 16 to 24 hours. An example is NPH insulin, also known as Humulin N, Novolin N, Novolin NPH and isophane insulin. Another example are lente insulins, such as Semilente or Monotard.

Long-acting insulins usually start lowering the blood glucose within 1 to 6 hours and are effective for up to about 24 hours or even up to or beyond 32 hours. Long-acting insulin usually provides a continuous level of insulin activity (for up to 24-36 hours) and usually operates at a maximum strength (with flat action profile) after about 8-12 hours, sometimes longer. Long-acting insulin is usually administered in the morning or before bed. Examples of long-acting insulin may include, but are not limited to, insulin glargine, insulin detemir or insulin degludec, which are insulin analogues, and ultralente insulin, which is regular human insulin formulated for slow absorption. Long-acting insulin is suited to provide for basal, as opposed to prandial, insulin requirements (e.g. to control hyperglycemia). Long-acting insulin may be typically administered ranging from twice or once daily, over thrice weekly up to once weekly (ultra long-acting insulin). Insulin glargine is marketed under the trade name Lantus for example. Insulin detemir is marketed under the tradename Levemir for example.

In one embodiment, a long-acting insulin is an acylated derivative of human insulin. Acylated insulin derivatives may be such wherein a lipophilic group is attached to the lysine residue in position B29. A commercial product is Levemir® comprising $Lys^{B29}(N^{\varepsilon}$-tetradecanoyl) des(B30) human insulin (insulin detemir). Another example is $N^{\varepsilon B29}$-$(N^{\alpha}$-(ω-carboxypentadecanoyl)-L-γ-glutamyl) des(B30) human insulin (insulin degludec).

In one embodiment, a long-acting insulin is such comprising positively charged amino acids such as Arg attached to the C-terminal end of the B-chain. A commercial product is Lantus® (insulin glargine) comprising $Gly^{A21}$, $Arg^{B31}$, $Arg^{B32}$ human insulin.

In one embodiment, a patient according to the present invention is a patient receiving treatment with a mixture of insulin and GLP-1 analog, for example a mixture of insulin glargine and lixisenatide.

In a further aspect, a patient according to the present invention is a patient with or at risk of a cardiovascular disease.

In one embodiment, the patient is a patient with one or more cardiovascular risk factors selected from A), B), C) and D), for example a patient with type 1 or type 2 diabetes mellitus or with pre-diabetes with one or more cardiovascular risk factors selected from A), B), C) and D):
A) previous or existing vascular disease selected from myocardial infarction, coronary artery disease, percutaneous coronary intervention, coronary artery by-pass grafting, ischemic or hemorrhagic stroke, congestive heart failure, and peripheral occlusive arterial disease,
B) advanced age>/=60-70 years, and
C) one or more cardiovascular risk factors selected from
  advanced type 2 diabetes mellitus>10 years duration,
  hypertension,
  current daily cigarette smoking,
  dyslipidemia,
  obesity,
  age>/=40,
  metabolic syndrome, hyperinsulinemia or insulin resistance, and
  hyperuricemia, erectile dysfunction, polycystic ovary syndrome, sleep apnea, or family history of vascular disease or cardiomyopathy in first-degree relative;
D) one or more of the following:
  confirmed history of myocardial infarction,
  unstable angina with documented multivessel coronary disease or positive stress test,
  multivessel Percutaneous Coronary Intervention,
  multivessel Coronary Artery By-pass Grafting (CABG),
  history of ischemic or hemorrhagic stroke,
  peripheral occlusive arterial disease.

In a further aspect of the present invention, a patient having cardiovascular disease is defined as having at least one of the following:
  Confirmed history of myocardial infarction; or
  Evidence of multivessel coronary artery disease, in 2 or more major coronary arteries, irrespective of the revascularization status, i.e.
    a) Either the presence of a significant stenosis (imaging evidence of at least 50% narrowing of the luminal diameter measured during a coronary angiography or a multi-sliced computed tomography angiography), in 2 or more major coronary arteries,
b) Or a previous revascularisation (percutaneous transluminal coronary angioplasty with or without stent, or coronary artery bypass grafting), in 2 or more major coronary arteries,
c) Or the combination of previous revascularisation in one major coronary artery (percutaneous transluminal coronary angioplasty with or without stent, or coronary artery bypass grafting), and the presence of a significant stenosis in another major coronary artery (imaging evidence of at least 50% narrowing of the luminal diameter measured during a coronary angiography or a multi-sliced computed tomography angiography),
Note: A disease affecting the left main coronary artery is considered as a 2-vessel disease.

Evidence of a single vessel coronary artery disease with:
a) The presence of a significant stenosis i.e. the imaging evidence of at least 50% narrowing of the luminal diameter of one major coronary artery in patients not subsequently successfully revascularised (measured during a coronary angiography or a multi-sliced computed tomography angiography)
b) And at least one of the following (either (i) or (ii)):
  i. A positive non invasive stress test, confirmed by either:
    1. A positive exercise tolerance test in patients without a complete left bundle branch block, Wolff-Parkinson-White syndrome, or paced ventricular rhythm, or
    2. A positive stress echocardiography showing regional systolic wall motion abnormalities, or
    3. A positive scintigraphic test showing stress-induced ischemia, i.e. the development of transient perfusion defects during myocardial perfusion imaging;
  ii. Or patient discharged from hospital with a documented diagnosis of unstable angina within 12 months prior to selection.

Episode of unstable angina with confirmed evidence of coronary multivessel or single vessel disease as defined above.
History of ischemic or haemorrhagic stroke
Presence of peripheral artery disease (symptomatic or not) documented by either: previous limb angioplasty, stenting or bypass surgery; or previous limb or foot amputation due to circulatory insufficiency; or angiographic evidence of significant (>50%) peripheral artery stenosis in at least one limb; or evidence from a non-invasive measurement of significant (>50% or as reported as hemodynamically significant) peripheral artery stenosis in at least one limb; or ankle brachial index of<0.9 in at least one limb.

In a further aspect of the present invention, a patient having cardiovascular disease is defined as having at least one of the following:
a) Confirmed history of myocardial infarction,
b) Unstable angina with documented multivessel coronary disease (at least two major coronary arteries in angiogram) or positive stress test (ST segment depression>=2 mm or a positive nuclear perfusion scintigram),
c) Multivessel Percutaneous Coronary Intervention (PCI),
d) Multivessel Coronary Artery By-pass Grafting (CABG), including with recurrent angina following surgery,
e) History of ischemic or hemorrhagic stroke,
f) Peripheral occlusive arterial disease (previous limb bypass surgery or percutaneous transluminal angioplasty; previous limb or foot amputation due to circulatory insufficiency, angiographic or imaging detected (for example: ultrasound, Magnetic Resonance Imaging) significant vessel stenosis of major limb arteries).

Accordingly, in one aspect, the present invention relates to a certain SGLT-2 inhibitor, in particular empagliflozin, for use in a method as described herein, in a patient with one or more risk factors selected from A), B), C) and D):
A) previous or existing vascular disease (such as e.g. myocardial infarction (e.g. silent or non-silent), coronary artery disease, percutaneous coronary intervention, coronary artery by-pass grafting, ischemic or hemorrhagic stroke, congestive heart failure (e.g. NYHA class I, II, III or IV, e.g. left ventricular function<40%), or peripheral occlusive arterial disease),
B) advanced age (such as e.g. age>/=60-70 years), and
C) one or more cardiovascular risk factors selected from
advanced type 1 or type 2 diabetes mellitus (such as e.g.>10 years duration),
hypertension (such as e.g.>130/80 mm Hg, or systolic blood pressure>140 mmHg or on at least one blood pressure lowering treatment),
current daily cigarette smoking,
dyslipidemia (such as e.g. atherogenic dyslipidemia, postprandial lipemia, or high level of LDL cholesterol (e.g. LDL cholesterol>/=130-135 mg/dL), low level of HDL cholesterol (e.g.<35-40 mg/dL in men or<45-50 mg/dL in women) and/or high level of triglycerides (e.g.>200-400 mg/dL) in the blood, or on at least one treatment for lipid abnormality), - obesity (such as e.g. abdominal and/or visceral obesity, or body mass index>/=45 kg/m2),
age>/=40,
metabolic syndrome, hyperinsulinemia or insulin resistance, and
hyperuricemia, erectile dysfunction, polycystic ovary syndrome, sleep apnea, or family history of vascular disease or cardiomyopathy in first-degree relative,
D) one or more of the following:
confirmed history of myocardial infarction,
unstable angina with documented multivessel coronary disease or positive stress test,
multivessel Percutaneous Coronary Intervention,
multivessel Coronary Artery By-pass Grafting (CABG),
history of ischemic or hemorrhagic stroke,
peripheral occlusive arterial disease.
said method comprising administering a therapeutically effective amount of the SGLT-2 inhibitor, optionally in combination with one or more other therapeutic substances, to the patient.

In one aspect, a patient in the context of the present invention is a patient with hypertension. In one aspect, a patient in the context of the present invention is a patient with metabolic syndrome.

The present invention further relates to a pharmaceutical composition comprising a certain SGLT-2 inhibitor as defined herein, empagliflozin, for use in the therapies described herein, for example in a patient or patient group as described herein.

When this invention refers to patients requiring treatment or prevention, it relates primarily to treatment and prevention in humans, but the pharmaceutical composition may also be used accordingly in veterinary medicine in mammals. In the scope of this invention adult patients are preferably humans of the age of 18 years or older. Also in the scope of this invention, patients are adolescent humans, i.e. humans of age 10 to 17 years, preferably of age 13 to 17 years.

In a further aspect, a method according to the present invention further comprises improving glycemic control in patients having type 1 or type 2 diabetes mellitus or showing first signs of pre-diabetes.

In a further aspect, a method according to the present invention further comprises improving glycemic control and/or for reducing of fasting plasma glucose, of postprandial plasma glucose and/or of glycosylated hemoglobin HbA1c in a patient in need thereof who is diagnosed with impaired glucose tolerance (IGT), impaired fasting blood glucose (IFG) with insulin resistance, with metabolic syndrome and/or with type 2 or type 1 diabetes mellitus.

In a further aspect, a method according to the present invention further comprises improving glycemic control in patients, in particular in adult patients, with type 2 diabetes mellitus as an adjunct to diet and exercise.

Within the scope of the present invention it has now been found that certain SGLT-2 inhibitors as defined herein, optionally in combination with one or more other therapeutic substances (e.g. selected from those described herein), as well as pharmaceutical combinations, compositions or combined uses according to this invention of such SGLT-2 inhibitors as defined herein have properties, which make them suitable for the purpose of this invention and/or for fulfilling one or more of above needs. The present invention thus relates to a certain SGLT-2 inhibitor as defined herein, preferably empagliflozin, for use in the therapies described herein.

Furthermore, it can be found that the administration of a pharmaceutical composition according to this invention results in no risk or in a low risk of hypoglycemia. Therefore, a treatment or prophylaxis according to this invention is also advantageously possible in those patients showing or having an increased risk for hypoglycemia.

It will be appreciated that the amount of the pharmaceutical composition according to this invention to be administered to the patient and required for use in treatment or prophylaxis according to the present invention will vary with the route of administration, the nature and severity of the condition for which treatment or prophylaxis is required, the age, weight and condition of the patient, concomitant medication and will be ultimately at the discretion of the attendant physician. In general, however, the SGLT2 inhibitor according to this invention is included in the pharmaceutical composition or dosage form in an amount sufficient that by its administration the glycemic control in the patient to be treated is improved.

In the following preferred ranges of the amount of the SGLT2 inhibitor to be employed in the pharmaceutical composition and the methods and uses according to this invention are described. These ranges refer to the amounts to be administered per day with respect to an adult patient, in particular to a human being, for example of approximately 70 kg body weight, and can be adapted accordingly with regard to an administration 2, 3, 4 or more times daily and with regard to other routes of administration and with regard to the age of the patient. Within the scope of the present invention, the pharmaceutical composition is preferably administered orally. Other forms of administration are possible and described hereinafter. Preferably the one or more dosage forms comprising the SGLT2 inhibitor is oral or usually well known.

In general, the amount of the SGLT2 inhibitor in the pharmaceutical composition and methods according to this invention is preferably the amount usually recommended for a monotherapy using said SGLT2 inhibitor.

The preferred dosage range of the SGLT2 inhibitor is in the range from 0.5 mg to 200 mg, even more preferably from 1 to 100 mg, most preferably from 1 to 50 mg per day. In one aspect, a preferred dosage of the SGLT2 inhibitor empagliflozin is 10 mg or 25 mg per day. The oral administration is preferred. Therefore, a pharmaceutical composition may comprise the hereinbefore mentioned amounts, in particular from 1 to 50 mg or 1 to 25 mg. Particular dosage strengths (e.g. per tablet or capsule) are for example 1, 2.5, 5, 7.5, 10, 12.5, 15, 20, 25 or 50 mg of the SGLT2 inhibitor, in particular empagliflozin. In one aspect, a pharmaceutical composition comprises 10 mg or 25 mg of empagliflozin. The application of the active ingredient may occur up to three times a day, preferably one or two times a day, most preferably once a day.

A pharmaceutical composition which is present as a separate or multiple dosage form, preferably as a kit of parts, is useful in combination therapy to flexibly suit the individual therapeutic needs of the patient.

According to a first embodiment a preferred kit of parts comprises a containment containing a dosage form comprising the SGLT2 inhibitor and at least one pharmaceutically acceptable carrier.

A further aspect of the present invention is a manufacture comprising the pharmaceutical composition being present as separate dosage forms according to the present invention and a label or package insert comprising instructions that the separate dosage forms are to be administered in combination or alternation.

According to a first embodiment a manufacture comprises (a) a pharmaceutical composition comprising a SGLT2 inhibitor according to the present invention and (b) a label or package insert which comprises instructions that the medicament is to be administered.

The desired dose of the pharmaceutical composition according to this invention may conveniently be presented in a once daily or as divided dose administered at appropriate intervals, for example as two, three or more doses per day.

The pharmaceutical composition may be formulated for oral, rectal, nasal, topical (including buccal and sublingual), transdermal, vaginal or parenteral (including intramuscular, sub-cutaneous and intravenous) administration in liquid or solid form or in a form suitable for administration by inhalation or insufflation. Oral administration is preferred. The formulations may, where appropriate, be conveniently presented in discrete dosage units and may be prepared by any of the methods well known in the art of pharmacy. All methods include the step of bringing into association the active ingredient with one or more pharmaceutically acceptable carriers, like liquid carriers or finely divided solid carriers or both, and then, if necessary, shaping the product into the desired formulation.

The pharmaceutical composition may be formulated in the form of tablets, granules, fine granules, powders, capsules, caplets, soft capsules, pills, oral solutions, syrups, dry syrups, chewable tablets, troches, effervescent tablets, drops, suspension, fast dissolving tablets, oral fast-dispersing tablets, etc.

The pharmaceutical composition and the dosage forms preferably comprises one or more pharmaceutical acceptable carriers which must be "acceptable" in the sense of being compatible with the other ingredients of the formulation and not deleterious to the recipient thereof. Examples of pharmaceutically acceptable carriers are known to the one skilled in the art.

Pharmaceutical compositions suitable for oral administration may conveniently be presented as discrete units such as capsules, including soft gelatin capsules, cachets or tablets each containing a predetermined amount of the active ingredient; as a powder or granules; as a solution, a suspension or as an emulsion, for example as syrups, elixirs or self-emulsifying delivery systems (SEDDS). The active ingredients may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The pharmaceutical composition according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilisation from solution, for constitution with a suitable vehicle, e.g. sterile, pyrogen-free water, before use.

Pharmaceutical compositions suitable for rectal administration wherein the carrier is a solid are most preferably presented as unit dose suppositories. Suitable carriers include cocoa butter and other materials commonly used in the art, and the suppositories may be conveniently formed by admixture of the active compound(s) with the softened or melted carrier(s) followed by chilling and shaping in moulds.

The pharmaceutical compositions and methods according to this invention show advantageous effects in the treatment and prevention of those diseases and conditions as described hereinbefore. Advantageous effects may be seen for example with respect to efficacy, dosage strength, dosage frequency, pharmacodynamic properties, pharmacokinetic properties, fewer adverse effects, convenience, compliance, etc.

Methods for the manufacture of SGLT2 inhibitors according to this invention and of prodrugs thereof are known to the one skilled in the art. Advantageously, the compounds according to this invention can be prepared using synthetic methods as described in the literature, including patent applications as cited hereinbefore. Preferred methods of manufacture are described in the WO 2006/120208 and WO 2007/031548. With regard to empagliflozin an advantageous crystalline form is described in the international patent application WO 2006/117359 which hereby is incorporated herein in its entirety.

The active ingredients may be present in the form of a pharmaceutically acceptable salt. Pharmaceutically acceptable salts include, without being restricted thereto, such as salts of inorganic acid like hydrochloric acid, sulfuric acid and phosphoric acid; salts of organic carboxylic acid like oxalic acid, acetic acid, citric acid, malic acid, benzoic acid, maleic acid, fumaric acid, tartaric acid, succinic acid and glutamic acid and salts of organic sulfonic acid like methanesulfonic acid and p-toluenesulfonic acid. The salts can be formed by combining the compound and an acid in the appropriate amount and ratio in a solvent and decomposer. They can be also obtained by the cation or anion exchange from the form of other salts.

The active ingredients or a pharmaceutically acceptable salt thereof may be present in the form of a solvate such as a hydrate or alcohol adduct.

Pharmaceutical compositions or combinations for use in these therapies comprising the SGLT-2 inhibitor as defined herein optionally together with one or more other active substances are also contemplated.

Further, the present invention relates to the SGLT-2 inhibitors, optionally in combination with one, two or more further active agents, each as defined herein, for use in the therapies as described herein.

Further, the present invention relates to the use of the SGLT-2 inhibitors, optionally in combination with one, two or more further active agents, each as defined herein, for preparing pharmaceutical compositions which are suitable for the treatment and/or prevention purposes of this invention.

The present invention further relates to a combination comprising a certain SGLT-2 inhibitor (particularly empagliflozin) and one or more other active substances selected from other antidiabetic substances, particularly for simultaneous, separate or sequential use in the therapies described herein.

The present invention further relates to a combination comprising a certain SGLT-2 inhibitor (particularly empagliflozin) and one or more other antidiabetics selected from the group consisting of metformin, a sulphonylurea, nateglinide, repaglinide, a thiazolidinedione, a PPAR-gamma-agonist, an alpha-glucosidase inhibitor, insulin or an insulin analogue, GLP-1 or a GLP-1 analogue and a DPP-4 inhibitor, particularly for simultaneous, separate or sequential use in the therapies described herein.

The present invention further relates to a method according to the present invention further comprising treating and/or preventing metabolic disorders, especially type 2 diabetes mellitus and/or conditions related thereto (e.g. diabetic complications) comprising the combined (e.g. simultaneous, separate or sequential) administration of an effective amount of empagliflozin and one or more other antidiabetics selected from the group consisting of metformin, a sulphonylurea, nateglinide, repaglinide, a PPAR-gamma-agonist, an alpha-glucosidase inhibitor, insulin or an insulin analogue, GLP-1 or a GLP-1 analogue and a DPP-4 inhibitor, to the patient (particularly human patient) in need thereof, such as e.g. a patient as described herein.

The present invention further relates to therapies or therapeutic methods described herein, further comprising treating and/or preventing metabolic disorders, especially type 2 diabetes mellitus and/or conditions related thereto (e.g. diabetic complications), comprising administering a therapeutically effective amount of empagliflozin and, optionally, one or more other therapeutic agents, such as e.g. antidiabetics selected from the group consisting of metformin, a sulphonylurea, nateglinide, repaglinide, a PPAR-gammaagonist, an alpha-glucosidase inhibitor, insulin or an insulin analogue, GLP-1 or a GLP-1 analogue and a DPP-4 inhibitor, to the patient (particularly human patient) in need thereof, such as e.g. a patient as described herein.

Unless otherwise noted, combination therapy may refer to first line, second line or third line therapy, or initial or add-on combination therapy or replacement therapy.

The present invention further relates to a certain SGLT-2 inhibitor as defined herein, preferably empagliflozin, in combination with metformin, for use in the therapies described herein.

Metformin is usually given in doses varying from about 500 mg to 2000 mg up to 2500 mg per day using various dosing regimens from about 100 mg to 500 mg or 200 mg to 850 mg (1-3 times a day), or about 300 mg to 1000 mg once or twice a day, or delayed-release metformin in doses of about 100 mg to 1000 mg or preferably 500 mg to 1000 mg once or twice a day or about 500 mg to 2000 mg once a day. Particular dosage strengths may be 250, 500, 625, 750, 850 and 1000 mg of metformin hydrochloride.

For children 10 to 16 years of age, the recommended starting dose of metformin is 500 mg given once daily. If this dose fails to produce adequate results, the dose may be increased to 500 mg twice daily. Further increases may be made in increments of 500 mg weekly to a maximum daily dose of 2000 mg, given in divided doses (e.g. 2 or 3 divided doses). Metformin may be administered with food to decrease nausea.

An example of a DPP-4 inhibitor is linagliptin, which is usually given in a dosage of 5 mg per day.

A dosage of pioglitazone is usually of about 1-10 mg, 15 mg, 30 mg, or 45 mg once a day.

Rosiglitazone is usually given in doses from 4 to 8 mg once (or divided twice) a day (typical dosage strengths are 2, 4 and 8 mg).

Glibenclamide (glyburide) is usually given in doses from 2.5-5 to 20 mg once (or divided twice) a day (typical dosage strengths are 1.25, 2.5 and 5 mg), or micronized glibenclamide in doses from 0.75-3 to 12 mg once (or divided twice) a day (typical dosage strengths are 1.5, 3, 4.5 and 6 mg).

Glipizide is usually given in doses from 2.5 to 10-20 mg once (or up to 40 mg divided twice) a day (typical dosage strengths are 5 and 10 mg), or extended-release glibenclamide in doses from 5 to 10 mg (up to 20 mg) once a day (typical dosage strengths are 2.5, 5 and 10 mg).

Glimepiride is usually given in doses from 1-2 to 4 mg (up to 8 mg) once a day (typical dosage strengths are 1, 2 and 4 mg).

The non-sulphonylurea insulin secretagogue nateglinide is usually given in doses from 60 to 120 mg with meals (up to 360 mg/day, typical dosage strengths are 60 and 120 mg); repaglinide is usually given in doses from 0.5 to 4 mg with meals (up to 16 mg/day, typical dosage strengths are 0.5, 1 and 2 mg). A dual combination of repaglinide/metformin is available in dosage strengths of 1/500 and 2/850 mg.

In one aspect of the present invention, the one or more other therapeutic substances are RAAS inhibitors (Renin-Angiotensin-Aldosterone System). In one aspect of the present invention, the one or more other therapeutic substances is a direct renin inhibitor, an Angiotensin-Converting Enzyme (ACE) inhibitor and/or an angiotensin II receptor blocker (ARB).

In one aspect, a SGLT-2 inhibitor, in particular empagliflozin is used in a method according to the present invention in addition to a RAAS inhibitor, in particular a direct renin inhibitor, an Angiotensin-Converting Enzyme (ACE) inhibitor and/or an angiotensin II receptor blocker (ARB).

In another embodiment of the present invention, certain SGLT-2 inhibitors, in particular empagliflozin, are useful in the therapy of a patient with chronic kidney disease and albuminuria despite therapy with a direct renin inhibitor, an angiotensin-converting enzyme (ACE) inhibitor and/or an angiotensin II receptor blocker (ARB), in particular a patient described herein.

In another embodiment of the present invention, certain a SGLT-2 inhibitors, in particular empagliflozin, are useful in a method according to the present invention on top of direct renin inhibitor therapy, angiotensin-converting enzyme (ACE) inhibitor therapy and/or angiotensin II receptor blockade (ARB) therapy.

Accordingly, in a further embodiment, the present invention relates to a certain SGLT-2 inhibitor, in particular empagliflozin, in combination with a RAAS inhibitor, for example a direct renin inhibitor, an Angiotensin-Converting Enzyme (ACE) inhibitor and/or an angiotensin II receptor blocker (ARB), for use in the therapy as described herein, for example in a patient as described herein.

In one aspect, the present invention relates to certain SGLT-2 inhibitors, for example empagliflozin, in combination with a RAAS inhibitor, for example a direct renin inhibitor, an Angiotensin-Converting Enzyme (ACE) inhibitor and/or an angiotensin II receptor blocker (ARB), for use in treating, preventing, protecting against, reducing the risk of, delaying the occurrence of and/or delaying the progression of chronic kidney disease in patients, for example patients with prediabetes, type 1 or type 2 diabetes mellitus.

In a further aspect, the present invention relates to certain SGLT-2 inhibitors, for example empagliflozin, in combination with a RAAS inhibitor, for example a direct renin inhibitor, an Angiotensin-Converting Enzyme (ACE) inhibitor and/or an angiotensin II receptor blocker (ARB), for use in treating, preventing, protecting against or delaying new onset of albuminuria in patients.

In a further aspect, the present invention relates to certain SGLT-2 inhibitors, for example empagliflozin, in combination with a RAAS inhibitor, for example a direct renin inhibitor, an Angiotensin-Converting Enzyme (ACE) inhibitor and/or an angiotensin II receptor blocker (ARB), for use in treating, preventing, protecting against or delaying the progression from no albuminuria to micro- or macroalbuminuria in a patient at risk for renal disease.

In a further aspect, the present invention relates to certain SGLT-2 inhibitors, for example empagliflozin, in combination with a RAAS inhibitor, for example a direct renin inhibitor, an Angiotensin-Converting Enzyme (ACE) inhibitor and/or an angiotensin II receptor blocker (ARB), for use in treating, preventing, protecting against or delaying the progression from microalbuminuria to macroalbuminuria in a patient with chronic kidney disease.

In a further aspect, the present invention relates to certain SGLT-2 inhibitors, for example empagliflozin, in combination with a RAAS inhibitor, for example a direct renin inhibitor, an Angiotensin-Converting Enzyme (ACE) inhibitor and/or an angiotensin II receptor blocker (ARB), for use in treating, preventing, protecting against delaying the progression of chronic kidney disease in a patient with chronic kidney disease.

In a further aspect, the present invention relates to certain SGLT-2 inhibitors, for example empagliflozin, in combination with a RAAS inhibitor, for example a direct renin inhibitor, an Angiotensin-Converting Enzyme (ACE) inhibitor and/or an angiotensin II receptor blocker (ARB), for use in treating, preventing, protecting against or delaying the occurrence of:

new onset of albuminuria,
doubling of serum creatinine level accompanied by an eGFR (based on modification of diet in renal disease (MDRD) formula)≥45 mL/min/1.73m2,
need for continuous renal replacement therapy, or
death due to renal disease.

In one aspect, a patient according of the present invention is a patient with prediabetes, type 1 or type 2 diabetes mellitus. In one aspect, a patient according to the present invention is a patient is a patient at risk for renal disease. In one aspect, a patient according to the present invention is a patient with or at risk of a cardiovascular disease. In one aspect, a patient according to the present invention is a patient with prediabetes, type 1 or type 2 diabetes mellitus and with or at risk of a cardiovascular disease.

Examples of Angiotensin-Converting Enzyme (ACE) inhibitors are Benazepril, Captopril, ramipril, lisinopril, Moexipril, cilazapril, quinapril, captopril, enalapril, benazepril, perindopril, fosinopril and trandolapril; the dosage(s) of some of these medications are for example shown below:

Benazepril (Lotensin), 5 mg, 10 mg, 20 mg, and 40 mg for oral administration
Captopril (Capoten), 12.5 mg, 25 mg, 50 mg, and 100 mg as scored tablets for oral administration
Enalapril (Vasotec), 2.5 mg, 5 mg, 10 mg, and 20 mg tablets for oral administration
Fosinopril (Monopril), for oral administration as 10 mg, 20 mg, and 40 mg tablets
Lisinopril (Prinivil, Zestril), 5 mg, 10 mg, and 20 mg tablets for oral administration
Moexipril (Univasc), 7.5 mg and 15 mg for oral administration
Perindopril (Aceon), 2 mg, 4 mg and 8 mg strengths for oral administration
Quinapril (Accupril), 5 mg, 10 mg, 20 mg, or 40 mg of quinapril for oral administration
Ramipril (Altace), 1.25 mg, 2.5 mg, 5, mg, 10 mg
Trandolapril (Mavik) , 1 mg, 2 mg, or 4 mg of trandolapril for oral administration Examples of angiotensin II receptor blockers (ARBs) are telmisartan, candesartan, valsartan, losartan, irbesartan, olmesartan, azilsartan and eprosartan; the dosage(s) of some of these medications are for example shown below:

Candesartan (Atacand), 4 mg, 8 mg, 16 mg, or 32 mg of candesartan cilexetil
Eprosartan (Teveten), 400 mg or 600 mg
Irbesartan (Avapro), 75 mg, 150mg, or 300 mg of irbesartan.
Losartan (Cozaar), 25 mg, 50 mg or 100 mg of losartan potassium
Telmisartan (Micardis) , 40 mg/12.5 mg, 80 mg/12.5 mg, and 80 mg/25 mg telmisartan and hydrochlorothiazide
Valsartan (Diovan) , 40 mg, 80 mg, 160 mg or 320 mg of valsartan A dosage of telmisartan is usually from 20 mg to 320 mg or 40 mg to 160 mg per day.

An example of a direct renin inhibitor is aliskiren (Tekturna). A dosage of aliskiren may be 150 mg or 300 mg per day.

Within this invention it is to be understood that the combinations, compositions or combined uses according to this invention may envisage the simultaneous, sequential or separate administration of the active components or ingredients.

In this context, "combination" or "combined" within the meaning of this invention may include, without being limited, fixed and non-fixed (e.g. free) forms (including kits) and uses, such as e.g. the simultaneous, sequential or separate use of the components or ingredients.

The combined administration of this invention may take place by administering the active components or ingredients together, such as e.g. by administering them simultaneously in one single or in two separate formulations or dosage forms. Alternatively, the administration may take place by administering the active components or ingredients sequentially, such as e.g. successively in two separate formulations or dosage forms.

For the combination therapy of this invention the active components or ingredients may be administered separately (which implies that they are formulated separately) or formulated altogether (which implies that they are formulated in the same preparation or in the same dosage form). Hence, the administration of one element of the combination of the present invention may be prior to, concurrent to, or subsequent to the administration of the other element of the combination.

In a further aspect, the present invention provides a pharmaceutical composition comprising a SGLT-2 inhibitor, for example empagliflozin, in combination with a RAAS inhibitor, for example a direct renin inhibitor, an Angiotensin-Converting Enzyme (ACE) inhibitor and/or an angiotensin II receptor blocker (ARB), for example as described herein.

Further embodiments, features and advantages of the present invention may become apparent from the following examples. The following examples serve to illustrate, by way of example, the principles of the invention without restricting it.

EXAMPLES

Example 1: Empagliflozin in Patients With Type 2 Diabetes Mellitus (T2DM) and Renal Impairment (RI)

A Phase III trial investigated the efficacy and safety of empagliflozin (EMPA) as add-on to existing therapy for 52 weeks in patients with T2DM and RI. Patients with mild RI (eGFR [MDRD equation]≥60 to<90 mL/min/1.73 m$^2$) received EMPA 10 or 25 mg qd or placebo (PBO). Patients with moderate RI (eGFR≥30 to<60 mL/min/1.73 m$^2$) received EMPA 25 mg qd or PBO. Patients with severe RI (eGFR≥5 to<30 mL/min/1.73 m$^2$) received EMPA 25 mg qd or PBO.

In patients with type 2 diabetes and mild renal impairment, treatment with empagliflozin 10 and 25 mg at week 52 resulted in a small decrease in eGFR. However, mean eGFR increased to a value slightly above baseline at the 3-week follow up visit in the empagliflozin treatment groups; in contrast, in the placebo group, mean eGFR further decreased (Table 1A).

TABLE 1A

Descriptive statistics for eGFR over time in patients with mild renal impairment

|  | Placebo | Empa 10 mg | Empa 25 mg |
|---|---|---|---|
| Number of patients N (%) | 32 (100.0) | 41 (100.0) | 38 (100.0) |
| Baseline eGFR |  |  |  |
| N* (%) | 32 (100.0) | 41 (100.0) | 38 (100.0) |
| Mean (SD) [mL/min/1.73 m$^2$] | 72.24 (12.68) | 68.42 (8.23) | 72.01 (10.84) |
| End-of treatment eGFR |  |  |  |
| N* (%) | 32 (100.0) | 38 (92.7) | 37 (97.4) |
| Mean (SD) [mL/min/1.73 m$^2$] | 70.34 (11.42) | 68.07 (11.36) | 66.25 (13.00) |
| Mean change from baseline (SD) [mL/min/1.73 m$^2$] | −1.89 (11.14) | −0.76 (9.42) | −5.67 (10.37) |
| Follow-up eGFR |  |  |  |
| N* (%) | 30 (93.8) | 38 (92.7) | 37 (97.4) |
| Mean (SD) [mL/min/1.73 m$^2$] | 68.20 (11.16) | 69.84 (11.29) | 73.38 (13.67) |
| Mean change from baseline (SD) [mL/min/1.73 m$^2$] | −3.84 (11.63) | 2.06 (8.91) | 1.28 (8.89) |

In patients with type 2 diabetes and moderate renal impairment, treatment with empagliflozin 25 mg at week 52 resulted a small decrease in eGFR while no change was seen for the placebo group. However, at the 3-week follow-up visit mean eGFR increased to a value slightly above baseline in the empagliflozin treatment group (Table 1B). Similar results were seen in patients with CKD 3A and B.

TABLE 1B

Descriptive statistics for eGFR over time in patients with moderate renal impairment

|  | Placebo | Empa 25 mg |
|---|---|---|
| Number of patients N (%) | 104 (100.0) | 105 (100.0) |
| Baseline eGFR |  |  |
| N* (%) | 104 (100.0) | 105 (100.0) |
| Mean (SD) [mL/min/1.73 m$^2$] | 43.35 (10.39) | 43.84 (8.70) |
| End-of treatment eGFR |  |  |
| N* (%) | 102 (98.1) | 101 (96.2) |
| Mean (SD) [mL/min/1.73 m$^2$] | 43.70 (11.08) | 40.58 (10.26) |
| Mean change from baseline (SD) [mL/min/1.73 m$^2$] | 0.04 (7.16) | −3.55 (6.63) |
| Follow-up eGFR |  |  |
| N* (%) | 98 (94.2) | 103 (98.1) |
| Mean (SD) [mL/min/1.73 m$^2$] | 42.99 (12.67) | 45.39 (11.31) |
| Mean change from baseline (SD) [mL/min/1.73 m$^2$] | 0.16 (9.14) | 1.48 (6.70) |

In patients with type 2 diabetes and severe renal impairment, treatment with empagliflozin 25 mg at week 52 resulted in a small decrease in eGFR. However, at the 3-week follow-up visit mean eGFR increased to a value slightly below baseline in the empagliflozin treatment group (Table 10).

TABLE 1C

Descriptive statistics for eGFR over time in patients with severe renal impairment

|  | Placebo | Empa 25 mg |
|---|---|---|
| Number of patients N (%) | 18 (100.0) | 21 (100.0) |
| Baseline eGFR |  |  |
| N* (%) | 18 (100.0) | 21 (100.0) |
| Mean (SD) [mL/min/1.73 m$^2$] | 22.90 (3.44) | 24.22 (3.99) |
| End-of treatment eGFR |  |  |
| N* (%) | 17 (94.4) | 21 (100.0) |
| Mean (SD) [mL/min/1.73 m$^2$] | 21.80 (6.36) | 20.23 (5.86) |
| Mean change from baseline (SD) [mL/min/1.73 m$^2$] | −1.17 (5.82) | −3.98 (5.80) |
| Follow-up eGFR |  |  |
| N* (%) | 18 (100.0) | 21 (100.0) |
| Mean (SD) [mL/min/1.73 m$^2$] | 21.42 (6.58) | 23.63 (7.40) |
| Mean change from baseline (SD) [mL/min/1.73 m$^2$] | −1.48 (6.03) | −0.59 (6.76) |

Example 2: Empagliflozin in Hypertensive Patients With Type 2 Diabetes Mellitus (T2DM)

A Phase III trial investigated the efficacy and safety of empagliflozin (EMPA) administered orally, once daily over 12 weeks in hypertensive patients with T2DM (EMPA 10 or 25 mg, placebo (PBO)). Patients with a systolic blood pressure (SBP) of 130 to 159 mmHg and a diastolic blood pressure (DSP) of 80 to 99 mmHg were included in the trial.

Treatment with empagliflozin 10 and 25 mg at week 12 resulted in a small decrease in eGFR. However, mean eGFR increased to a value slightly above baseline at the 2-week follow up visit in the empagliflozin treatment groups; in contrast, in the placebo group, mean eGFR remained slightly below baseline (Table 2).

TABLE 2

Descriptive statistics for eGFR (MDRD) over time

|  | Placebo | Empa 10 mg | Empa 25 mg |
|---|---|---|---|
| Baseline eGFR |  |  |  |
| N* (%) | 238 (100) | 241 (100) | 244 (100) |
| Mean (SD) [mL/min/1.73 m$^2$] | 84.47 (17.06) | 83.01 (16.43) | 83.97 (17.85) |
| Last value on treatment eGFR |  |  |  |
| N* (%) | 237 (99.6) | 238 (98.8) | 240 (98.4) |
| Mean (SD) [mL/min/1.73 m$^2$] | 84.16 (17.95) | 82.70 (17.11) | 81.24 (17.61) |
| Mean change from baseline (SD) [mL/min/1.73 m$^2$] | −0.27 (9.18) | −0.20 (8.99) | −2.60 (9.98) |

TABLE 2-continued

Descriptive statistics for eGFR (MDRD) over time

|  | Placebo | Empa 10 mg | Empa 25 mg |
|---|---|---|---|
| Follow-up eGFR | | | |
| N* (%) | 236 (99.2) | 238 (98.8) | 243 (99.6) |
| Mean (SD) [mL/min/1.73 m$^2$] | 83.52 (17.37) | 86.25 (17.06) | 86.60 (18.24) |
| Mean change from baseline (SD) [mL/min/1.73 m$^2$] | −0.82 (9.62) | 3.06 (10.05) | 2.75 (9.71) |
| N* (%) | 236 (99.2) | 236 (97.9) | 239 (98.0) |
| Mean change from last value on treatment (SD) [mL/min/1.73 m$^2$] | −0.52 (9.39) | 3.32 (9.75) | 5.54 (9.44) |

*Patients with values at this time point

Example 3: Empagliflozin in Patients With Type 2 Diabetes Mellitus (T2DM) Receiving Treatment with Basal Insulin A Phase IIb trial investigated the efficacy and safety of empagliflozin (EMPA 10 or 25 mg, placebo (PBO)) administered orally, once daily over 78 weeks in patients with T2DM receiving treatment with basal insulin (glargine, detemir, or NPH insulin only).

Treatment with empagliflozin 10 and 25 mg resulted in a small decrease in eGFR. However, mean eGFR increased to a value slightly below baseline at the 4-week follow up visit in the empagliflozin treatment groups; in contrast, in the placebo group, mean eGFR further slightly decreased (Table 3).

TABLE 3

Descriptive statistics for eGFR (MDRD) over time

|  | Placebo | Empa 10 mg | Empa 25 mg |
|---|---|---|---|
| Number of patients, N (%) | 170 (100.0) | 169 (100.0) | 155 (100.0) |
| Baseline eGFR | | | |
| N$^1$ (%) | 170 (100.0) | 169 (100.0) | 155 (100.0) |
| Mean (SD) | 83.89 (22.73) | 85.01 (23.63) | 82.88 (25.46) |

TABLE 3-continued

Descriptive statistics for eGFR (MDRD) over time

|  | Placebo | Empa 10 mg | Empa 25 mg |
|---|---|---|---|
| Week 18 eGFR | | | |
| N$^1$ (%) | 134 (78.8) | 133 (78.7) | 113 (72.9) |
| Mean (SD) | 80.07 (20.15) | 80.37 (23.03) | 79.11 (21.63) |
| Mean change from baseline (SD) | −4.12 (12.27) | −4.98 (11.40) | −3.48 (10.10) |
| Week 54 eGFR | | | |
| N$^1$ (%) | 106 (62.4) | 106 (62.7) | 97 (62.6) |
| Mean (SD) | 78.54 (21.06) | 82.55 (23.60) | 77.12 (23.59) |
| Mean change from baseline (SD) | −4.88 (10.85) | −5.68 (14.36) | −4.76 (11.05) |
| Week 78 eGFR | | | |
| N$^1$ (%) | 102 (60.0) | 100 (59.2) | 86 (55.5) |
| Mean (SD) | 78.52 (21.11) | 81.86 (24.17) | 77.21 (20.68) |
| Mean change from baseline (SD) | −5.27 (12.04) | −5.52 (11.08) | −5.64 (10.20) |
| eGFR at follow-up | | | |
| N$^1$ (%) | 112 | 118 | 113 |
| Mean (SD) | 78.36 (21.39) | 83.74 (21.69) | 81.35 (21.78) |
| Mean change from baseline (SD) | −6.66 (12.06) | −1.88 (13.02) | −0.79 (12.00) |

$^1$Percent of patient in population with values at this time point
eGFR = estimated glomerular filtration rate; MDRD = Modification of diet in renal disease; SD = standard deviation

Example 4: Empagliflozin in Patients With Type 2 Diabetes Mellitus (T2DM) and Microalbuminuria and Macroalbuminuria In a dedicated 52 week renal impairment study, patients were categorised based on their urine albumin/creatinine ratio (UACR) values at baseline, and 3 categories of patients were distinguished: patients with normal urine albumin/creatinine ratio values (<30 mg/g), patients with microalbuminuria (30 to<300 mg/g) and patients with macroalbuminurea (≥300 mg/g). Differences in mean changes from baseline between the placebo and the empagliflozin treatment groups were noted for patients with microalbuminuria or macroalbuminuria at baseline. For patients with microalbuminuria, mean urine albumin/creatinine ratio values increased with placebo treatment, remained nearly unchanged with empagliflozin 10 mg treatment, and decreased with empagliflozin 25 mg treatment. In patients with macroalbuminuria at baseline, a decrease in mean urine albumin/creatinine ratio was noted only in the empagliflozin groups; (Table 4A).

TABLE 4A

Urine albumin-to-creatinine ratio (mg/g) by baseline urine albumin-to-creatinine ratio at week 52 in normal patients and patients with microalbuminuria and macroalbuminuria

|  | Change from baseline | | | | | | | | |
|---|---|---|---|---|---|---|---|---|---|
|  | Normal | | | Microalbuminuria | | | Macroalbuminuria | | |
|  | N | Mean | SD | N | Mean | SD | N | Mean | SD |
| Placebo | 134 | 8.2 | 20.8 | 90 | 106.1 | 412.9 | 50 | 3.4 | 2050.5 |
| Empagliflozin 10 mg | 59 | 4.0 | 15.3 | 17 | 7.4 | 137.3 | 9 | −716.3 | 1273.6 |
| Empagliflozin 25 mg | 141 | 6.0 | 31.7 | 72 | −39.4 | 93.8 | 61 | −799.9 | 1543.7 |

Shifts between UACR categories at baseline and the end of treatment were noted in the randomised treatment groups (Table 4B). A higher frequency of patients in the empagliflozin treatment groups shifted from macro- or microalbuminura at baseline towards normal values and from macro- to microalbuminuria at the end of treatment. In addition, a higher proportion of patients in the placebo group shifted from normal values at baseline towards microalbuminuria at the end of treatment.

TABLE 4B

Frequency of patients [N (%)] with shifts in urine albumin-to-creatinine ratio (mg/g) at Week 52 relative to urine albumin-to-creatinine ratio categories at baseline

| Treatment | Baseline | Last value on-treatment | | |
|---|---|---|---|---|
| | | Normal N (%) | Micro-albuminuria N (%) | Macro-albuminuria N (%) |
| Placebo | Normal | 118 (81.9) | 26 (18.1) | 0 |
| | Micro-albuminuria | 22 (21.8) | 67 (66.3) | 12 (11.9) |
| | Macro-albuminuria | 1 (1.7) | 6 (10.0) | 53 (88.3) |
| Empa 10 mg | Normal | 59 (89.4) | 7 (10.6) | 0 |
| | Micro-albuminuria | 5 (27.8) | 11 (61.1) | 2 (11.1) |
| | Macro-albuminuria | 1 (11.1) | 5 (55.6) | 3 (33.3) |
| Empa 25 mg | Normal | 135 (89.4) | 16 (10.6) | 0 |
| | Micro-albuminuria | 19 (24.1) | 57 (72.2) | 3 (3.8) |
| | Macro-albuminuria | 2 (2.7) | 22 (30.1) | 49 (67.1) |

Categories for urine albumin-to-creatinine ratio: normal: <30 mg/g, microalbuminuria 30 to <300 mg/g, macroalbuminuria: ≥300 mg/g Categories for urine albumin-to-creatinine ratio: normal:<30 mg/g, microalbuminuria 30 to<300 mg/g, macroalbuminuria:≥300 mg/g

Example of Pharmaceutical Composition and Dosage Form

The following example of solid pharmaceutical compositions and dosage forms for oral administration serves to illustrate the present invention more fully without restricting it to the contents of the example. Further examples of compositions and dosage forms for oral administration, are described in WO 2010/092126. The term "active substance" denotes empagliflozin according to this invention, especially its crystalline form as described in WO 2006/117359 and WO 2011/039107.

Tablets containing 2.5mg, 5mg, 10mg, 25mg, 50mg of active substance

| Active substance | 2.5 mg/ per tablet | 5 mg/ per tablet | 10 mg/ per tablet | 25 mg/ per tablet | 50 mg/ per tablet |
|---|---|---|---|---|---|
| Wet granulation | | | | | |
| active substance | 2.5000 | 5.000 | 10.00 | 25.00 | 50.00 |
| Lactose Monohydrate | 40.6250 | 81.250 | 162.50 | 113.00 | 226.00 |
| Microcrystalline Cellulose | 12.5000 | 25.000 | 50.00 | 40.00 | 80.00 |
| Hydroxypropyl Cellulose | 1.8750 | 3.750 | 7.50 | 6.00 | 12.00 |
| Croscarmellose Sodium | 1.2500 | 2.500 | 5.00 | 4.00 | 8.00 |
| Purified Water Dry Adds | q.s. | q.s. | q.s. | q.s. | q.s. |
| Microcrystalline Cellulose | 3.1250 | 6.250 | 12.50 | 10.00 | 20.00 |
| Colloidal silicon dioxide | 0.3125 | 0.625 | 1.25 | 1.00 | 2.00 |
| Magnesium stearate | 0.3125 | 0.625 | 1.25 | 1.00 | 2.00 |
| Total core Film Coating | 62.5000 | 125.000 | 250.00 | 200.00 | 400.00 |
| Film coating system | 2.5000 | 4.000 | 7.00 | 6.00 | 9.00 |
| Purified Water | q.s. | q.s. | q.s. | q.s. | q.s. |
| Total | 65.000 | 129.000 | 257.00 | 206.00 | 409.00 |

Details regarding the manufacture of the tablets, the active pharmaceutical ingredient, the excipients and the film coating system are described in WO 2010/092126, in particular in the Examples 5 and 6, which hereby is incorporated herein in its entirety.

The invention claimed is:

1. A method of treating, reducing the risk of, delaying the occurrence of and/or delaying the progression of chronic kidney disease in a patient, said method comprising administering to the patient a pharmaceutially effective amount of empagliflozin, optionally in combination with one or more other therapeutic substances.

2. The method according to claim 1, wherein the progression of said chronic kidney disease is the progression to end stage renal disease/kidney failure, or renal death in the patient.

3. The method according to claim 1, wherein said patient is at risk for renal disease.

4. The method according to claim 1, wherein the patient is a patient with prediabetes, type 1 or type 2 diabetes mellitus.

5. The method according to claim 4, wherein the patient is a patient with type 2 diabetes mellitus.

6. The method according to claim 1, wherein the patient has or is at risk of a cardiovascular disease.

7. The method according to claim 1, wherein the patient is a patient with prediabetes, type 1 or type 2 diabetes mellitus and with or at risk of a cardiovascular disease.

8. The method according to claim 1, wherein the patient has a loss of eGFR of less than 50%.

9. The method according to claim 1, wherein the patient is a patient with one or more cardiovascular risk factors selected from the group consiting of A), B), C) and D):
   A) previous or existing vascular disease selected from the group consisting of myocardial infarction, coronary artery disease, percutaneous coronary intervention, coronary artery by-pass grafting, ischemic or hemorrhagic stroke, congestive heart failure, and peripheral occlusive arterial disease,
   B) advanced age>/=60-70 years,
   C) one or more cardiovascular risk factors selected from the group consisting of
      advanced type 1 or type 2 diabetes mellitus>10 years duration, hypertension,
current daily cigarette smoking,
dyslipidemia,
obesity,
age>/=40,
metabolic syndrome, hyperinsulinemia or insulin resistance, and
hyperuricemia, erectile dysfunction, polycystic ovary syndrome, sleep apnea, or family history of vascular disease or cardiomyopathy in first-degree relative,
D) one or more of the following:
confirmed history of myocardial infarction,
unstable angina with documented multivessel coronary disease or positive stress test,
multivessel Percutaneous Coronary Intervention,
multivessel Coronary Artery By-pass Grafting (CABG),
history of ischemic or hemorrhagic stroke, or
peripheral occlusive arterial disease.

10. The method according to claim 1, wherein the one or more other therapeutic substances are selected from other antidiabetic substances.

11. The method according to claim 1, comprising administering empagliflozin in combination with metformin, with linagliptin or with metformin and linagliptin.

12. The method according to claim 1, wherein the one or more other therapeutic substances is a renin angiotensin aldosterone system (RAAS) inhibitor.

13. The method according to claim 1, wherein the one or more other therapeutic substances is a direct renin inhibitor, an Angiotensin-Converting Enzyme (ACE) inhibitor and/or an angiotensin II receptor blocker (ARB).

14. The method according to claim 1, comprising administering empagliflozin in combination with a renin angiotensin aldosterone system (RAAS) inhibitor.

15. The method according to claim 1, comprising administering empagliflozin in combination with a direct renin inhibitor, an Angiotensin-Converting Enzyme (ACE) inhibitor and/or an angiotensin II receptor blocker (ARB).

16. The method according to claim 1, wherein empagliflozin is administered orally in a total daily amount of 10 mg or 25 mg.

17. The method according to claim 1, wherein empagliflozin is administered as a pharmaceutical composition comprising 10 mg or 25 mg of empagliflozin.

18. The method according to claim 1, wherein the method protects against or delays the loss of estimated glomerular filtration rate (eGFR) in the patient.

19. The method according to claim 1, wherein the method reduces the progression to end stage renal disease/kidney failure in the patient.

20. The method according to claim 1, wherein the method reduces the risk of progression to renal death in the patient.

21. The method according to claim 1, wherein the patient is a patient with chronic kidney disease.

22. The method according to claim 21, wherein the patient is a patient with stage 3 chronic kidney disease.

23. The method according to claim 21, wherein the patient is a patient with stage 3B chronic kidney disease.

24. The method according to claim 21, wherein the patient is a patient with stage 4 chronic kidney disease.

25. The method according to claim 1, wherein the method protects against or delays the loss of estimated glomerular filtration rate (eGFR) in the patient, and wherein the patient has chronic kidney disease.

26. The method according to claim 1, wherein the method reduces the progression to end stage renal disease/kidney failure in the patient, and wherein the patient has chronic kidney disease.

27. The method according to claim 1, wherein the method reduces the risk of progression to renal death in the patient, and wherein the patient has chronic kidney disease.

28. A method for treating a patient having chronic kidney disease, the method comprising administering to the patient a pharmaceutically effective amount of empagliflozin, optionally in combination with one or more other therapeutic substances, wherein:
the method protects against or delays the loss of estimated glomerular filtration rate (eGFR) in the patient, the method reduces the progression to end stage renal disease/kidney failure in the patient, and/or the method reduces the risk of progression to renal death in the patient.

29. A method for treating a patient having chronic kidney disease, the method comprising administering to the patient a pharmaceutically effective amount of empagliflozin, optionally in combination with one or more other therapeutic substances, wherein the method protects against or delays the loss of estimated glomerular filtration rate (eGFR) in the patient.

30. A method for treating a patient having chronic kidney disease, the method comprising administering to the patient a pharmaceutically effective amount of empagliflozin, optionally in combination with one or more other therapeutic substances, wherein the method reduces the progression to end stage renal disease/kidney failure in the patient.

31. A method for treating a patient having chronic kidney disease, the method comprising administering to the patient a pharmaceutically effective amount of empagliflozin, optionally in combination with one or more other therapeutic substances, wherein the method reduces the risk of progression to renal death in the patient.

32. A method for treating, reducing the risk of and/or delaying the progression of chronic kidney disease in a patient with chronic kidney disease, said method comprising administering to the patient a pharmaceutically effective amount of empagliflozin, optionally in combination with one or more other therapeutic substances.

* * * * *